(12) United States Patent
Brotherton-Pleiss et al.

(10) Patent No.: US 8,435,990 B2
(45) Date of Patent: May 7, 2013

(54) DIHYDROPYRIMIDONE AMIDES AS P2X7 MODULATORS

(75) Inventors: Christine E. Brotherton-Pleiss, Sunnyvale, CA (US); Joan Marie Caroon, Mountain View, CA (US); Francisco Javier Lopez-Tapia, Mahwah, NJ (US); Keith Adrian Murray Walker, Los Altos Hills, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 172 days.

(21) Appl. No.: 12/847,129

(22) Filed: Jul. 30, 2010

(65) Prior Publication Data

US 2011/0028502 A1 Feb. 3, 2011

Related U.S. Application Data

(60) Provisional application No. 61/229,818, filed on Jul. 30, 2009.

(51) Int. Cl.
*C07D 239/22* (2006.01)
*C07D 403/12* (2006.01)
*A61K 31/513* (2006.01)

(52) U.S. Cl.
USPC ...... 514/242; 514/252.02; 514/274; 544/182; 544/238; 544/296; 544/316

(58) Field of Classification Search .................. 544/182, 544/238, 296, 316; 514/242, 252.02, 274
See application file for complete search history.

(56) References Cited

U.S. PATENT DOCUMENTS

2007/0099944 A1   5/2007   Drewry

FOREIGN PATENT DOCUMENTS

| WO | 0078730 A1 | 12/2000 |
| WO | 0246162 A1 | 6/2002 |
| WO | WO 2007/073505 | * 6/2007 |

OTHER PUBLICATIONS

Kappe, C. O., et. al. "The Biginelli Dihydropyrimidine Synthesis," Organic Reactions, 2004, vol. 63, Chapter 1.
Virsodia, V., et. al. "Synthesis, screening for antitubercular activity and 3D-QSAR studies of substituted N-phenyl-6-methyl-2-oxo-4-phenyl-1,2,3,4-tetrahydro-pyrimidine-5-carboxamides," European Journal of Medicinal Chemistry, 2008, vol. 43, pp. 2103-2115.

* cited by examiner

*Primary Examiner* — Deepak Rao
(74) *Attorney, Agent, or Firm* — Robert C. Hall

(57) ABSTRACT

Compounds of the formula I:

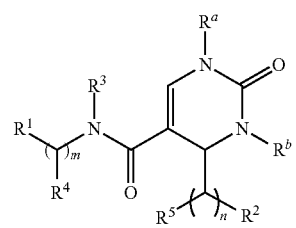

or pharmaceutically acceptable salts thereof, wherein m, n, $R^1$, $R^2$, $R^3$, $R^4$, $R^5$, $R^a$ and $R^b$ are as defined herein. Also disclosed are methods of making the compounds and using the compounds for treatment of diseases associated with the P2X7 purinergic receptor.

21 Claims, No Drawings

DIHYDROPYRIMIDONE AMIDES AS P2X7 MODULATORS

CROSS REFERENCE TO RELATED APPLICATIONS

This application claims the benefit of priority of U.S. Provisional Patent Application Ser. No. 61/229,818, filed Jul. 30, 2009, the disclosure of which is incorporated herein by reference in its entirety.

FIELD OF THE INVENTION

This invention pertains to compounds useful for treatment of diseases associated with P2X purinergic receptors, and more particularly to $P2X_7$ modulators usable for treatment of autoimmune and inflammatory diseases.

BACKGROUND OF THE INVENTION

P2X purinergic receptors are ATP-activated ionotropic receptors having seven subtypes. The P2X7 receptor subtype (also known as the P2Z receptor) is a ligand-gated ion channel found on mast cells, peripheral macrophages, lymphocytes, erythrocytes, fibroblasts and epidermal langerhans cells. Activation of P2X7 receptor on such immune system cells results in release of interleukin-1beta. (Solle et al., *J. Biol. Chemistry* 276, 125-132, (2001)). The P2X7 receptor is also found on microglia, Schwann cells and astrocytes within the central nervous system (Donnelly-Roberts et al., *Br. J. Pharmacol.* 151, 571-579 (2007)).

Antagonists of P2X7 have been showned to block P2×7-mediated IL-1beta release and P2×7-mediated cation flux (Stokes et al., *Br. J. Pharmacol.* 149, 880-887 (2006)). Mice lacking the P2X7 receptor show a lack of inflammatory and neuropathic hypersensitivity to mechanical and thermal stimuli (Chessell et al., *Pain* 114, 386-396 (2005)). P2X7 is thus believed to have a role in inflammatory responses (Ferrari et al., *J. Immunol.* 176, 3877-3883 (2006)) and in the onset and persistence of chronic pain (Honore et al., *J. Pharmacol. Ex. Ther.* 319, 1376-1385 (2006b)). The P2X7 receptor has also been shown to mediate superoxide production in primary microglia, which is up-regulated in a transgenic mouse model of Alzheimer's disease (*J. Biol. Chem.* April 11, 278(15), 13309-17 (2003).

Modulators of the P2X7 receptor thus may have utility in the treatment of disease states such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, diabetes and Crohn's disease. P2X7 modulators may also be useful for treatment of pain, including chronic pain, neuropathic pain, and pain associated inflammatory processes and degenerative conditions. P2X7 modulators may further be useful in the treatment of memory disorders such as Alzheimer's disease, and the enhancement of cognitive memory.

There is accordingly a need for compounds that act as modulators of P2X receptors, including antagonists of P2X7 receptor, as well as a need for methods of treating diseases, conditions and disorders mediated by P2X7 The present invention satisfies these needs as well as others.

SUMMARY OF THE INVENTION

The invention provides compounds of the formula I:

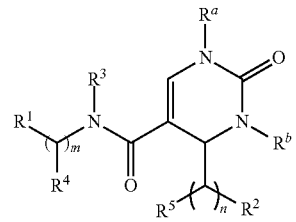

or pharmaceutically acceptable salts thereof,
wherein:
  m is 0 or 1;
  n is 0 or 1;
  $R^1$ is:
    substituted phenyl; or
    optionally substituted heteroaryl;
  $R^2$ is:
    optionally substituted phenyl;
    optionally substituted heteroaryl; or
    optionally substituted $C_{3-6}$cycloalkyl;
  $R^3$ is:
    hydrogen;
    $C_{1-6}$alkyl;
    alkylcarbonylalkyl; or
    alkoxycarbonylalkyl;
  $R^4$ and $R^5$ each independently is:
    hydrogen; or
    $C_{1-6}$alkyl;
  $R^a$ is:
    hydrogen;
    $C_{1-6}$alkyl;
    hydroxy-$C_{1-6}$alkyl;
    $C_{1-6}$alkoxy-$C_{1-6}$alkyl;
    hydroxy-$C_{1-6}$alkoxy-$C_{1-6}$alkyl;
    $C_{1-6}$alkylcarbonyl;
    $C_{1-6}$alkylsulfonyl-$C_{1-6}$alkyl;
    aminocarbonyl-$C_{1-6}$alkyl; or
    hydroxy $C_{1-6}$alkoxy-$C_{1-6}$alkyl; and
  $R^b$ is:
    hydrogen; or
    $C_{1-6}$alkyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Alkylcarbonylaminoalkyl" means a moiety of the formula —R—NR'—C(O)—R" wherein R is alkylene, R' is hydrogen or alkyl, and R" is alkyl as defined herein.

"Alkoxycarbonylaminoalkyl" means a moiety of the formula —R—NR'—C(O)—OR" wherein R is alkylene, R' is hydrogen or alkyl, and R" is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfinyl" means a moiety of the formula —SO—R, wherein R is alkyl as defined herein.

"Alkylsulfanyl" means a moiety of the formula —S—R, wherein R is alkyl as defined herein.

"Alkylsulfonylalkyl means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hyrdogen or alkyl as defined herein. "Amino thus includes "alkylamino" (where one of R and R' is alkyl and the other is hydrogen) and "dialkylamino" (where R and R' are both alkyl.

"Aminocarbonyl" means a group of the formula —C(O)—R wherein R is amino as defined herein. "Aminocarbonyl" thus includes "alkylaminocarbonyl" and "dialkylaminocarbonyl".

"Aminocarbonylalkyl" means a group of the formula —R—C(O)—R' wherein R is alkylene and R' is amino as defined herein. "Aminocarbonylalkyl" thus includes alkylaminocarbonylalkyl" and dialkylaminocarbonylalkyl".

"Aminocarbonylalkoxy" means a group of the formula —O—R—C(O)—R' wherein R is alkylene and R' is amino as defined herein.

"Alkoxyamino" means a moiety of the formula —NR—OR' wherein R is hydrogen or alkyl and R' is alkyl as defined herein.

"Alkoxyaminoalkyl" means a moiety of the formula —O—R—NR'—OR" wherein R is alkylene, R' is hydrogen or alkyl, and R" is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl" means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Preferred cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof "Cycloalkylalkyl" means a moiety of the formula —R'—R", where R' is alkylene and R" is cycloalkyl as defined herein.

"Cycloalkoxy" means a group of the formula —O—R wherein R is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

"Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxyalkoxy" means a moiety of the formula —OR wherein R is hydroxyalkyl as defined herein.

"Hydroxyalkoxyalkyl" means a moiety of the formula —ROR' wherein R is alkylene and R' is alkyl as defined herein, and R or R' or both are substituted with hydroxy.

"Hydroxyalkoxyalkyl" thus includes, for example, 2-hydroxy-3-methoxy-propyl and 3-hydroxy-2-methoxy-propyl.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonyl" or "carboxy" means a group of the formula —(CO)—OH.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$— CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled artisans will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Arthritis" means diseases or conditions damage to joints of the body and pain associated with such joint damage. Arthritis includes rheumatoid arthritis, osteoarthritis, psoriatic arthritis, septic arthritis and gouty arthritis.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state, (ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include also deuterium and tritium isotopes, and the carbon atoms are meant to include $C^{13}$ and $C^{14}$ isotopes.

All patents and publications identified herein are incorporated herein by reference in their entirety.

COMPOUNDS OF THE INVENTION

The invention provides compounds of the formula I:

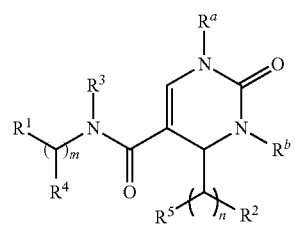

I or pharmaceutically acceptable salts thereof,
wherein:
m is 0 or 1;
n is 0 or 1;
$R^1$ is:
substituted phenyl; or
optionally substituted heteroaryl;
$R^2$ is:
optionally substituted phenyl;
optionally substituted heteroaryl; or optionally substituted $C_{3-6}$cycloalkyl;
$R^3$ is:
hydrogen;
$C_{1-6}$alkyl;
alkylcarbonylalkyl; or
alkoxycarbonylalkyl;
$R^4$ and $R^5$ each independently is:
hydrogen; or
$C_{1-6}$alkyl;
$R^a$ is:
hydrogen;
$C_{1-6}$alkyl;
hydroxy-$C_{1-6}$alkyl;
$C_{1-6}$alkoxy-$C_{1-6}$alkyl;
hydroxy-$C_{1-6}$alkoxy-$C_{1-6}$alkyl;
$C_{1-6}$alkylcarbonyl;
$C_{1-6}$alkylsulfonyl-$C_{1-6}$alkyl;
aminocarbonyl-$C_{1-6}$alkyl; or
hydroxy $C_{1-6}$alkoxy-$C_{1-6}$alkyl; and
$R^b$ is:
hydrogen; or
$C_{1-6}$alkyl.

In certain embodiments of formula I, $R^3$, $R^4$ and $R^5$ are hydrogen.

In certain embodiments of formula I, $R^3$, $R^4$, $R^5$ and $R^a$ are hydrogen.

In certain embodiments of formula I, m is 0.

In certain embodiments of formula I, n is 0.

In certain embodiments of formula I, $R^3$ is hydrogen.

In certain embodiments of formula I, $R^4$ is hydrogen.

In certain embodiments of formula I, $R^5$ is hydrogen.

In certain embodiments of formula I, $R^1$ is substituted phenyl.

In certain embodiments of formula I, $R^1$ is phenyl substituted one, two, three or four times, and preferably substituted one, two or three times, with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfony-$C_{1-6}$alkoxy; hydroxy-$C_{1-6}$alkyl; $C_{3-6}$cycloalkyl-$C_{1-6}$ alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; hydroxy $C_{1-6}$alkoxy-$C_{1-6}$ alkyl; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonyl$C_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$ alkyl; or nitro; a five- or six-membered heteroaryl selected from: pyrrolyl; pyrazolyl; triazolyl; oxazolyl; isoxazolyl; thiazolyl; isothiazolyl; thiadiazolyl; oxadiazolyl; oxazolidinyl; pyridinyl; pyrimidinyl; pyrazinyl; pyridazinyl; or triazinyl, each optionally substituted; or two adjacent substituents may form a $C_{1-2}$alkylenedioxy or halo-$C_{1-2}$alkylenedioxy.

In certain embodiments of formula I, $R^1$ is phenyl substituted one, two, three or four times, and preferably substituted one, two or three times, with a substituent or substituents each independently selected from: fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; a five- or six-membered heteroaryl selected from: pyrrolyl; pyrazolyl; triazolyl; oxazolyl; isoxazolyl; thiazolyl; isothiazolyl; thiadiazolyl; oxadiazolyl; oxazolidinyl; pyridinyl; pyrimidinyl; pyrazinyl; pyridazinyl; or triazinyl, each optionally substituted; or two adjacent substituents may form methylenedioxy, ethylenedioxy or difluoromethylenedioxy.

In certain embodiments of formula I, $R^1$ is phenyl substituted one, two, three or four times, and preferably substituted one, two or three times, with a substituent or substituents each independently selected from: fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; or a five- or six-membered heteroaryl selected from: pyrazolyl; triazolyl; pyridinyl; pyrimidinyl; pyrazinyl; pyridazinyl; or triazinyl, each optionally substituted once or twice with a group or groups independently selected from $C_{1-6}$alkyl, hydroxy-$C_{1-6}$alkyl, hydroxy-$C_{1-6}$alkoxy-$C_{1-6}$alkyl, and oxo.

In certain embodiments of formula I, $R^1$ is phenyl substituted one, two, three or four times, and preferably substituted one, two or three times, with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; $C_{1-6}$alkoxy-$C_{1-6}$alkoxy; hydroxy-$C_{1-6}$alkoxy; $C_{1-6}$alkylsulfonyl-$C_{1-6}$alkoxy; hydroxy-$C_{1-6}$alkyl; hydroxy-$C_{1-6}$alkylamino; $C_{1-2}$alkylenedioxy; $C_{3-6}$cycloalkyl-$C_{1-6}$alkoxy; or a five- or six-membered heteroaryl selected from: pyrazolyl; triazolyl; pyridinyl; pyrimidinyl; pyrazinyl; pyridazinyl; or triazinyl, each optionally substituted once or twice with a group or groups independently selected from $C_{1-6}$alkyl, hydroxy-$C_{1-6}$alkyl, hydroxy-$C_{1-6}$alkoxy-$C_{1-6}$alkyl, and oxo.

In certain embodiments of formula I, $R^1$ is phenyl substituted one, two, three or four times, and preferably substituted one, two or three times, with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; ethylenedioxy; pyrrol-1-yl; 2-hydroxy-5-methyl-pyrazol-3-yl; 2-methyl-tetrazol-5-yl; 1,5-dimethyl-pyrazol-3-yl; pyrazol-3-yl; 5-methyl-pyridin-2-yl; 1-(2-hydroxy-propyl)-5-methyl-pyrazol-3-yl; 2-isobutyl-pyrazol-3-yl; 1-methyl-tetrazol-5-yl; 6-methyl-pyridin-3-yl; pyrazol-1-yl; 2-methyl-pyrazol-3-yl; 5-ethyl-pyrazol-3-yl; 4,5-dimethyl-pyrazol-3-yl; 3,5-dioxo-4-5-dihydro[1,2,4]triazin-2-yl; 5-ethyl-1H-pyrazol-3-yl; 1,5-dimethyl-1H-pyrazol-3-yl; 1-(2,3-dihydroxy-propyl)-5-methyl-1H-pyrazol-3-yl; 2,5-dimethyl-2H-pyrazol-3-yl; 5-methyl-1H-[1,2,4]triazol-3-yl; 1,5-dimethyl-1H-[1,2,4]triazol-3-yl; 3-methyl-isoxazol-5-yl; 3-methyl-[1,2,4]triazol-1-yl; 4-methyl-[1,2,3]triazol-1-yl; 4-methyl-pyrazol-1-yl; 5-methyl-[1,3,4]oxadiazol-2-yl; 2-propyl-pyrazol-3-yl; 4,5-dimethyl-[1,2,4]triazol-3-yl; 2-oxo-oxazolidin-3-ylmethyl; 4-methyl-3,5-dioxo-4,5-dihydro-[1,2,4]triazin-2-yl; 5-methyl-pyrazol-3-yl; 4-(2-hydroxy-ethyl)-3,5-dioxo-4,5-dihydro-[1,2,4]triazin-2-yl; 5-methyl-isoxazol-3-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

In certain embodiments of formula I, $R^1$ is phenyl substituted one, two, three or four times, and preferably substituted one, two or three times, with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; ethylenedioxy; pyrrol-1-yl; 2-hydroxy-5-methyl-pyrazol-3-yl; 2-methyl-tetrazol-5-yl; 1,5-dimethyl-pyrazol-3-yl; pyrazol-3-yl; 5-methyl-pyridin-2-yl; 1-(2-hydroxy-propyl)-5-methyl-pyrazol-3-yl; 2-isobutyl-pyrazol-3-yl; 1-methyl-tetrazol-5-yl; 6-methyl-pyridin-3-yl; pyrazol-1-yl; 2-methyl-pyrazol-3-yl; 5-ethyl-pyrazol-3-yl; 4,5-dimethyl-pyrazol-3-yl; 3,5-dioxo-4-5-dihydro[1,2,4]triazin-2-yl; 5-ethyl-1H-pyrazol-3-yl; 1,5-dimethyl-1H-pyrazol-3-yl; 1-((R)-2,3-dihydroxy-propyl)-5-methyl-1H-pyrazol-3-yl; 2,5-dimethyl-2H-pyrazol-3-yl; 5-methyl-1H-[1,2,4]triazol-3-yl; 1,5-dimethyl-1H-[1,2,4]triazol-3-yl; 3-methyl-isoxazol-5-yl; 3-methyl-[1,2,4]triazol-1-yl; 4-methyl-[1,2,3]triazol-1-yl; 4-methyl-pyrazol-1-yl; 5-methyl-[1,3,4]oxadiazol-2-yl; 2-propyl-pyrazol-3-yl; 4,5-dimethyl-[1,2,4]triazol-3-yl; 2-oxo-oxazolidin-3-ylmethyl; 4-methyl-3,5-dioxo-4,5-dihydro-[1,2,4]triazin-2-yl; 5-methyl-pyrazol-3-yl; 4-(2-hydroxy-ethyl)-3,5-dioxo-4,5-dihydro-[1,2,4]triazin-2-yl; 5-methyl-isoxazol-3-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

In certain embodiments of formula I, $R^1$ is phenyl substituted at the two position with halo or $C_{1-6}$alkyl, and substituted one or two additional times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; $C_{1-6}$alkoxy-$C_{1-6}$alkoxy; hydroxy-$C_{1-6}$alkoxy; $C_{1-6}$alkylsulfonyl-$C_{1-6}$alkoxy; hydroxy-$C_{1-6}$alkyl; hydroxy-$C_{1-6}$alkylamino; $C_{1-2}$alkylenedioxy; or $C_{3-6}$cycloalkyl-$C_{1-6}$alkoxy.

In certain embodiments of formula I, $R^1$ is phenyl substituted at the two position $C_{1-6}$alkyl, and substituted one or two additional times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; $C_{1-6}$alkoxy-$C_{1-6}$alkoxy; hydroxy-$C_{1-6}$alkoxy; $C_{1-6}$alkylsulfonyl-$C_{1-6}$alkoxy; hydroxy-$C_{1-6}$alkyl; hydroxy-$C_{1-6}$alkylamino; $C_{1-2}$alkylenedioxy; or $C_{3-6}$cycloalkyl-$C_{1-6}$alkoxy.

In certain embodiments of formula I, $R^1$ is phenyl substituted two or three times with substituents each independently selected from: fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of formula I, $R^1$ is phenyl substituted two or three times with substituents each independently selected from: fluoro; chloro; bromo; methyl; and methoxy.

In certain embodiments of formula I, $R^1$ is phenyl optionally substituted one, two or three times with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, $R^1$ is phenyl substituted at the two position with methyl or halo, and additionally substituted one or two times times with a substituent or substituents each independently selected from: fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of formula I, $R^1$ is phenyl substituted at the two position with methyl, and additionally substituted one or two times with a substituent or substituents each independently selected from: fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2,4-dichloro-5-methoxy-phenyl; 2-bromo-5-methoxy-4-trifluoromethyl-phenyl; 2-bromo-4,5-dichloro-phenyl; 2-bromo-4-chloro-5-iodo-phenyl; 2-bromo-4-chloro-5-trifluoromethyl-phenyl; 2-bromo-5-methoxy-4-methyl-phenyl; 2-isopropyl-4,5-dimethoxy-phenyl; 2-bromo-4-chloro-5-methanesulfanyl-phenyl; 2-bromo-4-chloro-5-methanesulfonyl-phenyl; 2-bromo-4-chloro-5-methanesulfinyl-phenyl; 2-bromo-4-chloro-5-fluoro-phenyl; 2-bromo-5-methoxy-phenyl; 2-bromo-5-methoxy-4-methoxycarbonyl-phenyl; 2-bromo-4-chloro-5-hydroxy-phenyl; 2-bromo-4-chloro-5-(methylamino-carbonyl-methyoxy)-phenyl; 2-methyl-4,5-dimethoxy-phenyl; 2-bromo-4-chloro-5-methoxycarbonyl-phenyl; 2-bromo-4-methanesulfonyl-5-methoxy-phenyl; 2-bromo-4-methyl-5-methoxy-phenyl; 2-bromo-4-chloro-5-(methoxycarbonyl-methoxy)-phenyl; 2-bromo-4-chloro-5-(hydroxycarbonyl-methoxy)-phenyl; 2-bromo-4-chloro-5-(2-methoxyethoxy)-phenyl; 4,5-dimethoxy-phenyl; 2-fluoro-4-chloro-5-methoxy-phenyl; 2-bromo-4-methoxycarbonyl-5-methoxy-phenyl; 6-bromo-benzo[1,3]dioxol-5-yl; 2-bromo-4-chloro-5-(2-hydroxyethoxy)-phenyl; 2-bromo-4-difluoromethoxy-5-methoxy-phenyl; 5-methoxy-4-methyl-phenyl; 2-bromo-4-chloro-5-(2-methylamino-ethoxy)-phenyl; 2-bromo-4-cyano-5-methylphenyl; 2-fluoro-4-methyl-5-methoxy-phenyl; 2-bromo-4-chloro-5-acetyl-phenyl; 5-methoxy-2-methyl-phenyl; 2-bromo-4-chloro-5-(3-methanesulfonyl-propoxy)-phenyl; 2-bromo-5-methoxy-4-(tert-butoxycarbonyl)-phenyl; 5-methanesulfonyl-2-methoxy-phenyl; 2-bromo-4-chloro-5-(1-hydroxyethyl)-phenyl; 2-fluoro-5-(2-hydroxyethoxy)-4-methyl-phenyl; 2-bromo-5-methoxy-4-aminocarbonyl-phenyl; 6-bromo-2,2-difluoro-benzo[1,3]dioxol-5-yl; 2,6-difluoro-phenyl; 2-bromo-4-cyano-5-methoxy-phenyl; 2,5-dimethoxy-phenyl; 3-methoxycarbonyl-2-methyl-phenyl; 3-methoxy-phenyl; 4-methoxy-phenyl; 2,4-dimethoxy-phenyl; 4-chloro-5-methoxy-phenyl; 4-fluoro-5-methoxy-phenyl; 2-bromo-4-methyl-5-(tert-butoxycarbonyl)-phenyl; 3,4,5-trimethoxy-phenyl; 2-bromo-4,6-difluoro-phenyl; 2-ethyl-4,5-dimethoxy-phenyl; 2-bromo-4-methoxy-phenyl; 4-chloro-5-(2-hydroxyethoxy)-2-methyl-phenyl; 3-methoxycarbonyl-2-methyl-phenyl; 2,5-dimethyl-phenyl; 2-bromo-5-methoxy-phenyl; 2,3-dimethyl-phenyl; 2-bromo-4-chloro-5-hydroxymethyl-phenyl; 2-bromo-3,5-dimethyl-phenyl; 4-methoxy-2-methyl-phenyl; 2,4-dimethyl-phenyl; 2-iodo-4,5-dimethoxy-phenyl; 2-chloro-4,5-dimethoxy-phenyl; 7-bromo-2,3-dihydrobenzo[1,4]dioxin-6-yl; 4,5-dimethoxy-2-trifluoromethyl-phenyl; 2-bromo-5-ethoxy-4-methoxy-phenyl; 2-bromo-4-ethoxy-5-methoxy-phenyl; 2-bromo-5-cyclopropyl-methoxy-4-methoxy-phenyl; 2-bromo-4-cyclopropyl-methoxy-5-methoxy-phenyl; 2-cyano-4,5-dimethoxyphenyl; 2-bromo-5-difluoromethoxy-4-methoxy-phenyl; 2-bromo-4,5-bis-difluoromethoxy-phenyl; 2-bromo-4-fluoro-5-(2-methoxyethoxy)-phenyl; 2-bromo-4-fluoro-5-(2-hydroxyethoxy)-phenyl; 4-fluoro-4,5-dimethoxy-phenyl; 2,4-dimethylphenyl; 3,5-dimethylphenyl; 4,5-dimethoxy-2-morpholin-4-yl-phenyl; 3-methoxy-2-methyl-phenyl; 2,3-dimethoxy-phenyl; 4-fluoro-5-(2-hydroxy-ethoxy)-2-methyl-phenyl; 4-chloro-4-(3-hydroxy-propyl)-2-methyl-phenyl; 2-dimethylamino-4,5-dimethoxy-phenyl; 4-chloro-5-hydroxymethyl-2-methyl-phenyl; 2-bromo-4-trifluoromethoxy-phenyl; 2-bromo-4-chloro-5-dimethylaminocarbonylmethoxy-phenyl; 4-chloro-5-{[(2-methoxy-ethyl)-methyl-amino]-methyl}-2-methyl-phenyl; 5-(tert-butoxycarbonylaminomethyl)-2-methyl-4-chloro-phenyl; 5-aminomethyl-4-chloro-2-methyl-phenyl; 4-chloro-2-methyl-5-(methylcarbonylaminomethyl)-phenyl; 5-{[bis-(2-hydroxy-ethyl)-amino]-methyl}-4-chloro-2-methyl-phenyl; 4-chloro-2-methyl-5-morpholin-4-ylmethyl-phenyl; 3-methyl-phenyl; 4-chloro-5-(2-hydroxy-ethyl)-2-methyl-phenyl; 2-bromo-3,4-ethylenedioxy-phenyl (7-bromo-2,3-dihydro-benzo[1,4]dioxin-6-yl)); 3-chloro-2-methyl-phenyl; 3-hydroxymethyl-2-methyl-phenyl; 2-methyl-3-methylaminocarbonyl-phenyl; 4-chloro-2-methyl-5-(piperidin-4-yloxy)-phenyl; 2-methyl-3-(tert-butoxycarbonylmethyl)-phenyl; 3-(2-hydroxy-ethyl)-2-methyl-phenyl; 4,5-difluoro-2-methyl-phenyl; 2-bromo-4,5-difluoro-phenyl; 3,4-dimethyl-phenyl; 2-chloro-3-methyl-phenyl; 2-bromo-4-(2-hydroxy-ethyl)-phenyl; 2-bromo-4-isopropyl-phenyl; 3-fluoro-2-methyl-phenyl; 2-bromo-5-(2-hydroxy-ethoxy)-4-methyl-phenyl; 2-(2-hydroxy-ethyl)-4,5-dimethoxy-phenyl; 4-chloro-5-dimethylaminomethyl-2-methyl-phenyl; 2-ethyl-phenyl; 2-propyl-phenyl; 5-methoxy-2,3-dimethyl-phenyl; and 3-(hydroxycarbonylmethyl)-2-methyl-phenyl.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2,4-dichloro-5-methoxy-phenyl; 2-bromo-5-methoxy-4-trifluoromethyl-phenyl; 2-bromo-4,5-dichloro-phenyl; 2-bromo-4-chloro-5-iodo-phenyl; 2-bromo-4-chloro-5-trifluoromethyl-phenyl; 2-bromo-5-methoxy-4-methyl-phenyl; 2-isopropyl-4,5-dimethoxy-phenyl; 2-bromo-4-chloro-5-methanesulfanyl-phenyl; 2-bromo-4-chloro-5-methanesulfonyl-phenyl; 2-bromo-4-chloro-5-methanesulfinyl-phenyl; 2-bromo-4-chloro-5-fluoro-phenyl; 2-bromo-5-methoxy-phenyl; 2-bromo-5-methoxy-4-methoxycarbonyl-phenyl; 2-bromo-4-chloro-5-hydroxy-phenyl; 2-bromo-4-chloro-5-(methylamino-carbonyl-methyoxy)-phenyl; 2-methyl-4,5-dimethoxy-phenyl; 2-bromo-4-chloro-5-methoxycarbonyl-phenyl; 2-bromo-4-methanesulfonyl-5-methoxy-phenyl; 2-bromo-4-methyl-5-methoxy-phenyl; 2-bromo-4-chloro-5-(methoxycarbonyl-methoxy)-phenyl; 2-bromo-4-chloro-5-(hydroxycarbonyl-methoxy)-phenyl; 2-bromo-4-chloro-5-(2-methoxyethoxy)-phenyl; 4,5-dimethoxy-phenyl; 2-fluoro-4-chloro-5-methoxy-phenyl; 2-bromo-4-methoxycarbonyl-5-methoxy-phenyl; 6-bromo-benzo[1,3]dioxol-5-yl; 2-bromo-4-chloro-5-(2-hydroxyethoxy)-phenyl; 2-bromo-4-difluoromethoxy-5-methoxy-phenyl; 5-methoxy-4-methyl-phenyl; 2-bromo-4-chloro-5-(2-methylamino-ethoxy)-phenyl; 2-bromo-4-cyano-5-methyl-phenyl; 2-bromo-4-methyl-5-methoxy-phenyl; 2-bromo-4-chloro-5-acetyl-phenyl; 5-methoxy-2-methyl-phenyl; 2-bromo-4-chloro-5-(3-methanesulfonyl-propoxy)-phenyl; 2-bromo-5-methoxy-4-(tert-butoxycarbonyl)-phenyl; 5-methanesulfonyl-2-methoxy-phenyl; 2-bromo-4-chloro-5-(1-hydroxyethyl)-phenyl; 2-fluoro-5-(2-hydroxyethoxy)-4-methyl-phenyl; 2-bromo-5-methoxy-4-aminocarbonyl-phenyl; 6-bromo-2,2-difluoro-benzo[1,3]dioxol-5-yl; 2,6-difluoro-phenyl; 2-bromo-4-cyano-5-methoxy-phenyl; 2,5-dimethoxy-phenyl; 3-methoxycarbonyl-2-methyl-phenyl; 3-methoxy-phenyl; 4-methoxy-phenyl; 2,4-dimethoxy-phenyl; 4-chloro-5-methoxy-phenyl; 4-fluoro-5-methoxy-phenyl; 2-bromo-4-methyl-5-(tert-butoxycarbonyl)-phenyl; 3,4,5-trimethoxy-phenyl; 2-bromo-4,6-difluoro-phenyl; 2-ethyl-4,5-dimethoxy-phenyl; 2-bromo-4-methoxy-phenyl; 4-chloro-5-(2-hydroxyethoxy)-2-methyl-phenyl; 3-methoxycarbonyl-2-methyl-phenyl; 2,5-dimethyl-phenyl; 2-bromo-5-methoxy-phenyl; 2,3-dimethyl-phenyl; 2-bromo-4-chloro-5-hydroxymethyl-phenyl; 2-bromo-3,5-dimethyl-phenyl; 4-methoxy-2-methyl-phenyl; or 2,4-dimethyl-phenyl.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2-bromo-5-methoxy-4-methyl-phenyl; 2-methyl-4,5-dimethoxy-phenyl; 2-bromo-4-chloro-5-(2-methoxy-ethyl-phenyl; 2-bromo-4-chloro-5-(2-hydroxy-ethyl-phenyl; 2-bromo-4-difluoromethoxy-5-methoxy-phenyl; 2,5-dimethoxy-phenyl; 2-ethyl-4,5-dimethoxy-phenyl; 2-methyl-5-(2-hydroxy-ethoxy)-4-chloro-phenyl; 2,5-dimethyl-phenyl; 2-bromo-5-methoxy-phenyl; or 2-bromo-4,5-dimethyl-phenyl.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2-bromo-5-methoxy-4-methyl-phenyl; 4,5-dimethoxy-2-methyl-phenyl; 2-bromo-4,5-methylenedioxy-phenyl (6-bromo-benzo[1,3]dioxol-5-yl); 2-bromo-4-chloro-5-(2-hydroxy-ethoxy)-phenyl; 2-bromo-4-difluoromethoxy-5-methoxy-phenyl; 5-methoxy-2-methyl-phenyl; 2-bromo-4-chloro-5-(1-hydroxy-ethyl)-phenyl; 2-bromo-4-chloro-5-((S)-1-hydroxy-ethyl)-phenyl; 2-ethyl-4,5-dimethoxy-phenyl; 2-bromo-4-methoxy-phenyl; 4-chloro-5-(2-hydroxy-ethoxy)-2-methyl-phenyl; 2,5-dimethyl-phenyl; 2-bromo-5-methoxy-phenyl; 2,3-dimethyl-phenyl; 2-bromo-4-chloro-5-hydroxymethylphenyl; 2-bromo-3,5-dimethyl-phenyl; 2,4-dimethyl-phenyl; 3-methoxy-2-methyl-phenyl; 4-fluoro-5-(2-hydroxy-ethoxy)-2-methyl-phenyl; 4-chloro-5-(3-hydroxy-propoxy)-2-methyl-phenyl; 4-chloro-5-hydroxymethyl-2-methyl-phenyl; 5-{[bis-(2-hydroxy-ethyl)-amino]-methyl}-4-chloro-2-methyl-phenyl; 4-chloro-5-(2-hydroxy-ethyl)-2-methyl-phenyl; 2-bromo-4,5-ethylenedioxy-phenyl (7-bromo-2,3-dihydro-benzo[1,4]dioxin-6-yl); 3-chloro-2-methyl-phenyl; 3-hydroxymethyl-2-methyl-phenyl; or 3-(2-hydroxy-ethyl)-2-methyl-phenyl.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2-bromo-5-methoxy-4-methyl-phenyl; 2-methyl-4,5-dimethoxy-phenyl; 2-bromo-4-chloro-5-(2-methoxy-ethyl-phenyl; 2-bromo-4-chloro-5-(2-hydroxy-ethyl-phenyl; 2-bromo-4-difluoromethoxy-5-methoxy-phenyl; 2,5-dimethoxy-phenyl; 2-ethyl-4,5-dimethoxy-phenyl; 2-methyl-5-(2-hydroxy-ethoxy)-4-chloro-phenyl; 2,5-dimethyl-phenyl; 2-bromo-5-methoxy-phenyl; 2-bromo-4,5-dimethyl-phenyl; 2-methyl-5-(5-methyl-1H-pyrazol-3-yl)-phenyl; 2-methyl-5-(4-methyl-pyrazol-1-yl)-phenyl; 2-methyl-5-(5-methyl-1H-pyrazol-3-yl)-phenyl; 5-(4,5-dimethyl-4H-[1,2,4]triazol-3-yl)-2-methyl-phenyl; 5-[1-(2,3-dihydroxy-propyl)-5-methyl-1H-pyrazol-3-yl]-2-methyl-phenyl; 2-methyl-5-(2-methyl-3-oxo-2,3-dihydro-pyridazin-4-yl)-phenyl; 2-methyl-3-(2H-pyrazol-3-yl)-phenyl; 5-[1-(2-hydroxy-3-methoxy-propyl)-5-methyl-1H-pyrazol-3-yl]-2-methyl-phenyl; 5-[4-(2-hydroxy-3-methoxy-propyl)-3,5-dioxo-4,5-dihydro-3H-[1,2,4]triazin-2-yl]-2-methyl-phenyl; 2-methyl-5-(4-methyl-3,5-dioxo-4,5-dihydro-3H-[1,2,4]triazin-2-yl)-phenyl; 2-methyl-5-(6-oxo-6H-pyridazin-1-yl)-phenyl; 2-methyl-5-(3-methyl-6-oxo-6H-pyridazin-1-yl)-phenyl; 2-methyl-5-(6-oxo-1,6-dihydro-pyrazin-2-yl)-phenyl; 2-methyl-5-(3-oxo-2,3-dihydro-pyridazin-4-yl)-phenyl; 5-(2-ethyl-3-oxo-2,3-dihydro-pyridazin-4-yl)-2-methyl-phenyl; 2-methyl-5-(1-methyl-6-oxo-1,6-dihydro-pyridazin-3-yl)-phenyl; 2-methyl-5-(6-oxo-1,6-dihydro-pyridazin-3-yl)-phenyl; 5-[2-(2-hydroxy-3-methoxy-propyl)-3-oxo-2,3-dihydro-pyridazin-4-yl]-2-methyl-phenyl; 2-methyl-5-(2-methyl-3-oxo-2,3-dihydro-pyridazin-4-yl)-phenyl; 2-bromo-5-(2-oxo-pyrrolidin-1-yl)-phenyl; 5-(2,4-dioxo-3,4-dihydro-2H-pyrimidin-1-yl)-2-methyl-phenyl; 2-methyl-5-(6-oxo-6H-pyridazin-1-yl)-phenyl; 2-methyl-5-(3-methyl-2-oxo-2H-pyridin-1-yl)-phenyl; 2-methyl-5-(2-methyl-3-oxo-2,3-dihydro-pyridazin-4-yl)-phenyl; 2-methyl-5-(2-oxo-2H-pyridin-1-yl)-phenyl; 5-(6-methoxy-pyridazin-3-yl)-2-methyl-phenyl; 5-(2,6-dioxo-3,6-dihydro-2H-pyrimidin-1-yl)-2-methyl-phenyl; 5-[1-(2-hydroxy-ethyl)-6-oxo-1,6-dihydro-pyridazin-3-yl]-2-methyl-phenyl; 2-methyl-5-(1-methyl-2-oxo-1,2-dihydro-pyridin-3-yl)-phenyl; 5-[1-(2-hydroxy-3-methoxy-propyl)-6-oxo-1,6-dihydro-pyridazin-3-yl]-2-methyl-phenyl; 4-chloro-2-methyl-5-(6-oxo-6H-pyridazin-1-yl)-phenyl; 5-(4-ethyl-3,5-dioxo-4,5-dihydro-3H-[1,2,4]triazin-2-yl)-2-methyl-phenyl; 4-chloro-2-methyl-5-(3-methyl-2-oxo-2H-pyridin-1-yl)-phenyl; 2-methyl-5-(4-methyl-6-oxo-6H-pyridazin-1-yl)-phenyl; 2-methyl-5-(3-methyl-2,4-dioxo-3,4-dihydro-2H-pyrimidin-1-yl)-phenyl; 4-fluoro-2-methyl-5-(6-oxo-6H-pyridazin-1-yl)-phenyl; 4-fluoro-2-methyl-5-(1-methyl-2-oxo-1,2-dihydro-pyridin-3-yl)-phenyl; 2-methyl-5-(5-methyl-2-oxo-2H-pyridin-1-yl)-phenyl; 2-methyl-3-oxo-2,3-dihydro-pyridazin-4-yl)-phenyl; 4-fluoro-2-methyl-5-(4-methyl-6-oxo-6H-pyridazin-1-yl)-phenyl; 2-fluoro-5-(6-oxo-6H-pyridazin-1-yl)-phenyl; 3-fluoro-2-methyl-5-(6-oxo-6H-pyridazin-1-yl)-phenyl; or 4-fluoro-2-methyl-5-(1-methyl-6-oxo-1,6-dihydro-pyridin-3-yl)-phenyl.

In certain embodiments of formula I, $R^1$ is: 4,5-dimethoxy-2-methyl-phenyl; 2-methyl-5-(5-methyl-1H-pyrazol-3-yl; 4-chloro-5-(2-hydroxy-ethoxy)-2-methyl-phenyl; 4-fluoro-5-(2-hydroxy-ethoxy)-2-methyl-phenyl; 5-(4,5-dimethyl-4H-[1,2,4]triazol-3-yl)-2-methyl-phenyl; 5-[1-((R)-2,3-dihydroxy-propyl)-5-methyl-1H-pyrazol-3-yl]-2-methyl-phenyl; 2-methyl-5-(2-methyl-3-oxo-2,3-dihydro-pyridazin-4-yl)-phenyl; 5-[1-((R)-2-hydroxy-3-methoxy-propyl)-5-methyl-1H-pyrazol-3-yl]-2-methyl-phenyl; 5-[4-((R)-2-hydroxy-3-methoxy-propyl)-3,5-dioxo-4,5-dihydro-3H-[1,2,4]triazin-2-yl]-2-methyl-phenyl; 2-methyl-5-(6-oxo-6H-pyridazin-1-yl)-phenyl; 2-methyl-5-(3-methyl-6-oxo-6H-pyridazin-1-yl)-phenyl; 2-methyl-5-(6-oxo-1,6-dihydro-pyrazin-2-yl)-phenyl; 2-methyl-5-(3-oxo-2,3-dihydro-pyridazin-4-yl)-phenyl; 2-methyl-5-(4-methyl-3,5-dioxo-4,5-dihydro-3H-[1,2,4]triazin-2-yl)-phenyl; 5-[1-((S)-2-hydroxy-3-methoxy-propyl)-5-methyl-1H-pyrazol-3-yl]-2-methyl-phenyl; 2-methyl-5-(4-methyl-3,5-dioxo-4,5-dihydro-3H-[1,2,4]triazin-2-yl)-phenyl; 5-(2-ethyl-3-oxo-2,3-dihydro-pyridazin-4-yl)-2-methyl-phenyl; 2-methyl-5-(1-methyl-6-oxo-1,6-dihydro-pyridazin-3-yl; 2-methyl-5-(6-oxo-1,6-dihydro-pyridazin-3-yl)-phenyl; 5-[2-((R)-2-hydroxy-3-methoxy-propyl)-3-oxo-2,3-dihydro-pyridazin-4-yl]-2-methyl-phenyl; 2-bromo-5-(2-oxo-pyrrolidin-1-yl; 5-(2,4-dioxo-3,4-dihydro-2H-pyrimidin-1-yl)-2-methyl-phenyl; 2-methyl-5-(3-methyl-2-oxo-2H-pyridin-1-yl)-phenyl; 2-methyl-5-(2-oxo-2H-pyridin-1-yl)-phenyl; 5-(6-methoxy-pyridazin-3-yl)-2-methyl-phenyl; 5-(2,6-dioxo-3,6-dihydro-2H-pyrimidin-1-yl)-2-methyl-phenyl; 5-[1-(2-hydroxy-ethyl)-6-oxo-1,6-dihydro-pyridazin-3-yl]-2-methyl-phenyl; 2-methyl-5-(1-methyl-2-oxo-1,2-dihydro-pyridin-3-yl)-phenyl; 5-[1-((R)-2-hydroxy-3-methoxy-propyl)-6-oxo-1,6-dihydro-pyridazin-3-yl]-2-methyl-phenyl; 4-chloro-2-methyl-5-(6-oxo-6H-pyridazin-1-yl)-phenyl; 5-(4-ethyl-3,5-dioxo-4,5-dihydro-3H-[1,2,4]triazin-2-yl)-2-methyl-phenyl; 4-chloro-2-methyl-5-(3-methyl-2-oxo-2H-pyridin-1-yl)-phenyl; 2-methyl-5-(4-methyl-6-oxo-6H-pyridazin-1-yl)-phenyl; 2-methyl-5-(3-methyl-2,4-dioxo-3,4-dihydro-2H-pyrimidin-1-yl)-phenyl; 4-fluoro-2-methyl-5-(6-oxo-6H-pyridazin-1-yl)-phenyl; 4-fluoro-2-methyl-5-(1-methyl-2-oxo-1,2-dihydro-pyridin-3-yl)-phenyl; 2-methyl-5-(5-methyl-2-oxo-2H-pyridin-1-yl)-phenyl; 2-methyl-3-oxo-2,3-dihydro-pyridazin-4-yl)-phenyl; 4-fluoro-2-methyl-5-(4-methyl-6-oxo-6H-pyridazin-1-yl)-phenyl; 2-fluoro-5-(6-oxo-6H-pyridazin-1-yl)-phenyl; 3-fluoro-2-methyl-5-(6-oxo-6H-pyridazin-1-yl)-phenyl; or 4-fluoro-2-methyl-5-(1-methyl-6-oxo-1,6-dihydro-pyridin-3-yl)-phenyl.

In certain embodiments of formula I, $R^1$ is 2-bromo-4,5-dimethoxy-phenyl.

In certain embodiments of formula I, $R^1$ is 2-bromo-4-chloro-5-methoxy-phenyl.

In certain embodiments of formula I, $R^1$ is 2-bromo-4-fluoro-5-methoxy-phenyl.

In certain embodiments of formula I, $R^1$ is 2-bromo-5-methoxy-4-methyl-phenyl.

In certain embodiments of formula I, $R^1$ is 2-methyl-4,5-dimethoxy-phenyl.

In certain embodiments of formula I, $R^1$ is 2-bromo-4-chloro-5-(2-methoxy-ethyl-phenyl.

In certain embodiments of formula I, $R^1$ is 2-bromo-4-chloro-5-(2-hydroxy-ethyl-phenyl.

In certain embodiments of formula I, $R^1$ is 2-bromo-4-difluoromethoxy-5-methoxy-phenyl.

In certain embodiments of formula I, $R^1$ is 2,5-dimethoxy-phenyl.

In certain embodiments of formula I, $R^1$ is 2-ethyl-4,5-dimethoxy-phenyl.

In certain embodiments of formula I, $R^1$ is 2-methyl-5-(2-hydroxy-ethoxy)-4-chloro-phenyl.

In certain embodiments of formula I, $R^1$ is 2,5-dimethyl-phenyl.

In certain embodiments of formula I, $R^1$ is 2-bromo-5-methoxy-phenyl.

In certain embodiments of formula I, $R^1$ is 2-bromo-4,5-dimethyl-phenyl.

In certain embodiments of formula I, $R^1$ is 2-methyl-5-(5-methyl-1H-pyrazol-3-yl)-phenyl.

In certain embodiments of formula I, $R^1$ is 2-methyl-5-(4-methyl-pyrazol-1-yl)-phenyl.

In certain embodiments of formula I, $R^1$ is 2-methyl-5-(5-methyl-1H-pyrazol-3-yl)-phenyl.

In certain embodiments of formula I, $R^1$ is 5-(4,5-dimethyl-4H-[1,2,4]triazol-3-yl)-2-methyl-phenyl.

In certain embodiments of formula I, $R^1$ is 5-[1-(2,3-dihydroxy-propyl)-5-methyl-1H-pyrazol-3-yl]-2-methyl-phenyl.

In certain embodiments of formula I, $R^1$ is 2-methyl-5-(2-methyl-3-oxo-2,3-dihydro-pyridazin-4-yl)-phenyl.

In certain embodiments of formula I, $R^1$ is 2-methyl-3-(2H-pyrazol-3-yl)-phenyl.

In certain embodiments of formula I, $R^1$ is 5-[1-(2-hydroxy-3-methoxy-propyl)-5-methyl-1H-pyrazol-3-yl]-2-methyl-phenyl.

In certain embodiments of formula I, $R^1$ is 5-[4-(2-hydroxy-3-methoxy-propyl)-3,5-dioxo-4,5-dihydro-3H-[1,2,4]triazin-2-yl]-2-methyl-phenyl.

In certain embodiments of formula I, $R^1$ is 2-methyl-5-(4-methyl-3,5-dioxo-4,5-dihydro-3H-[1,2,4]triazin-2-yl)-phenyl.

In certain embodiments of formula I, $R^1$ is 2-methyl-5-(6-oxo-6H-pyridazin-1-yl)-phenyl.

In certain embodiments of formula I, $R^1$ is 2-methyl-5-(3-methyl-6-oxo-6H-pyridazin-1-yl)-phenyl.

In certain embodiments of formula I, $R^1$ is 2-methyl-5-(6-oxo-1,6-dihydro-pyrazin-2-yl)-phenyl.

In certain embodiments of formula I, $R^1$ is 2-methyl-5-(3-oxo-2,3-dihydro-pyridazin-4-yl)-phenyl.

In certain embodiments of formula I, $R^1$ is 5-(2-ethyl-3-oxo-2,3-dihydro-pyridazin-4-yl)-2-methyl-phenyl.

In certain embodiments of formula I, $R^1$ is 2-methyl-5-(1-methyl-6-oxo-1,6-dihydro-pyridazin-3-yl)-phenyl.

In certain embodiments of formula I, $R^1$ is 2-methyl-5-(6-oxo-1,6-dihydro-pyridazin-3-yl)-phenyl.

In certain embodiments of formula I, $R^1$ is 5-[2-(2-hydroxy-3-methoxy-propyl)-3-oxo-2,3-dihydro-pyridazin-4-yl]-2-methyl-phenyl.

In certain embodiments of formula I, $R^1$ is 2-methyl-5-(2-methyl-3-oxo-2,3-dihydro-pyridazin-4-yl)-phenyl.

In certain embodiments of formula I, $R^1$ is 2-bromo-5-(2-oxo-pyrrolidin-1-yl)-phenyl.

In certain embodiments of formula I, $R^1$ is 5-(2,4-dioxo-3,4-dihydro-2H-pyrimidin-1-yl)-2-methyl-phenyl.

In certain embodiments of formula I, $R^1$ is 2-methyl-5-(6-oxo-6H-pyridazin-1-yl)-phenyl.

In certain embodiments of formula I, $R^1$ is 2-methyl-5-(3-methyl-2-oxo-2H-pyridin-1-yl)-phenyl.

In certain embodiments of formula I, $R^1$ is 2-methyl-5-(2-methyl-3-oxo-2,3-dihydro-pyridazin-4-yl)-phenyl.

In certain embodiments of formula I, $R^1$ is 2-methyl-5-(2-oxo-2H-pyridin-1-yl)-phenyl.

In certain embodiments of formula I, $R^1$ is 5-(6-methoxy-pyridazin-3-yl)-2-methyl-phenyl.

In certain embodiments of formula I, $R^1$ is 5-(2,6-dioxo-3,6-dihydro-2H-pyrimidin-1-yl)-2-methyl-phenyl.

In certain embodiments of formula I, $R^1$ is 5-[1-(2-hydroxy-ethyl)-6-oxo-1,6-dihydro-pyridazin-3-yl]-2-methyl-phenyl.

In certain embodiments of formula I, $R^1$ is 2-methyl-5-(1-methyl-2-oxo-1,2-dihydro-pyridin-3-yl)-phenyl.

In certain embodiments of formula I, $R^1$ is 5-[1-(2-hydroxy-3-methoxy-propyl)-6-oxo-1,6-dihydro-pyridazin-3-yl]-2-methyl-phenyl.

In certain embodiments of formula I, $R^1$ is 4-chloro-2-methyl-5-(6-oxo-6H-pyridazin-1-yl)-phenyl.

In certain embodiments of formula I, $R^1$ is 5-(4-ethyl-3,5-dioxo-4,5-dihydro-3H-[1,2,4]triazin-2-yl)-2-methyl-phenyl.

In certain embodiments of formula I, $R^1$ is 4-chloro-2-methyl-5-(3-methyl-2-oxo-2H-pyridin-1-yl)-phenyl.

In certain embodiments of formula I, $R^1$ is 2-methyl-5-(4-methyl-6-oxo-6H-pyridazin-1-yl)-phenyl.

In certain embodiments of formula I, $R^1$ is 2-methyl-5-(3-methyl-2,4-dioxo-3,4-dihydro-2H-pyrimidin-1-yl)-phenyl.

In certain embodiments of formula I, $R^1$ is 4-fluoro-2-methyl-5-(6-oxo-6H-pyridazin-1-yl)-phenyl.

In certain embodiments of formula I, $R^1$ is 4-fluoro-2-methyl-5-(1-methyl-2-oxo-1,2-dihydro-pyridin-3-yl)-phenyl.

In certain embodiments of formula I, $R^1$ is 2-methyl-5-(5-methyl-2-oxo-2H-pyridin-1-yl)-phenyl.

In certain embodiments of formula I, $R^1$ is 2-methyl-3-oxo-2,3-dihydro-pyridazin-4-yl)-phenyl.

In certain embodiments of formula I, $R^1$ is 4-fluoro-2-methyl-5-(4-methyl-6-oxo-6H-pyridazin-1-yl)-phenyl.

In certain embodiments of formula I, $R^1$ is 2-fluoro-5-(6-oxo-6H-pyridazin-1-yl)-phenyl.

In certain embodiments of formula I, $R^1$ is 3-fluoro-2-methyl-5-(6-oxo-6H-pyridazin-1-yl)-phenyl.

In certain embodiments of formula I, $R^1$ is 4-fluoro-2-methyl-5-(1-methyl-6-oxo-1,6-dihydro-pyridin-3-yl)-phenyl.

In certain embodiments of formula I, $R^1$ is phenyl substituted one, two or three times with a substituent or substituents each independently selected from: $C_{1-6}$alkyl; $C_{1-6}$alkoxy; halo; hydroxy-$C_{1-6}$alkoxy; or a five- or six-membered heteroaryl selected from: pyrrolyl; pyrazolyl; triazolyl; oxazolyl; isoxazolyl; thiazolyl; isothiazolyl; thiadiazolyl; oxadiazolyl; oxazolidinyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkoxy; hydroxy-$C_{1-6}$alkyl; $C_{1-6}$alkoxy-$C_{1-6}$alkyl; or hydroxy-$C_{1-6}$alkoxy-$C_{1-6}$alkyl.

In certain embodiments of formula I, $R^1$ is phenyl substituted one, two or three times with a substituent or substituents each independently selected from: $C_{1-6}$alkyl; $C_{1-6}$alkoxy; halo; hydroxy-$C_{1-6}$alkoxy; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkoxy; hydroxy-$C_{1-6}$alkyl; $C_{1-6}$alkoxy-$C_{1-6}$alkyl; or hydroxy-$C_{1-6}$alkoxy-$C_{1-6}$alkyl.

In certain embodiments of formula I, $R^1$ is phenyl substituted one, two or three times with a substituent or substituents each independently selected from: $C_{1-6}$alkyl; $C_{1-6}$alkoxy; halo; hydroxy-$C_{1-6}$alkoxy; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of formula I, $R^1$ is phenyl substituted one, two or three times with a substituent or substituents each independently selected from: methyl; methoxy, chloro; bromo; 2-hydroxy-ethoxy; 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

In certain embodiments of formula I, $R^1$ is phenyl substituted:

at the 2-position with: $C_{1-6}$alkyl; or halo;
at the 4-position with: hydrogen; $C_{1-6}$alkoxy; or halo; and
at the 5-position with: $C_{1-6}$alkoxy; hydroxy-$C_{1-6}$alkoxy; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of formula I, $R^1$ is phenyl substituted:

at the 2-position with: methyl; halo; or bromo;
at the 4-position with: hydrogen; methoxy; fluoro; or chloro; and
at the 5-position with: methoxy; hydroxy-ethoxy; 5-methyl-1H-pyrazol-3-yl; 4-methyl-pyrazol-1-yl; 4,5-dimethyl-4H-[1,2,4]triazol-3-yl); 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

In certain embodiments of formula I, $R^1$ is optionally substituted heteroaryl;

In certain embodiments of formula I, $R^1$ is: quinolinyl; isoquinolinyl; indolyl; or indazolyl; each optionally substituted once or twice with a group or groups independently selected from: $C_{1-6}$alkyl; $C_{1-6}$alkoxy; hydroxy-$C_{1-6}$alkyl; halo; and oxo.

In certain embodiments of formula I, $R^1$ is: quinolinyl; isoquinolinyl; or indolyl; each optionally substituted once or twice with a group or groups independently selected from: $C_{1-6}$alkyl; $C_{1-6}$alkoxy; hydroxy-$C_{1-6}$alkyl; halo; and oxo.

In certain embodiments of formula I, $R^1$ is: quinolinyl; isoquinolinyl; or indazolyl; each substituted once or twice with a group or groups independently selected from: $C_{1-6}$alkyl; hydroxy-$C_{1-6}$alkyl; and oxo.

In certain embodiments of formula I, $R^1$ is: quinolinyl; or isoquinolinyl; each substituted once or twice with a group or groups independently selected from: $C_{1-6}$alkyl; hydroxy-$C_{1-6}$alkyl; and oxo.

In certain embodiments of formula I, $R^1$ is: quinolinyl optionally substituted once or twice with a group or groups independently selected from: $C_{1-6}$alkyl; $C_{1-6}$alkoxy; hydroxy-$C_{1-6}$alkyl; halo; and oxo.

In certain embodiments of formula I, $R^1$ is isoquinolinyl optionally substituted once or twice with a group or groups independently selected from: $C_{1-6}$alkyl; $C_{1-6}$alkoxy; hydroxy-$C_{1-6}$alkyl; halo; and oxo.

In certain embodiments of formula I, $R^1$ is indolyl optionally substituted once or twice with a group or groups independently selected from: $C_{1-6}$alkyl; $C_{1-6}$alkoxy; hydroxy-$C_{1-6}$ alkyl; halo; and oxo.

In certain embodiments of formula I, $R^1$ is indazolyl optionally substituted once or twice with a group or groups independently selected from: $C_{1-6}$alkyl; $C_{1-6}$alkoxy; hydroxy-$C_{1-6}$alkyl; halo; and oxo.

In certain embodiments of formula I, $R^1$ is: 6-methyl-quinolin-5-yl; 2,6-dimethyl-quinolin-5-yl; 6-methyl-2-oxo-1,2-dihydro-quinolin-5-y; 5-ethyl-2-methyl-quinolin-6-yl; 1-(2-hydroxy-ethyl)-5-methyl-1H-indazol-6-yl; 1,5-dimethyl-1H-indazol-6-yl; 2-methyl-1-oxo-1,2-dihydro-isoquinolin-5-yl; or 2-methyl-1-oxo-1,2-dihydro-isoquinolin-5-yl.

In certain embodiments of formula I, $R^2$ is optionally substituted phenyl.

In certain embodiments of formula I, $R^2$ is phenyl optionally substituted one, two, three or four times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfony-$C_{1-6}$alkoxy; hydroxy-$C_{1-6}$alkyl; $C_{3-6}$cycloalkyl-$C_{1-6}$alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonyl$C_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$alkyl; or nitro; or two adjacent substituents may form a $C_{1-2}$alkylenedioxy or halo-$C_{1-2}$alkylenedioxy.

In certain embodiments of formula I, $R^2$ is phenyl optionally substituted once or twice with a substituent or substituents each independently selected from: fluoro; chloro; bromo; iodo; methyl; ethyl; methoxy; ethoxy; trifluoromethyl; difluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; or two adjacent substituents may form methylenedioxy, ethylenedioxy or difluoromethylenedioxy.

In certain embodiments of formula I, $R^2$ is phenyl substituted once or twice with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; alkoxyalkoxy; hydroxyalkoxy; alkylsulfonylalkoxy; hydroxyalkyl; or $C_{3-6}$cycloalkyl-$C_{1-6}$alkoxy.

In certain embodiments of formula I, $R^2$ is phenyl optionally substituted once or twice with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; or cyclopropylmethoxy.

In certain embodiments of formula I, $R^2$ is phenyl substituted once or twice with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, $R^2$ is phenyl substituted once or twice with a substituent or substituents each independently selected from: halo; methyl; methoxy; trifluoromethyl; difluoromethoxy; nitrile; or methanesulfonyl.

In certain embodiments of formula I, $R^2$ is phenyl substituted once or twice with a substituent or substituents each independently selected from: fluoro; chloro; methyl; methoxy; or nitrile.

In certain embodiments of formula I, $R^2$ is phenyl substituted once or twice with fluoro.

In certain embodiments of formula I, $R^2$ is: phenyl; 4-fluoro-phenyl; 3-fluoro-phenyl; 2-fluoro-phenyl; 2-chloro-phenyl; 3,4-difluoro-phenyl; 3,5-difluoro-phenyl; 3-methyl-phenyl; 4-methyl-phenyl; or 3-cyano-phenyl.

In certain embodiments of formula I, $R^2$ is: phenyl; 4-fluoro-phenyl; 3-fluoro-phenyl; 2-fluoro-phenyl; 2-chloro-phenyl; 3,4-difluoro-phenyl; or 3,5-difluoro-phenyl.

In certain embodiments of formula I, $R^2$ is 4-fluoro-phenyl.
In certain embodiments of formula I, $R^2$ is 3-fluoro-phenyl.
In certain embodiments of formula I, $R^2$ is 3,4-difluoro-phenyl.

In certain embodiments of formula I, $R^2$ is optionally substituted $C_{3-6}$cycloalkyl.

In certain embodiments of formula I, $R^2$ is $C_{3-6}$cycloalkyl optionally substituted with halo.

In certain embodiments of formula I, $R^2$ is cyclohexyl.

In certain embodiments of formula I, $R^2$ is cyclohexyl optionally substituted once or twice with halo.

In certain embodiments of formula I, $R^2$ is cyclohexyl optionally substituted once or twice with fluoro.

In certain embodiments of formula I, $R^a$ is hydrogen or $C_{1-6}$alkyl.

In certain embodiments of formula I, $R^a$ is hydrogen.
In certain embodiments of formula I, $R^a$ is $C_{1-6}$alkyl.
In certain embodiments of formula I, $R^a$ is methyl.
In certain embodiments of formula I, $R^a$ is ethyl.
In certain embodiments of formula I, $R^a$ is hydroxy-$C_{1-6}$alkyl.
In certain embodiments of formula I, $R^a$ is hydroxy-ethyl.
In certain embodiments of formula I, $R^a$ is $C_{1-6}$alkoxy-$C_{1-6}$alkyl.
In certain embodiments of formula I, $R^a$ is methoxy-ethyl.
In certain embodiments of formula I, $R^a$ is hydroxy-$C_{1-6}$alkoxy-$C_{1-6}$alkyl.
In certain embodiments of formula I, $R^a$ is $C_{1-6}$alkylcarbonyl.
In certain embodiments of formula I, $R^a$ is $C_{1-6}$alkylsulfonyl-$C_{1-6}$alkyl.
In certain embodiments of formula I, $R^a$ is aminocarbonyl-$C_{1-6}$alkyl.
In certain embodiments of formula I, $R^b$ is hydrogen.
In certain embodiments of formula I, $R^b$ is $C_{1-6}$alkyl.
In certain embodiments of formula I, $R^b$ is methyl.

In certain embodiments, the compounds of formula I may be more specifically of formula II:

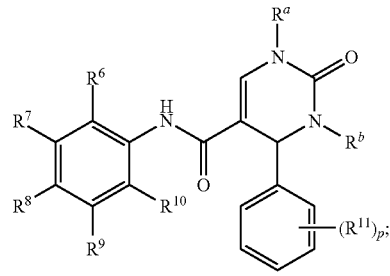

wherein:
p is from 0 to 3;
$R^6$, $R^7$, $R^8$, $R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfony-$C_{1-6}$alkoxy; hydroxy-$C_{1-6}$alkyl; $C_{3-6}$cycloalkyl-$C_{1-6}$alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonyl$C_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$alkyl; or nitro; or two adjacent substituents may form a $C_{1-2}$alkylenedioxy; halo-$C_{1-2}$alkylenedioxy; or a five- or six-membered heteroaryl selected from: pyrrolyl; pyrazolyl; triazolyl; oxazolyl; isoxazolyl; thiazolyl; isothiazolyl; thiadiazolyl; oxadiazolyl; oxazolidinyl; pyridinyl; pyrimidinyl; pyrazinyl; pyridazinyl; or triazinyl, each optionally substituted;

each $R^{11}$ independently is: halo; $C_{1-6}$alkyl; $C_{1-6}$alkoxy; halo-$C_{1-6}$alkyl; halo-$C_{1-6}$alkoxy; $C_{1-6}$alkylsulfonyl; or nitrile; and $R^a$ and $R^b$ are as defined herein.

In certain embodiments of formula II, the subject compounds may be more specifically of formula IIa or formula IIb;

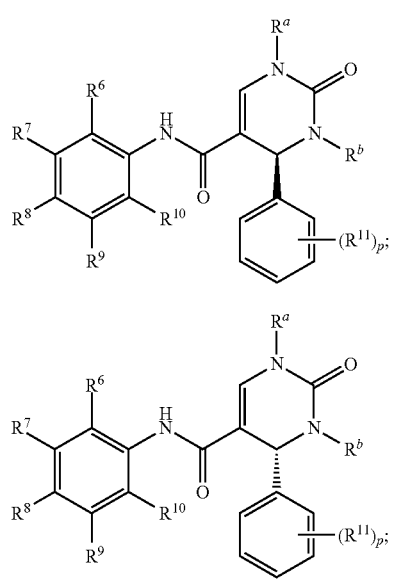

wherein p, $R^6$, $R^7$, $R^8$, $R^9$, $R^{10}$, $R^{11}$ and are as defined herein.

In certain embodiments, the subject compounds are of formula IIa.

In certain embodiments, the subject compounds are of formula IIb.

In certain embodiments of any of formulas II, IIa and IIb, at least two of $R^6$, $R^7$, $R^8$, $R^9$ and $R^{10}$ are not hydrogen.

In certain embodiments of any of formulas II, IIa and IIb, at least three of $R^6$, $R^7$, $R^8$, $R^9$ and $R^{10}$ are not hydrogen.

In certain embodiments of any of formulas II, IIa and IIb, $R^6$, $R^7$, $R^8$, $R^9$ and $R^{10}$ each independently is: hydrogen; fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; a five- or six-membered heteroaryl selected from: pyrrolyl; pyrazolyl; triazolyl; pyridinyl; pyrimidinyl; pyrazinyl; pyridazinyl; or triazinyl, each optionally substituted; or two adjacent substituents may form methylenedioxy, ethylenedioxy or difluoromethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; or ethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; methyl; and methoxy.

In certain embodiments of any of formulas II, IIa and IIb, $R^6$ is halo or methyl, $R^{10}$ is hydrogen, one of $R^7$, $R^8$ and $R^9$ is hydrogen and the others of $R^7$, $R^8$ and $R^9$ are each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; and hydroxypropoxy.

In certain embodiments of any of formulas II, IIa and IIb, $R^6$ is halo or methyl, $R^{10}$ is hydrogen, two of $R^7$, $R^8$ and $R^9$ is hydrogen and the other of $R^7$, $R^8$ and $R^9$ is selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; and hydroxypropoxy.

In certain embodiments of any of formulas II, IIa and IIb, $R^6$, $R^7$, $R^8$, $R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; alkoxyalkoxy; hydroxyalkoxy; alkylsulfonylalkoxy; hydroxyalkyl; or $C_{3-6}$cycloalkyl-$C_{1-6}$alkoxy.

In certain embodiments of any of formulas II, IIa and IIb, $R^6$, $R^7$, $R^8$, $R^9$ and $R^{10}$ each independently is: hydrogen; fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; or hydroxyethyl.

In certain embodiments of any of formulas II, IIa and IIb, $R^6$, $R^7$, $R^8$, $R^9$ and $R^{10}$ each independently is: hydrogen; fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of any of formulas II, IIa and IIb, $R^7$ and $R^{10}$ are hydrogen.

In certain embodiments of any of formulas II, IIa and IIb, $R^7$, $R^8$ and $R^{10}$ are hydrogen.

In certain embodiments of any of formulas II, IIa and IIb, $R^6$ is: hydrogen; halo; or methyl.

In certain embodiments of any of formulas II, IIa and IIb, $R^6$ is: halo; or methyl.

In certain embodiments of any of formulas II, IIa and IIb, $R^6$ is methyl.

In certain embodiments of any of formulas II, IIa and IIb, $R^8$ is: hydrogen; methoxy; halo; methyl; or difluoromethoxy.

In certain embodiments of any of formulas II, IIa and IIb, $R^9$ is: methoxy; hydrogen; 2-hydroxy-ethoxy; 2-methoxy-ethoxy; 1-hydroxy-ethyl; or cyclopropylmethyl.

In certain embodiments of any of formulas II, IIa and IIb, $R^9$ is: methoxy; hydrogen; 2-hydroxy-ethoxy; 2-methoxy-ethoxy; 1-hydroxy-ethyl; cyclopropylmethyl; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas II, IIa and IIb, $R^9$ is: methoxy; 2-hydroxy-ethoxy; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas II, IIa and IIb, $R^9$ is: methoxy; 2-hydroxy-ethoxy; 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

In certain embodiments of any of formulas II, IIa and IIb, p is 0, 1 or 2.

In certain embodiments of any of formulas II, IIa and IIb, p is 1 or 2.

In certain embodiments of any of formulas II, IIa and IIb, p is 1.

In certain embodiments of any of formulas II, IIa and IIb, each $R^{11}$ independently is: halo; $C_{1-6}$alkyl; or $C_{1-6}$alkoxy.

In certain embodiments of any of formulas II, IIa and IIb, each $R^{11}$ independently is fluoro or methyl.

In certain embodiments of any of formulas II, IIa and IIb, $R^{11}$ is halo.

In certain embodiments of any of formulas II, IIa and IIb, $R^{11}$ is fluoro.

In certain embodiments of any of formulas II, IIa and IIb p is 1 and $R^{11}$ is halo.

In certain embodiments of any of formulas II, IIa and IIb p is 1 and $R^{11}$ is 3-halo or 4-halo.

In certain embodiments of any of formulas II, IIa and IIb p is 1 and $R^{11}$ is fluoro.

In certain embodiments of any of formulas II, IIa and IIb p is 1 and $R^{11}$ is 3-fluoro or 4-fluoro.

In certain embodiments of any of formulas II, IIa and IIb p is 1 and $R^{11}$ is 4-fluoro.

In certain embodiments of any of formula II, IIa and IIb, $R^a$ is methyl.

In certain embodiments of any of formula II, IIa and IIb, $R^b$ is hydrogen.

In certain embodiments of any of formulas II, IIa and IIb:
$R^6$ is: hydrogen; halo; methyl; or ethyl;
$R^7$ is hydrogen; methyl; methoxy; or methoxycarbonyl;
$R^8$ is: hydrogen; methoxy; halo; methyl; or difluoromethoxy;
$R^9$ is: hydrogen; methoxy; hydrogen; 2-hydroxy-ethoxy; 2-methoxy-ethoxy; 1-hydroxy-ethyl; and
$R^{10}$ is hydrogen; or halo.

In certain embodiments of any of formulas II, IIa and IIb:
$R^6$ is: halo; or methyl;
$R^7$ is hydrogen;
$R^8$ is: hydrogen; methoxy; halo; methyl; or difluoromethoxy;
$R^9$ is: methoxy; 2-hydroxy-ethoxy; 2-methoxy-ethoxy; or 1-hydroxy-ethyl; and
$R^{10}$ is hydrogen; or halo.

In certain embodiments of any of formulas II, IIa and IIb:
$R^6$ is: bromo; or methyl;
$R^7$ is hydrogen;
$R^8$ is: hydrogen; methoxy; chloro; fluoro; methyl; or difluoromethoxy;
$R^9$ is: methoxy; 2-hydroxy-ethoxy; 2-methoxy-ethoxy; or 1-hydroxy-ethyl; and
$R^{10}$ is hydrogen.

In certain embodiments of any of formulas II, IIa and IIb:
$R^6$ is methyl;
$R^7$ is hydrogen;
$R^8$ is: hydrogen; methoxy; chloro; fluoro; methyl; or difluoromethoxy;
$R^9$ is: methoxy; 2-hydroxy-ethoxy; 2-methoxy-ethoxy; or 1-hydroxy-ethyl; and
$R^{10}$ is hydrogen.

In certain embodiments of any of formulas II, IIa and IIb:
$R^6$ is: halo; methyl; or ethyl;
$R^7$ is hydrogen;
$R^8$ is: hydrogen; methoxy; or halo;
$R^9$ is: methoxy; 2-hydroxy-ethoxy; 2-methoxy-ethoxy; 1-hydroxy-ethyl; 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl;

4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl); 2-methyl-3-oxo-2,3-dihydro-pyridazin-4-yl; or 1-methyl-6-oxo-1,6-dihydro-pyridin-3-yl; and $R^{10}$ is hydrogen.

In certain embodiments of any of formulas II, IIa and IIb:
$R^6$ is: halo; methyl; or ethyl;
$R^7$ is hydrogen;
$R^8$ is: hydrogen; methoxy; or halo;
$R^9$ is: methoxy; 2-hydroxy-ethoxy; 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl; and $R^{10}$ is hydrogen.

In certain embodiments of any of formulas II, IIa and IIb, p is 1 or 2 and $R^{11}$ is halo.

In certain embodiments of any of formulas II, IIa and IIb, p is 1 or 2 and $R^{11}$ is fluoro.

In certain embodiments of any of formulas II, IIa and IIb, p is 1 and $R^{11}$ is fluoro.

In certain embodiments of any of formulas II, IIa and IIb, p is 1 and $R^{11}$ is fluoro at the 4-position.

In certain embodiments, the compounds of formula I may be more specifically of formula III:

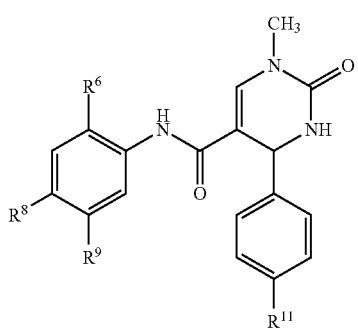

wherein $R^6$, $R^8$, $R^9$ and $R^{11}$ are as defined herein.

In certain embodiments of formula III, the subject compounds may be more specifically of formula IIIa or formula IIIb;

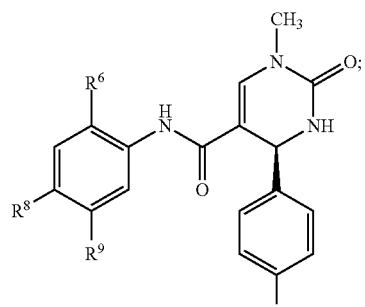

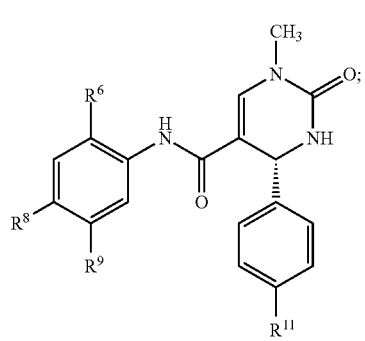

wherein $R^6$, $R^8$, $R^9$ and $R^{11}$ are as defined herein.

In certain embodiments, the subject compounds are of formula IIIa.

In certain embodiments, the subject compounds are of formula IIIb.

In certain embodiments of any of formulas III, IIIa and IIIb, $R^6$ is: halo; methyl; or ethyl.

In certain embodiments of any of formulas III, IIIa and IIIb, $R^6$ is: bromo; or methyl.

In certain embodiments of any of formulas III, IIIa and IIIb, $R^6$ is methyl.

In certain embodiments of any of formulas III, IIIa and IIIb, $R^6$ is ethyl.

In certain embodiments of any of formulas III, IIIa and IIIb, $R^6$ is bromo.

In certain embodiments of any of formulas III, IIIa and IIIb, $R^8$ and $R^9$ each independently is: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; or hydroxypropoxy.

In certain embodiments of any of formulas III, IIIa and IIIb, $R^8$ is: hydrogen; methoxy; halo; methyl; or difluoromethoxy.

In certain embodiments of any of formulas III, IIIa and IIIb, $R^8$ is: hydrogen; methoxy; or halo.

In certain embodiments of any of formulas III, IIIa and IIIb, $R^8$ is hydrogen.

In certain embodiments of any of formulas III, IIIa and IIIb, $R^8$ is methoxy.

In certain embodiments of any of formulas III, IIIa and IIIb, $R^8$ is chloro.

In certain embodiments of any of formulas III, IIIa and IIIb, $R^8$ is fluoro.

In certain embodiments of any of formulas III, IIIa and IIIb, $R^9$ is: methoxy; 2-hydroxy-ethoxy; 2-methoxy-ethoxy; 1-hydroxy-ethyl; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is: methoxy; 2-hydroxy-ethoxy; or a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is methoxy.

In certain embodiments of any of formulas III, IIIa and IIIb, $R^9$ is 2-hydroxy-ethoxy.

In certain embodiments of any of formulas III, IIIa and IIIb, $R^9$ is 2-methoxy-ethoxy.

In certain embodiments of any of formulas III, IIIa and IIIb, $R^9$ is 1-hydroxy-ethyl.

In certain embodiments of any of formulas III, IIIa and IIIb, $R^9$ is a five- or six-membered heteroaryl selected from: pyrrolyl; pyrazolyl; triazolyl; pyridinyl; pyrimidinyl; pyrazinyl; pyridazinyl; or triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyrrolyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyrazolyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is triazolyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyridinyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyrimidinyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyrazinyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is pyridazinyl optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is triazinyl, each optionally substituted one, two or three times with a group or groups independently selected from: oxo; $C_{1-6}$alkyl; $C_{1-6}$alkoxy; hydroxy-$C_{1-6}$alkyl; or hydroxy-$C_{1-6}$alkoxy-$C_{1-6}$alkyl.

In certain embodiments of any of formulas III, IIIa and IIIb, $R^9$ is: 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl); 2-methyl-3-oxo-2,3-dihydro-pyridazin-4-yl; or 1-methyl-6-oxo-1,6-dihydro-pyridin-3-yl.

In certain embodiments of any of formulas III, IIIa and IIIb, $R^9$ is 5-methyl-1H-pyrazol-3-yl.

In certain embodiments of any of formulas III, IIIa and IIIb, $R^9$ is 4-methyl-pyrazol-1-yl.

In certain embodiments of any of formulas III, IIIa and IIIb, $R^9$ is 4,5-dimethyl-4H-[1,2,4]triazol-3-yl.

In certain embodiments of any of formulas III, IIIa and IIIb, $R^9$ is 2-methyl-3-oxo-2,3-dihydro-pyridazin-4-yl; 2H-pyrazol-3-yl.

In certain embodiments of any of formulas III, IIIa and IIIb, $R^9$ is 2H-pyrazol-3-yl.

In certain embodiments of any of formulas III, IIIa and IIIb, $R^9$ is 1-((R)-2-hydroxy-3-methoxy-propyl)-5-methyl-1H-pyrazol-3-yl.

In certain embodiments of any of formulas III, IIIa and IIIb, $R^9$ is 4-((R)-2-hydroxy-3-methoxy-propyl)-3,5-dioxo-4,5-dihydro-3H-[1,2,4]triazin-2-yl.

In certain embodiments of any of formulas III, IIIa and IIIb, $R^9$ is 6-oxo-6H-pyridazin-1-yl.

In certain embodiments of any of formulas III, IIIa and IIIb, $R^9$ is 3-methyl-6-oxo-6H-pyridazin-1-yl.

In certain embodiments of any of formulas III, IIIa and IIIb, $R^9$ is 6-oxo-1,6-dihydro-pyrazin-2-yl.

In certain embodiments of any of formulas III, IIIa and IIIb, $R^9$ is 2-methyl-3-oxo-2,3-dihydro-pyridazin-4-yl.

In certain embodiments of any of formulas III, IIIa and IIIb, $R^9$ is 4-methyl-3,5-dioxo-4,5-dihydro-3H-[1,2,4]triazin-2-yl.

In certain embodiments of any of formulas III, IIIa and IIIb, $R^9$ is 1-((S)-2-hydroxy-3-methoxy-propyl)-5-methyl-1H-pyrazol-3-yl.

In certain embodiments of any of formulas III, IIIa and IIIb, $R^9$ is 2-ethyl-3-oxo-2,3-dihydro-pyridazin-4-yl).

In certain embodiments of any of formulas III, IIIa and IIIb, $R^9$ is 1-methyl-6-oxo-1,6-dihydro-pyridazin-3-yl.

In certain embodiments of any of formulas III, IIIa and IIIb, $R^9$ is 6-oxo-1,6-dihydro-pyridazin-3-yl.

In certain embodiments of any of formulas III, IIIa and IIIb, $R^9$ is 2-((R)-2-hydroxy-3-methoxy-propyl)-3-oxo-2,3-dihydro-pyridazin-4-yl.

In certain embodiments of any of formulas III, IIIa and IIIb, $R^9$ is 2-oxo-pyrrolidin-1-yl.

In certain embodiments of any of formulas III, IIIa and IIIb, $R^9$ is 2,4-dioxo-3,4-dihydro-2H-pyrimidin-1-yl.

In certain embodiments of any of formulas III, IIIa and IIIb, $R^9$ is 3-methyl-2-oxo-2H-pyridin-1-yl.

In certain embodiments of any of formulas III, IIIa and IIIb, $R^9$ is 2-oxo-2H-pyridin-1-yl; 6-methoxy-pyridazin-3-yl.

In certain embodiments of any of formulas III, IIIa and IIIb, $R^9$ is 2,6-dioxo-3,6-dihydro-2H-pyrimidin-1-yl.

In certain embodiments of any of formulas III, IIIa and IIIb, $R^9$ is: methoxy; 2-hydroxy-ethoxy; 2-methoxy-ethoxy; or 1-hydroxy-ethyl.

In certain embodiments of any of formulas III, IIIa and IIIb, $R^9$ is (2-hydroxy-ethyl)-6-oxo-1,6-dihydro-pyridazin-3-yl.

In certain embodiments of any of formulas III, IIIa and IIIb, $R^9$ is 1-methyl-2-oxo-1,2-dihydro-pyridin-3-yl.

In certain embodiments of any of formulas III, IIIa and IIIb, $R^9$ is (2-hydroxy-3-methoxy-propyl)-6-oxo-1,6-dihydro-pyridazin-3-yl.

In certain embodiments of any of formulas III, IIIa and IIIb, $R^9$ is 6-oxo-6H-pyridazin-1-yl.

In certain embodiments of any of formulas III, IIIa and IIIb, $R^9$ is 4-ethyl-3,5-dioxo-4,5-dihydro-3H-[1,2,4]triazin-2-yl.

In certain embodiments of any of formulas III, IIIa and IIIb, $R^9$ is 3-methyl-2-oxo-2H-pyridin-1-yl; or 4-methyl-6-oxo-6H-pyridazin-1-yl.

In certain embodiments of any of formulas III, IIIa and IIIb, $R^9$ is 2-methyl-5-(3-methyl-2,4-dioxo-3,4-dihydro-2H-pyrimidin-1-yl.

In certain embodiments of any of formulas III, IIIa and IIIb, $R^9$ is 2-methyl-5-(5-methyl-2-oxo-2H-pyridin-1-yl.

In certain embodiments of any of formulas III, IIIa and IIIb, $R^9$ is 2-methyl-3-oxo-2,3-dihydro-pyridazin-4-yl.

In certain embodiments of any of formulas III, IIIa and IIIb, $R^9$ is 1-methyl-6-oxo-1,6-dihydro-pyridin-3-yl.

In certain embodiments of any of formulas III, IIIa and IIIb, $R^{11}$ is halo.

In certain embodiments of any of formulas III, IIIa and IIIb, $R^{11}$ is fluoro.

Where any of $R^1$, $R^2$, $R^3$, $R^4$, $R^5$, $R^6$, $R^7$, $R^8$, $R^9$, $R^{10}$, $R^{11}$, $R^a$ or $R^b$ is alkyl or contains an alkyl moiety, such alkyl is preferably lower alkyl, i.e. $C_1$-$C_6$alkyl, and in many embodiments is $C_1$-$C_4$alkyl.

The invention also provides methods for treating a disease or condition mediated by or otherwise associated with a P2X7 receptor, the method comprising administering to a subject in need thereof an effective amount of a compound of the invention.

The invention also provides methods for treating an inflammatory, respiratory or diabetes condition, the method comprising administering to a subject in need thereof an effective amount of a compound of the invention together with an effective amount of a P2X7 inhibitor.

The disease may be an inflammatory disease such as arthritis, and more particularly rheumatoid arthritis, osteoarthritis, psoriasis, allergic dermatitis, asthma, chronic obstructive pulmonary disease, airways hyper-responsiveness, septic shock, glomerulonephritis, irritable bowel disease, and Crohn's disease.

The disease may be a pain condition, such as inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

The disease may be diabetes.

The disease may be Alzheimer's.

Representative compounds in accordance with the methods of the invention are shown in Table 1.

TABLE 1

| # | Structure | Name (Autonom) | M + H | $pIC_{50}$ |
|---|---|---|---|---|
| 1 | 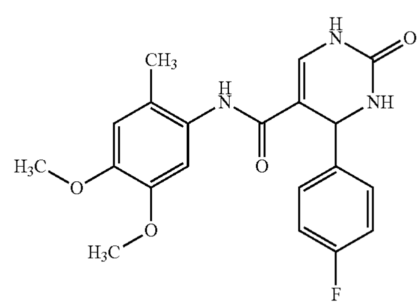 [SMILES: COc1cc(C)c(NC(=O)C2=CNC(=O)NC2c2ccc(F)cc2)cc1OC] | 4-(4-Fluoro-phenyl)-2-oxo-1,2,3,4-tetrahydro-pyrimidine-5-carboxylic acid (4,5-dimethoxy-2-methyl-phenyl)-amide | 386 | 7.46 |
| 2 | 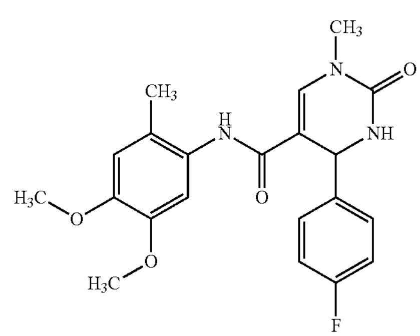 [SMILES: COc1cc(C)c(NC(=O)C2=CN(C)C(=O)NC2c2ccc(F)cc2)cc1OC] | 4-(4-Fluoro-phenyl)-1-methyl-2-oxo-1,2,3,4-tetrahydro-pyrimidine-5-carboxylic acid (4,5-dimethoxy-2-methyl-phenyl)-amide | 400 | 7.385 |

TABLE 1-continued

| # | Structure | Name (Autonom) | M + H | pIC$_{50}$ |
|---|---|---|---|---|
| 3 | 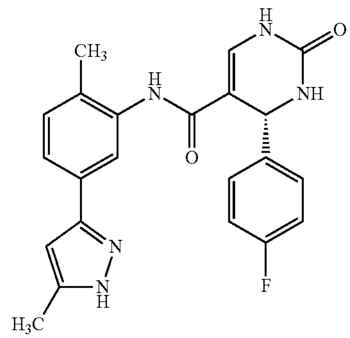 [SMILES: Cc1cc(-c2ccc(C)c(NC(=O)C3=CNC(=O)N[C@@H]3c3ccc(F)cc3)c2)n[nH]1] | (R)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide | 406 | 6.763 |
| 4 | 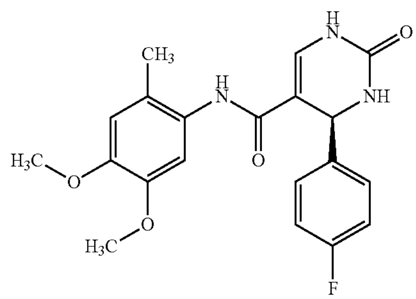 [SMILES: COc1cc(C)c(NC(=O)C2=CNC(=O)N[C@H]2c2ccc(F)cc2)cc1OC] | (S)-4-(4-Fluoro-phenyl)-2-oxo-1,2,3,4-tetrahydro-pyrimidine-5-carboxylic acid (4,5-dimethoxy-2-methyl-phenyl)-amide | | 7.223 |
| 5 | 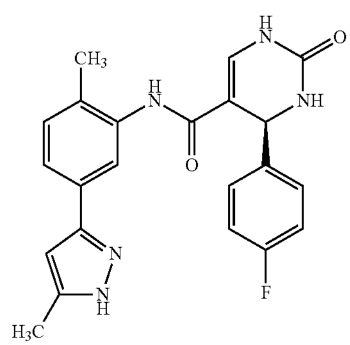 [SMILES: Cc1cc(-c2ccc(C)c(NC(=O)C3=CNC(=O)N[C@H]3c3ccc(F)cc3)c2)n[nH]1] | (S)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide | 406 | 7.705 |
| 6 | 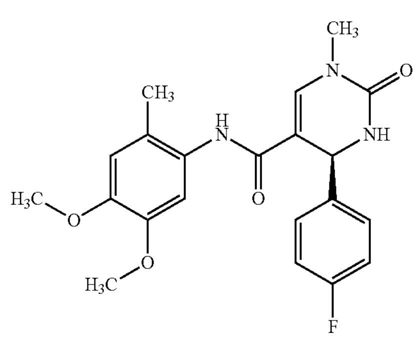 [SMILES: COc1cc(C)c(NC(=O)C2=CN(C)C(=O)N[C@H]2c2ccc(F)cc2)cc1OC] | (S)-4-(4-Fluoro-phenyl)-1-methyl-2-oxo-1,2,3,4-tetrahydro-pyrimidine-5-carboxylic acid (4,5-dimethoxy-2-methyl-phenyl)-amide | 400 | 7.455 |

TABLE 1-continued

| # | Structure | Name (Autonom) | M + H | pIC$_{50}$ |
|---|---|---|---|---|
| 7 | 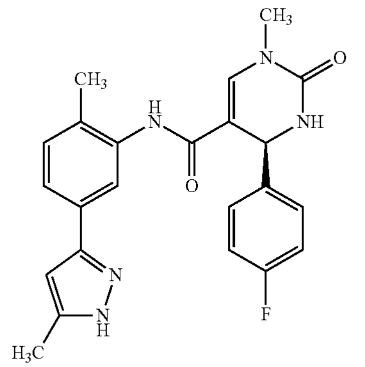 [SMILES: Cc1cc(-c2ccc(C)c(NC(=O)C3=CN(C)C(=O)N[C@H]3c3ccc(F)cc3)c2)n[nH]1] | (S)-4-(4-Fluoro-phenyl)-1-methyl-2-oxo-1,2,3,4-tetrahydro-pyrimidine-5-carboxylic acid [2-methyl-5-(5-methyl-1H-pyrazol-3-yl)-phenyl]-amide | 420 | 7.455 |
| 8 | 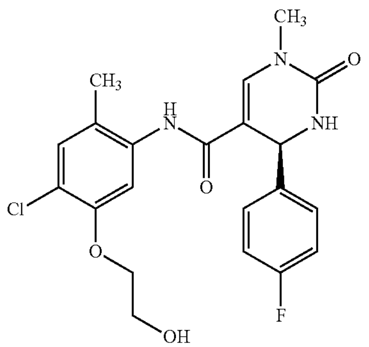 [SMILES: Cc1cc(Cl)c(OCCO)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-chloro-5-(2-hydroxy-ethoxy)-2-methyl-phenyl]-amide | 434 | 7.641 |
| 9 | 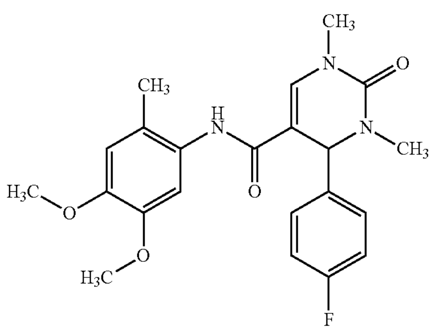 | 4-(4-Fluoro-phenyl)-1,3-dimethyl-2-oxo-1,2,3,4-tetrahydro-pyrimidine-5-carboxylic acid (4,5-dimethoxy-2-methyl-phenyl)-amide | 414 | 6.707 |
| 10 | 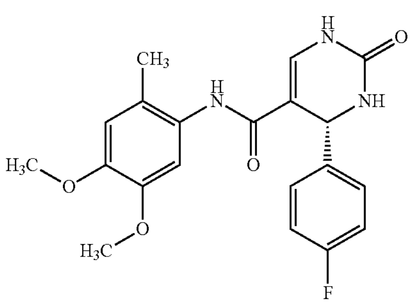 [SMILES: COc1cc(C)c(NC(=O)C2=CNC(=O)N[C@@H]2c2ccc(F)cc2)cc1OC] | (R)-4-(4-Fluoro-phenyl)-2-oxo-1,2,3,4-tetrahydro-pyrimidine-5-carboxylic acid (4,5-dimethoxy-2-methyl-phenyl)-amide | 386 | 6.445 |

TABLE 1-continued

| # | Structure | Name (Autonom) | M + H | pIC$_{50}$ |
|---|---|---|---|---|
| 11 | 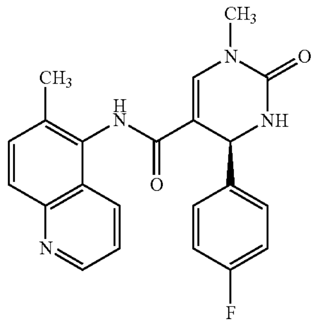 [SMILES: Cc1ccc2ncccc2c1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid (6-methyl-quinolin-5-yl)-amide | 391 | 6.92 |
| 12 | 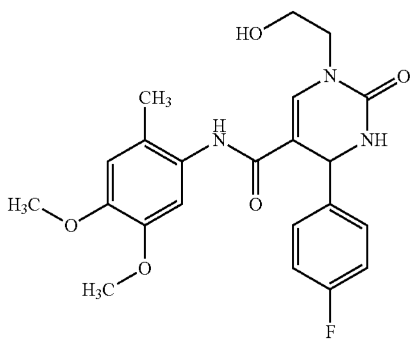 [SMILES: COc1cc(C)c(NC(=O)C2=CN(CCO)C(=O)NC2c2ccc(F)cc2)cc1OC] | 4-(4-Fluoro-phenyl)-1-(2-hydroxy-ethyl)-2-oxo-1,2,3,4-tetrahydro-pyrimidine-5-carboxylic acid (4,5-dimethoxy-2-methyl-phenyl)-amide | 430 | 6.955 |
| 13 | 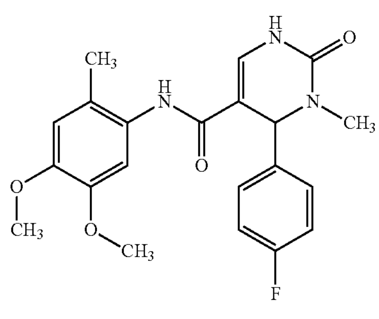 [SMILES: COc1cc(C)c(NC(=O)C2=CNC(=O)N(C)C2c2ccc(F)cc2)cc1OC] | 4-(4-Fluoro-phenyl)-3-methyl-2-oxo-1,2,3,4-tetrahydro-pyrimidine-5-carboxylic acid (4,5-dimethoxy-2-methyl-phenyl)-amide | 400 | 7.07 |
| 14 | 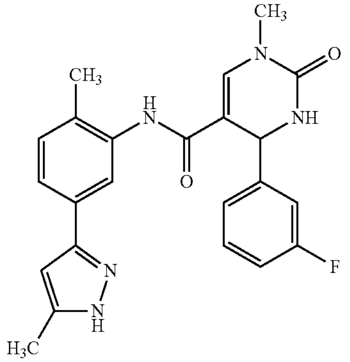 [SMILES: Cc1cc(-c2ccc(C)c(NC(=O)C3=CN(C)C(=O)NC3c3cccc(F)c3)c2)n[nH]1] | 4-(3-Fluoro-phenyl)-1-methyl-2-oxo-1,2,3,4-tetrahydro-pyrimidine-5-carboxylic acid [2-methyl-5-(5-methyl-1H-pyrazol-3-yl)-phenyl]-amide | 420 | 7.237 |

TABLE 1-continued

| # | Structure | Name (Autonom) | M + H | pIC$_{50}$ |
|---|---|---|---|---|
| 15 | 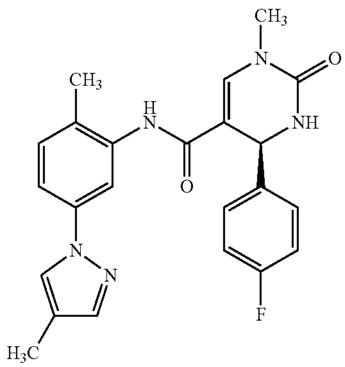 [SMILES: Cc1cnn(-c2ccc(C)c(NC(=O)C3=CN(C)C(=O)N[C@H]3c3ccc(F)cc3)c2)c1] | (S)-4-(4-Fluoro-phenyl)-1-methyl-2-oxo-1,2,3,4-tetrahydro-pyrimidine-5-carboxylic acid [2-methyl-5-(4-methyl-pyrazol-1-yl)-phenyl]-amide | 420 | 7.85 |
| 16 | 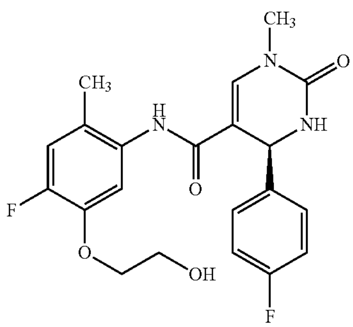 [SMILES: Cc1cc(F)c(OCCO)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-fluoro-5-(2-hydroxy-ethoxy)-2-methyl-phenyl]-amide | 418 | 8.035 |
| 17 | 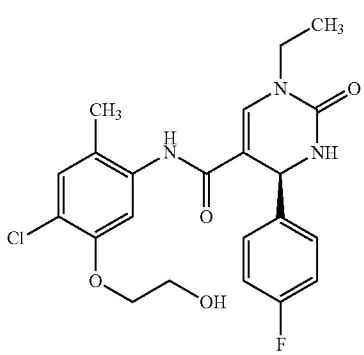 [SMILES: CCN1C=C(C(=O)Nc2cc(OCCO)c(Cl)cc2C)[C@H](c2ccc(F)cc2)NC1=O] | (S)-1-Ethyl-4-(4-fluoro-phenyl)-2-oxo-1,2,3,4-tetrahydro-pyrimidine-5-carboxylic acid [4-chloro-5-(2-hydroxy-ethoxy)-2-methyl-phenyl]-amide | | 7.62 |
| 18 | 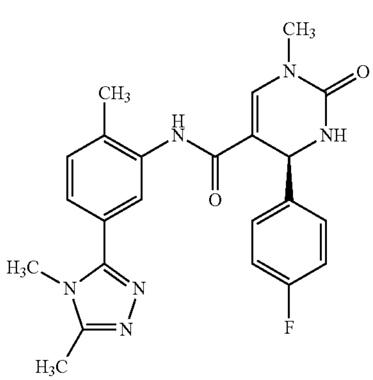 [SMILES: Cc1ccc(-c2nnc(C)n2C)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [5-(4,5-dimethyl-4H-[1,2,4]triazol-3-yl)-2-methyl-phenyl]-amide | 435 | 7.655 |

TABLE 1-continued

| # | Structure | Name (Autonom) | M + H | pIC$_{50}$ |
|---|---|---|---|---|
| 19 | 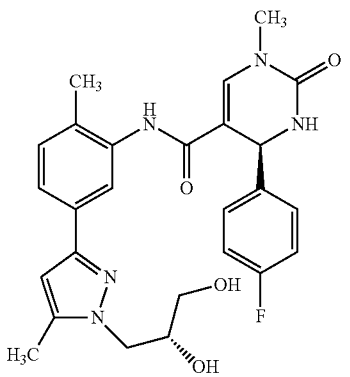 [SMILES: Cc1ccc(-c2cc(C)n(C[C@@H](O)CO)n2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydropyrimidine-5-carboxylic acid {5-[1-((R)-2,3-dihydroxy-propyl)-5-methyl-1H-pyrazol-3-yl]-2-methyl-phenyl}-amide | 494 | 7.64 |
| 20 | 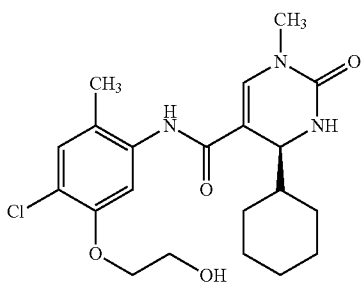 [SMILES: Cc1cc(Cl)c(OCCO)cc1NC(=O)C1=CN(C)C(=O)N[C@H]1C1CCCCC1] | (S)-4-Cyclohexyl-1-methyl-2-oxo-1,2,3,4-tetrahydro-pyrimidine-5-carboxylic acid [4-chloro-5-(2-hydroxy-ethoxy)-2-methyl-phenyl]-amide | 423 | |
| 21 | 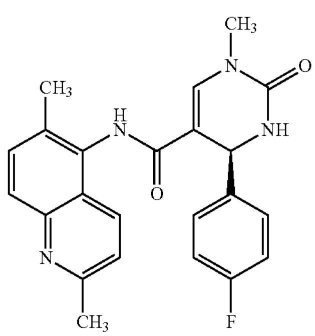 [SMILES: Cc1ccc2c(NC(=O)C3=CN(C)C(=O)N[C@H]3c3ccc(F)cc3)c(C)ccc2n1] | (S)-4-(4-Fluoro-phenyl)-1-methyl-2-oxo-1,2,3,4-tetrahydro-pyrimidine-5-carboxylic acid (2,6-dimethyl-quinolin-5-yl)-amide | 405 | 7.055 |
| 22 | 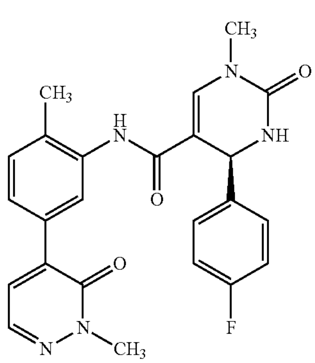 [SMILES: Cc1ccc(-c2ccnn(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(2-methyl-3-oxo-2,3-dihydro-pyridazin-4-yl)-phenyl]-amide | 448 | 7.94 |

TABLE 1-continued

| # | Structure | Name (Autonom) | M + H | pIC$_{50}$ |
|---|---|---|---|---|
| 23 | 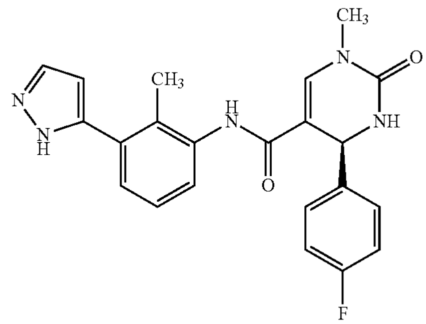 [SMILES: Cc1c(NC(=O)C2=CN(C)C(=O)N[C@H]2c2ccc(F)cc2)cccc1-c1ccn[nH]1] | (S)-4-(4-Fluoro-phenyl)-1-methyl-2-oxo-1,2,3,4-tetrahydro-pyrimidine-5-carboxylic acid [2-methyl-3-(2H-pyrazol-3-yl)-phenyl]-amide | 406 | 6.735 |
| 24 | 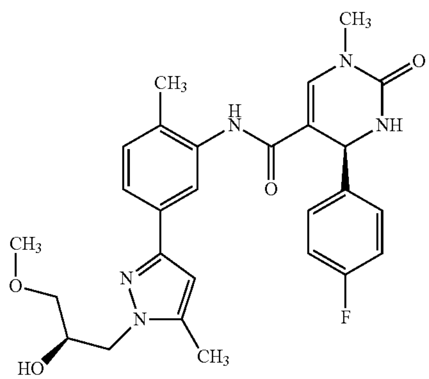 [SMILES: COC[C@H](O)Cn1nc(-c2ccc(C)c(NC(=O)C3=CN(C)C(=O)N[C@H]3c3ccc(F)cc3)c2)cc1C] | (S)-4-(4-Fluoro-phenyl)-1-methyl-2-oxo-1,2,3,4-tetrahydro-pyrimidine-5-carboxylic acid {5-[1-((R)-2-hydroxy-3-methoxy-propyl)-5-methyl-1H-pyrazol-3-yl]-2-methyl-phenyl}-amide | 508 | 7.295 |
| 25 | 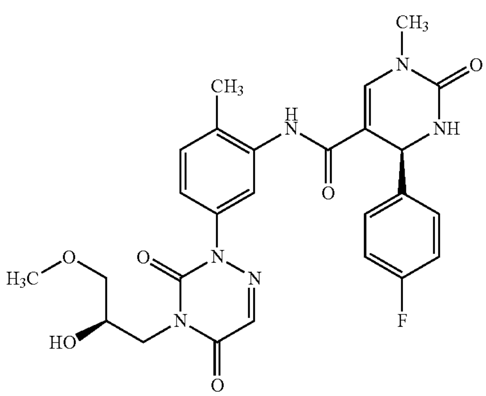 [SMILES: COC[C@H](O)Cn1c(=O)cnn(-c2ccc(C)c(NC(=O)C3=CN(C)C(=O)N[C@H]3c3ccc(F)cc3)c2)c1=O] | (S)-4-(4-Fluoro-phenyl)-1-methyl-2-oxo-1,2,3,4-tetrahydro-pyrimidine-5-carboxylic acid {5-[4-((R)-2-hydroxy-3-methoxy-propyl)-3,5-dioxo-4,5-dihydro-3H-[1,2,4]triazin-2-yl]-2-methyl-phenyl}-amide | 539 | 7.04 |
| 26 | 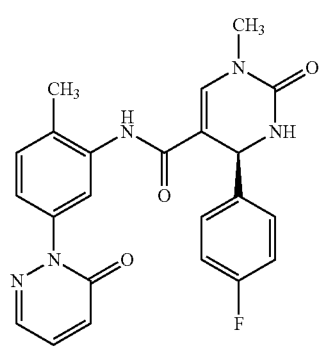 [SMILES: Cc1ccc(-n2ncccc2=O)cc1NC(=O)C1=CN(C)C(=O)N[C@H]1c1ccc(F)cc1] | S)-4-(4-Fluoro-phenyl)-1-methyl-2-oxo-1,2,3,4-tetrahydro-pyrimidine-5-carboxylic acid [2-methyl-5-(6-oxo-6H-pyridazin-1-yl)-phenyl]-amide | 434 | 7.7 |

TABLE 1-continued

| # | Structure | Name (Autonom) | M + H | pIC$_{50}$ |
|---|---|---|---|---|
| 27 | 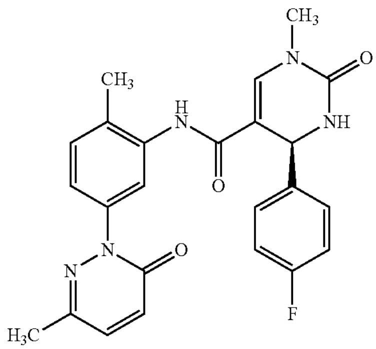 [SMILES: Cc1ccc(=O)n(-c2ccc(C)c(NC(=O)C3=CN(C)C(=O)N[C@H]3c3ccc(F)cc3)c2)n1] | (S)-4-(4-Fluoro-phenyl)-1-methyl-2-oxo-1,2,3,4-tetrahydro-pyrimidine-5-carboxylic acid [2-methyl-5-(3-methyl-6-oxo-6H-pyridazin-1-yl)-phenyl]-amide | 448 | 7.395 |
| 28 | 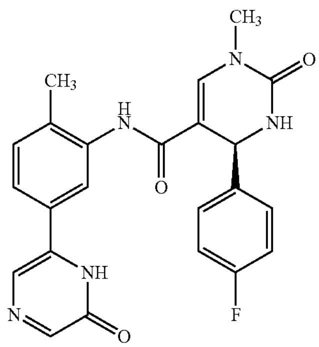 [SMILES: Cc1ccc(-c2cncc(=O)[nH]2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(6-oxo-1,6-dihydro-pyrazin-2-yl)-phenyl]-amide | 434 | 6.815 |
| 29 | 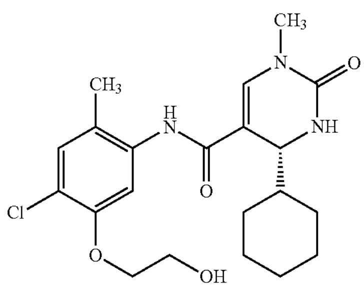 [SMILES: Cc1cc(Cl)c(OCCO)cc1NC(=O)C1=CN(C)C(=O)N[C@@H]1C1CCCCC1] | (R)-4-Cyclohexyl-1-methyl-2-oxo-1,2,3,4-tetrahydro-pyrimidine-5-carboxylic acid [4-chloro-5-(2-hydroxy-ethoxy)-2-methyl-phenyl]-amide | 423 | 7.262 |
| 30 | 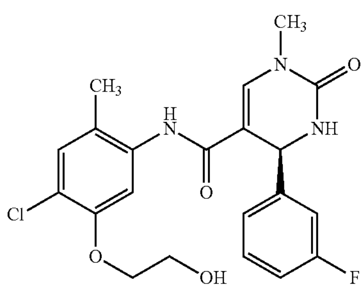 [SMILES: Cc1cc(Cl)c(OCCO)cc1NC(=O)C1=CN(C)C(=O)N[C@H]1c1cccc(F)c1] | (S)-4-(3-Fluoro-phenyl)-1-methyl-2-oxo-1,2,3,4-tetrahydro-pyrimidine-5-carboxylic acid [4-chloro-5-(2-hydroxy-ethoxy)-2-methyl-phenyl]-amide | 435 | 7.695 |
| 31 | 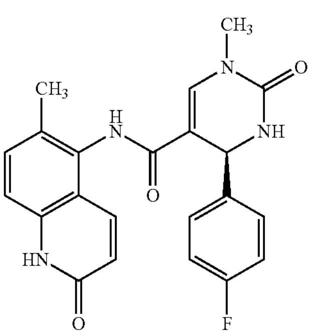 [SMILES: Cc1ccc2[nH]c(=O)ccc2c1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid (6-methyl-2-oxo-1,2-dihydro-quinolin-5-yl)-amide | 407 | 6.795 |

TABLE 1-continued

| # | Structure | Name (Autonom) | M + H | pIC$_{50}$ |
|---|---|---|---|---|
| 32 | 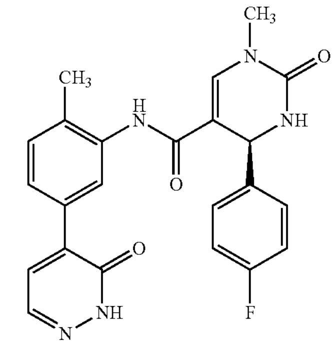 [SMILES: Cc1ccc(-c2ccn[nH]c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(3-oxo-2,3-dihydro-pyridazin-4-yl)-phenyl]-amide | 434 | 7.675 |
| 33 | 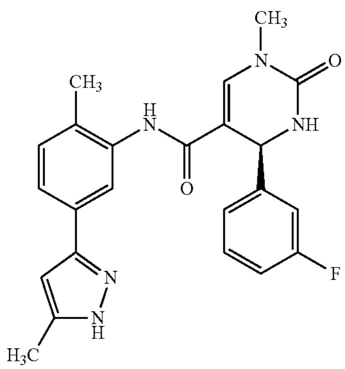 [SMILES: Cc1cc(-c2ccc(C)c(NC(=O)C3=CN(C)C(=O)N[C@H]3c3cccc(F)c3)c2)n[nH]1] | (S)-4-(3-Fluoro-phenyl)-1-methyl-2-oxo-1,2,3,4-tetrahydro-pyrimidine-5-carboxylic acid [2-methyl-5-(5-methyl-1H-pyrazol-3-yl)-phenyl]-amide | 420 | 6.97 |
| 34 | 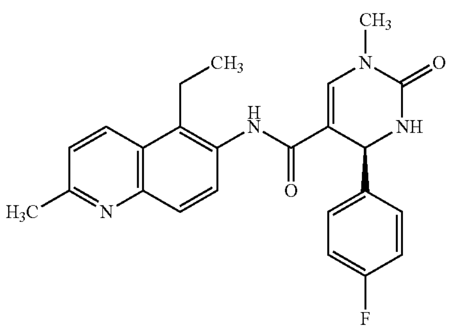 [SMILES: CCc1c(NC(=O)C2=CN(C)C(=O)N[C@H]2c2ccc(F)cc2)ccc2nc(C)ccc12] | (S)-4-(4-Fluoro-phenyl)-1-methyl-2-oxo-1,2,3,4-tetrahydro-pyrimidine-5-carboxylic acid (5-ethyl-2-methyl-quinolin-6-yl)-amide | 419 | 7.27 |
| 35 | 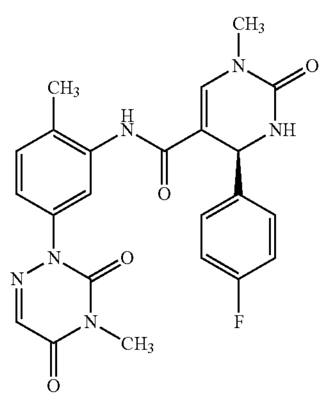 [SMILES: Cc1ccc(-n2ncc(=O)n(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(4-methyl-3,5-dioxo-4,5-dihydro-3H-[1,2,4]triazin-2-yl)-phenyl]-amide | 465 | 6.976667 |

TABLE 1-continued

| # | Structure | Name (Autonom) | M + H | pIC$_{50}$ |
|---|---|---|---|---|
| 36 | 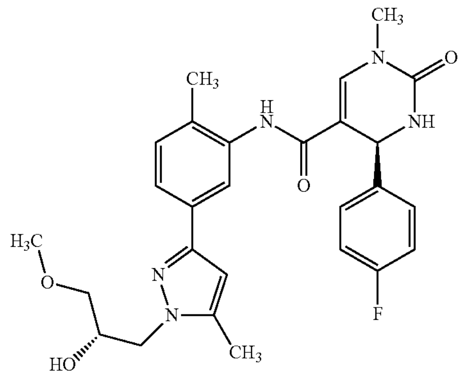 [SMILES: COC[C@@H](O)Cn1nc(-c2ccc(C)c(NC(=O)C3=CN(C)C(=O)N[C@H]3c3ccc(F)cc3)c2)cc1C] | (S)-4-(4-Fluoro-phenyl)-1-methyl-2-oxo-1,2,3,4-tetrahydro-pyrimidine-5-carboxylic acid {5-[1-((S)-2-hydroxy-3-methoxy-propyl)-5-methyl-1H-pyrazol-3-yl]-2-methyl-phenyl}-amide | 508 | 6.855 |
| 37 | 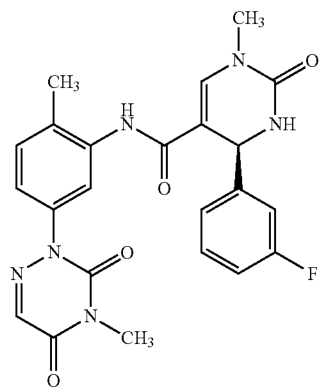 [SMILES: Cc1ccc(-n2ncc(=O)n(C)c2=O)cc1NC(=O)C1=CN(C)C(=O)N[C@H]1c1cccc(F)c1] | (S)-4-(3-Fluoro-phenyl)-1-methyl-2-oxo-1,2,3,4-tetrahydro-pyrimidine-5-carboxylic acid [2-methyl-5-(4-methyl-3,5-dioxo-4,5-dihydro-3H-[1,2,4]triazin-2-yl)-phenyl]-amide | 465 | 7.44 |
| 38 | 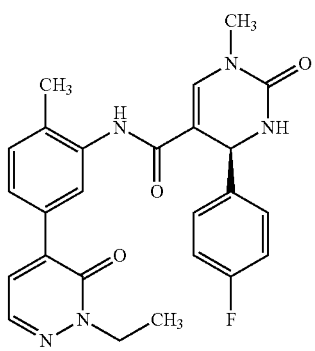 [SMILES: CCn1nccc(-c2ccc(C)c(NC(=O)C3=CN(C)C(=O)N[C@H]3c3ccc(F)cc3)c2)c1=O] | (S)-4-(4-Fluoro-phenyl)-1-methyl-2-oxo-1,2,3,4-tetrahydro-pyrimidine-5-carboxylic acid [5-(2-ethyl-3-oxo-2,3-dihydro-pyridazin-4-yl)-2-methyl-phenyl]-amide | 462 | 7.845 |
| 39 | 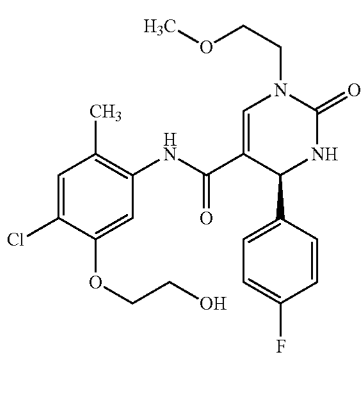 [SMILES: COCCN1C=C(C(=O)Nc2cc(OCCO)c(Cl)cc2C)[C@H](c2ccc(F)cc2)NC1=O] | (S)-4-(4-Fluoro-phenyl)-1-(2-methoxy-ethyl)-2-oxo-1,2,3,4-tetrahydro-pyrimidine-5-carboxylic acid [4-chloro-5-(2-hydroxy-ethoxy)-2-methyl-phenyl]-amide | 479 | 7.366667 |

TABLE 1-continued

| # | Structure | Name (Autonom) | M + H | pIC$_{50}$ |
|---|---|---|---|---|
| 40 | 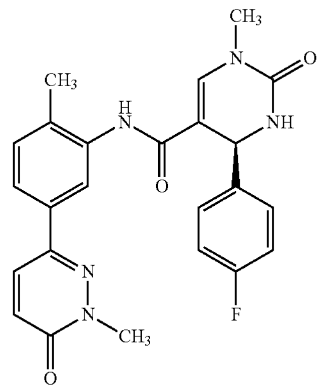 [SMILES: Cc1ccc(-c2ccc(=O)n(C)n2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(1-methyl-6-oxo-1,6-dihydro-pyridazin-3-yl)-phenyl]-amide | 478 | 7.14 |
| 41 | 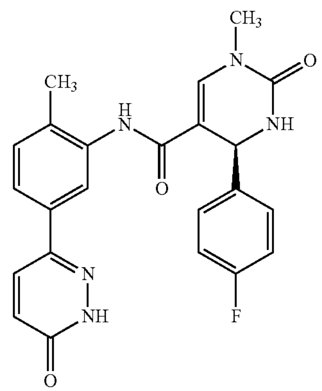 [SMILES: Cc1ccc(-c2ccc(=O)[nH]n2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(6-oxo-1,6-dihydro-pyridazin-3-yl)-phenyl]-amide | 434 | 7.535 |
| 42 | 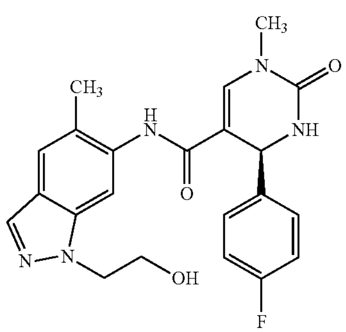 [SMILES: Cc1cc2cnn(CCO)c2cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidne-5-carboxylic acid [1-(2-hydroxy-ethyl)-5-methyl-1H-imidazol-6-yl]-amide | 424 | 7.84 |
| 43 | 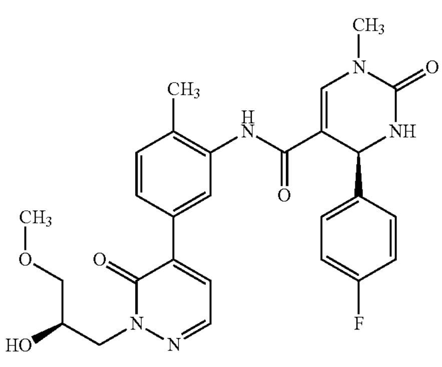 [SMILES: COC[C@H](O)Cn1nccc(-c2ccc(C)c(NC(=O)C3=CN(C)C(=O)N[C@H]3c3ccc(F)cc3)c2)c1=O] | (S)-4-(4-Fluoro-phenyl)-1-methyl-2-oxo-1,2,3,4-tetrahydro-pyrimidine-5-carboxylic acid {5-[2-((R)-2-hydroxy-3-methoxy-propyl)-3-oxo-2,3-dihydro-pyridazin-4-yl]-2-methyl-phenyl}-amide | 522 | 7.525 |

TABLE 1-continued

| # | Structure | Name (Autonom) | M + H | pIC$_{50}$ |
|---|---|---|---|---|
| 44 | 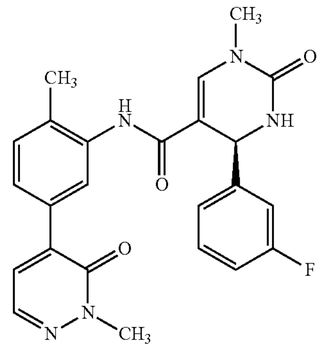 [SMILES: Cc1ccc(-c2ccnn(C)c2=O)cc1NC(=O)C1=CN(C)C(=O)N[C@H]1c1cccc(F)c1] | (S)-4-(3-Fluoro-phenyl)-1-methyl-2-oxo-1,2,3,4-tetrahydro-pyrimidine-5-carboxylic acid [2-methyl-5-(2-methyl-3-oxo-2,3-dihydro-pyridazin-4-yl)-phenyl]-amide | 448 | 7.265 |
| 45 | 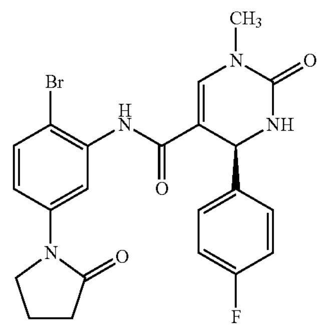 [SMILES: CN1C=C(C(=O)Nc2cc(N3CCCC3=O)ccc2Br)[C@H](c2ccc(F)cc2)NC1=O] | (S)-4-(4-Fluoro-phenyl)-1-methyl-2-oxo-1,2,3,4-tetrahydro-pyrimidine-5-carboxylic acid [2-bromo-5-(2-oxo-pyrrolidin-1-yl)-phenyl]-amide | 489 | 6.86 |
| 46 | 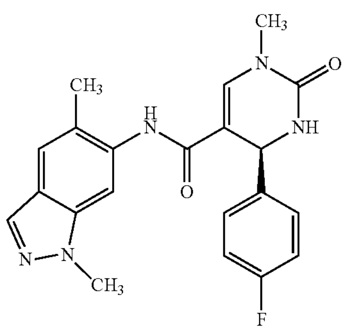 [SMILES: Cc1cc2cnn(C)c2cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid (1,5-dimethyl-1H-imidazol-6-yl)-amide | 394 | 7.915 |
| 47 | 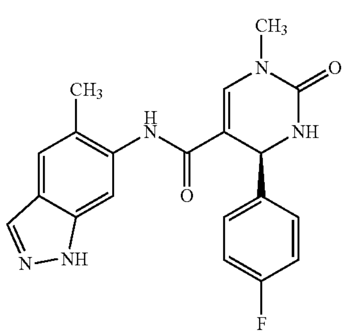 [SMILES: Cc1cc2cn[nH]c2cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid (5-methyl-1H-indazol-6-yl)-amide | 380 | 7.74 |

TABLE 1-continued

| # | Structure | Name (Autonom) | M + H | pIC$_{50}$ |
|---|---|---|---|---|
| 48 | 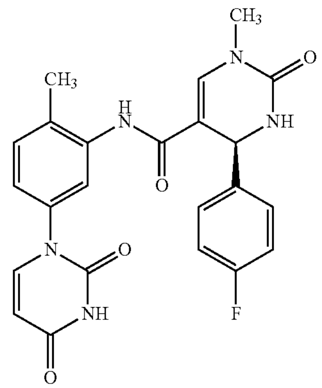 [SMILES: Cc1ccc(-n2ccc(=O)[nH]c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [5-(2,4-dioxo-3,4-dihydro-2H-pyrimidin-1-yl)-2-methyl-phenyl]-amide | 450 | 7.585 |
| 49 | 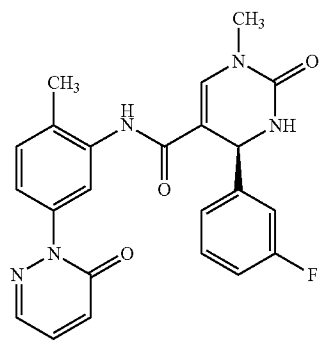 [SMILES: Cc1ccc(-n2ncccc2=O)cc1NC(=O)C1=CN(C)C(=O)N[C@H]1c1cccc(F)c1] | (S)-4-(3-Fluoro-phenyl)-1-methyl-2-oxo-1,2,3,4-tetrahydro-pyrimidine-5-carboxylic acid [2-methyl-5-(6-oxo-6H-pyridazin-1-yl)-phenyl]-amide | 434 | 6.98 |
| 50 | 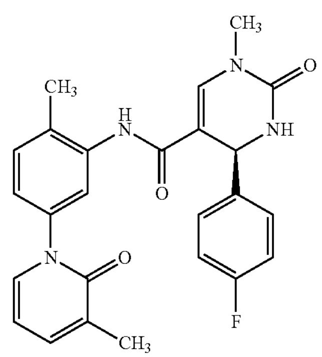 [SMILES: Cc1ccc(-n2cccc(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(3-methyl-2-oxo-2H-pyridin-1-yl)-phenyl]-amide | 447 | 7.26 |
| 51 | 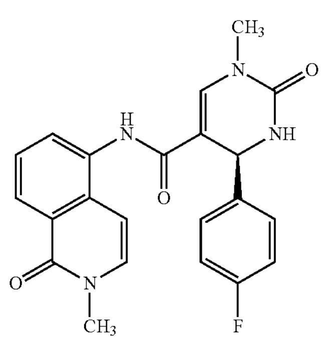 [SMILES: CN1C=C(C(=O)Nc2cccc3c(=O)n(C)ccc23)[C@H](c2ccc(F)cc2)NC1=O] | (S)-4-(4-Fluoro-phenyl)-1-methyl-2-oxo-1,2,3,4-tetrahydro-pyrimidine-5-carboxylic acid (2-methyl-1-oxo-1,2-dihydro-isoquinolin-5-yl)-amide | 407 | 7.2 |

TABLE 1-continued

| # | Structure | Name (Autonom) | M + H | pIC$_{50}$ |
|---|---|---|---|---|
| 52 | 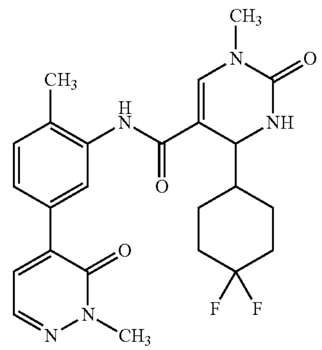 [SMILES: Cc1ccc(-c2ccnn(C)c2=O)cc1NC(=O)C1=CN(C)C(=O)NC1C1CCC(F)(F)CC1] | 4-(4,4-Difluoro-cyclohexyl)-1-methyl-2-oxo-1,2,3,4-tetrahydro-pyrimidine-5-carboxylic acid [2-methyl-5-(2-methyl-3-oxo-2,3-dihydro-pyridazin-4-yl)-phenyl]-amide | 472 | 6.47 |
| 53 | 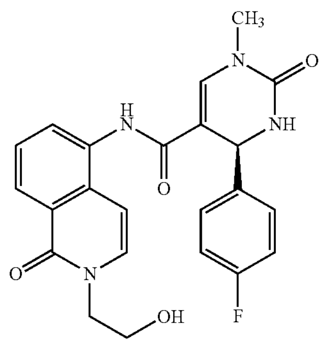 [SMILES: CN1C=C(C(=O)Nc2cccc3c(=O)n(CCO)ccc23)[C@H](c2ccc(F)cc2)NC1=O] | (S)-4-(4-Fluoro-phenyl)-1-methyl-2-oxo-1,2,3,4-tetrahydro-pyrimidine-5-carboxylic acid [2-(2-hydroxy-ethyl)-1-oxo-1,2-dihydro-isoquinolin-5-yl]-amide | 437 | 7.275 |
| 54 | 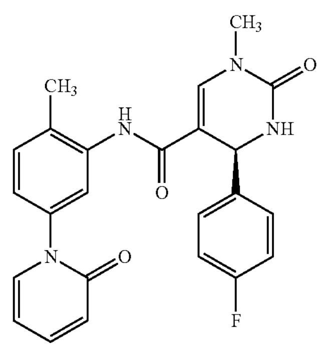 [SMILES: Cc1ccc(-n2ccccc2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(2-oxo-2H-pyridin-1-yl)-phenyl]-amide | 433 | 7.665 |
| 55 | 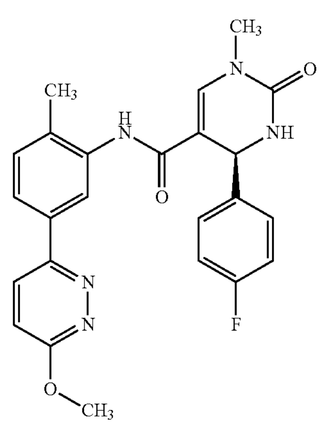 [SMILES: COc1ccc(-c2ccc(C)c(NC(=O)C3=CN(C)C(=O)N[C@H]3c3ccc(F)cc3)c2)nn1] | (S)-4-(4-Fluoro-phenyl)-1-methyl-2-oxo-1,2,3,4-tetrahydro-pyrimidine-5-carboxylic acid [5-(6-methoxy-pyridazin-3-yl)-2-methyl-phenyl]-amide | 448 | 7.96 |

TABLE 1-continued

| # | Structure | Name (Autonom) | M + H | pIC$_{50}$ |
|---|---|---|---|---|
| 56 | 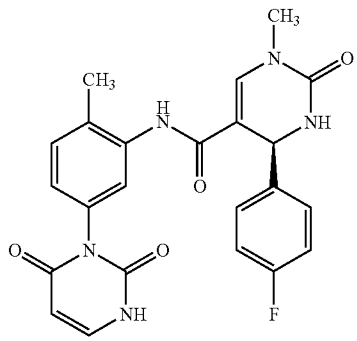 [SMILES: Cc1ccc(-n2c(=O)cc[nH]c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [5-(2,6-dioxo-3,6-dihydro-2H-pyrimidin-1-yl)-2-methyl-phenyl]-amide | 450 | 5.50 |
| 57 | 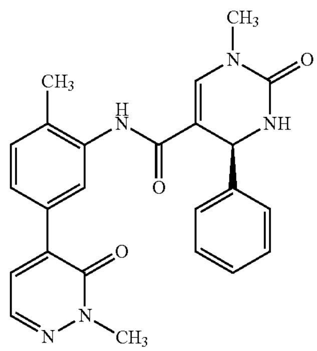 [SMILES: Cc1ccc(-c2ccnn(C)c2=O)cc1NC(=O)C1=CN(C)C(=O)N[C@H]1c1ccccc1] | (S)-1-Methyl-2-oxo-4-phenyl-1,2,3,4-tetrahydro-pyrimidine-5-carboxylic acid [2-methyl-5-(2-methyl-3-oxo-2,3-dihydro-pyridazin-4-yl)-phenyl]-amide | 430 | 5.46 |
| 58 | 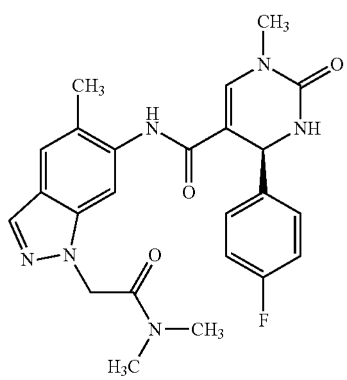 [SMILES: Cc1cc2cnn(CC(=O)N(C)C)c2cc1NC(=O)C1=CN(C)C(=O)N[C@H]1c1ccc(F)cc1] | S)-4-(4-Fluoro-phenyl)-1-methyl-2-oxo-1,2,3,4-tetrahydro-pyrimidine-5-carboxylic acid (1-dimethylcarbamoylmethyl-5-methyl-1H-imidazol-6-yl)-amide | 465 | 7.395 |
| 59 | 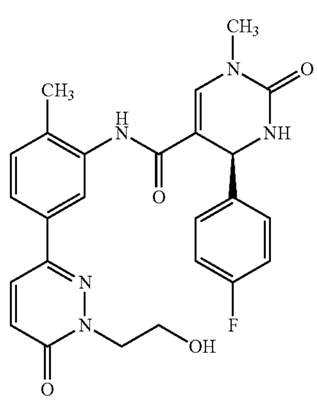 [SMILES: Cc1ccc(-c2ccc(=O)n(CCO)n2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid {5-[1-(2-hydroxy-ethyl)-6-oxo-1,6-dihydro-pyridazin-3-yl]-2-methyl-phenyl}-amide | 478 | 7.775 |

TABLE 1-continued

| # | Structure | Name (Autonom) | M + H | pIC$_{50}$ |
|---|---|---|---|---|
| 60 | 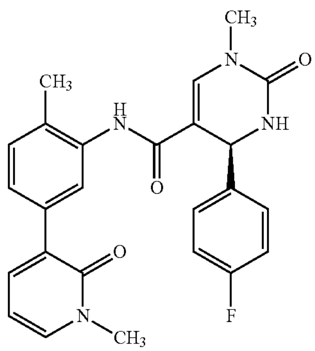 [SMILES: Cc1ccc(-c2cccn(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(1-methyl-2-oxo-1,2-dihydro-pyridin-3-yl)-phenyl]-amide | 447 | 8.26 |
| 61 | 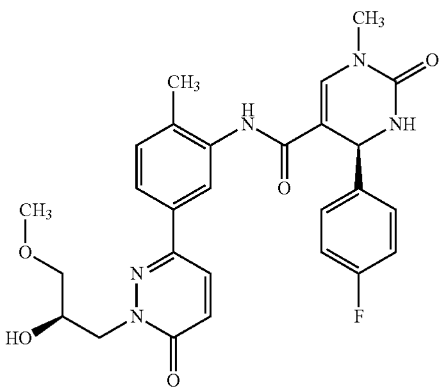 [SMILES: COC[C@H](O)Cn1nc(-c2ccc(C)c(NC(=O)C3=CN(C)C(=O)N[C@H]3c3ccc(F)cc3)c2)ccc1=O] | (S)-4-(4-Fluoro-phenyl)-1-methyl-2-oxo-1,2,3,4-tetrahydro-pyrimidine-5-carboxylic acid {5-[1-((R)-2-hydroxy-3-methoxy-propyl)-6-oxo-1,6-dihydro-pyridazin-3-yl]-2-methyl-phenyl}-amide | 522 | 7.39 |
| 62 | 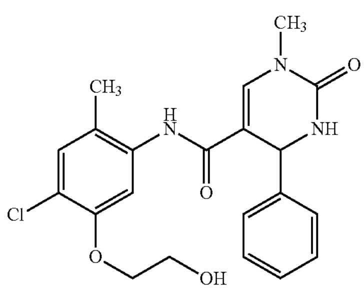 [SMILES: Cc1cc(Cl)c(OCCO)cc1NC(=O)C1=CN(C)C(=O)NC1c1ccccc1] | 1-Methyl-2-oxo-4-phenyl-1,2,3,4-tetrahydro-pyrimidine-5-carboxylic acid [4-chloro-5-(2-hydroxy-ethoxy)-2-methyl-phenyl]-amide | 417 | 7.825 |
| 63 | 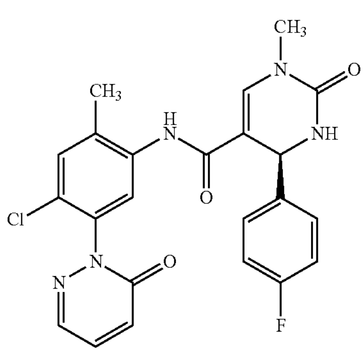 [SMILES: Cc1cc(Cl)c(-n2ncccc2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-chloro-2-methyl-5-(6-oxo-6H-pyridazin-1-yl)-phenyl]-amide | 469 | 7.285 |

| # | Structure | Name (Autonom) | M + H | pIC₅₀ |
|---|---|---|---|---|
| 64 | 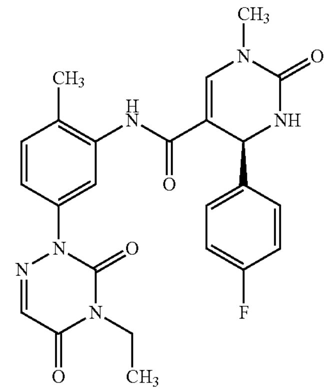 [SMILES: CCn1c(=O)cnn(-c2ccc(C)c(NC(=O)C3=CN(C)C(=O)N[C@H]3c3ccc(F)cc3)c2)c1=O] | (S)-4-(4-Fluoro-phenyl)-1-methyl-2-oxo-1,2,3,4-tetrahydro-pyrimidine-5-carboxylic acid [5-(4-ethyl-3,5-dioxo-4,5-dihydro-3H-[1,2,4]triazin-2-yl)-2-methyl-phenyl]-amide | 479 | 7.78 |
| 65 | 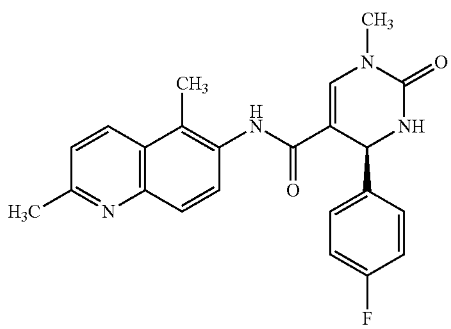 [SMILES: Cc1ccc2c(C)c(NC(=O)C3=CN(C)C(=O)N[C@H]3c3ccc(F)cc3)ccc2n1] | (S)-4-(4-Fluoro-phenyl)-1-methyl-2-oxo-1,2,3,4-tetrahydro-pyrimidine-5-carboxylic acid (2,5-dimethyl-quinolin-6-yl)-amide | 405 | 7.81 |
| 66 | 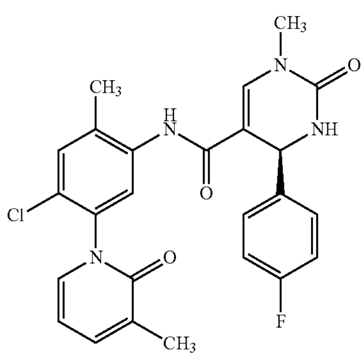 [SMILES: Cc1cc(Cl)c(-n2cccc(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-chloro-2-methyl-5-(3-methyl-2-oxo-2H-pyridin-1-yl)-phenyl]-amide | 482 | 7.71 |
| 67 | 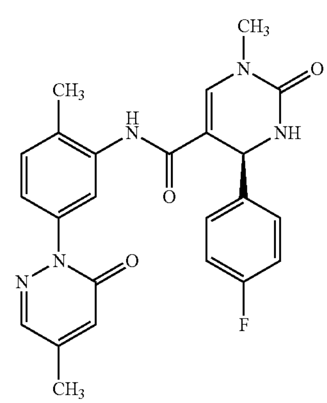 [SMILES: Cc1cnn(-c2ccc(C)c(NC(=O)C3=CN(C)C(=O)N[C@H]3c3ccc(F)cc3)c2)c(=O)c1] | (S)-4-(4-Fluoro-phenyl)-1-methyl-2-oxo-1,2,3,4-tetrahydro-pyrimidine-5-carboxylic acid [2-methyl-5-(4-methyl-6-oxo-6H-pyridazin-1-yl)-phenyl]-amide | 448 | |

TABLE 1-continued

| # | Structure | Name (Autonom) | M + H | pIC$_{50}$ |
|---|---|---|---|---|
| 68 | 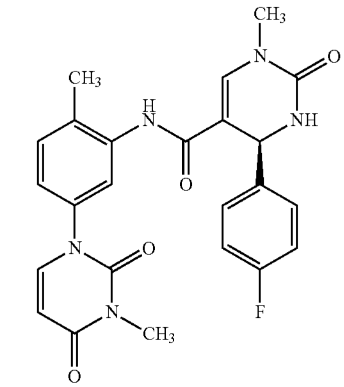 [SMILES: Cc1ccc(-n2ccc(=O)n(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [2-methyl-5-(3-methyl-2,4-dioxo-3,4-dihydro-2H-pyrimidin-1-yl)-phenyl]-amide | 464 | 7.425 |
| 69 | 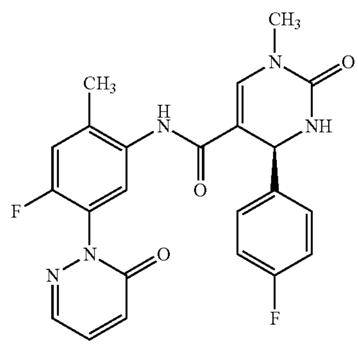 [SMILES: Cc1cc(F)c(-n2ncccc2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-fluoro-2-methyl-5-(6-oxo-6H-pyridazin-1-yl)-phenyl]-amide | 452 | 7.715 |
| 70 | 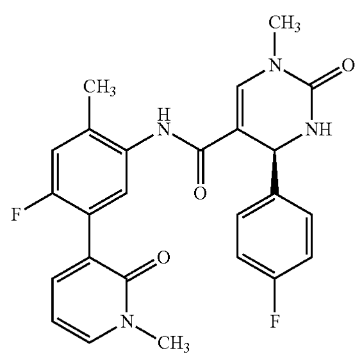 | (S)-4-(4-Fluoro-phenyl)-1-methyl-2-oxo-1,2,3,4-tetrahydro-pyrimidine-5-carboxylic acid [4-fluoro-2-methyl-5-(1-methyl-2-oxo-1,2-dihydro-pyridin-3-yl)-phenyl]-amide | 465 | 7.48 |
| 71 | 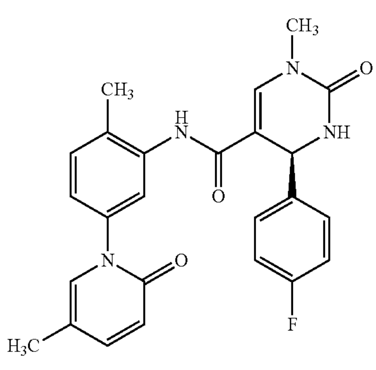 | (S)-4-(4-Fluoro-phenyl)-1-methyl-2-oxo-1,2,3,4-tetrahydro-pyrimidine-5-carboxylic acid [2-methyl-5-(5-methyl-2-oxo-2H-pyridin-1-yl)-phenyl]-amide | 447 | 7.365 |

TABLE 1-continued

| # | Structure | Name (Autonom) | M + H | pIC$_{50}$ |
|---|---|---|---|---|
| 72 | 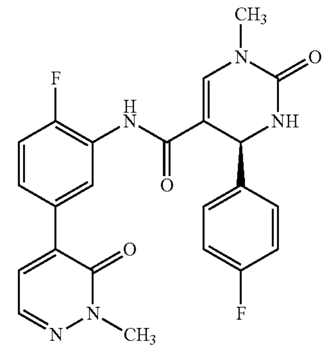 [SMILES: CN1C=C(C(=O)Nc2cc(-c3ccnn(C)c3=O)ccc2F)[C@H](c2ccc(F)cc2)NC1=O] | (S)-4-(4-Fluoro-phenyl)-1-methyl-2-oxo-1,2,3,4-tetrahydro-pyrimidine-5-carboxylic acid [2-fluoro-5-(2-methyl-3-oxo-2,3-dihydro-pyridazin-4-yl)-phenyl]-amide | 452 | 7.8033 |
| 73 | 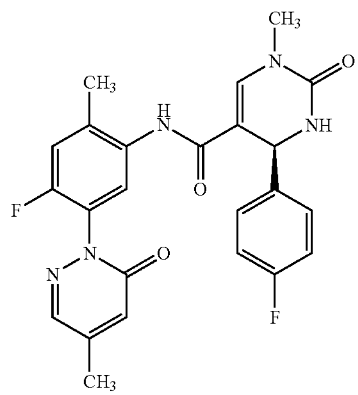 [SMILES: Cc1cnn(-c2cc(NC(=O)C3=CN(C)C(=O)N[C@H]3c3ccc(F)cc3)c(C)cc2F)c(=O)c1] | (S)-4-(4-Fluoro-phenyl)-1-methyl-2-oxo-1,2,3,4-tetrahydro-pyrimidine-5-carboxylic acid [4-fluoro-2-methyl-5-(4-methyl-6-oxo-6H-pyridazin-1-yl)-phenyl]-amide | 466 | 7.245 |
| 74 | 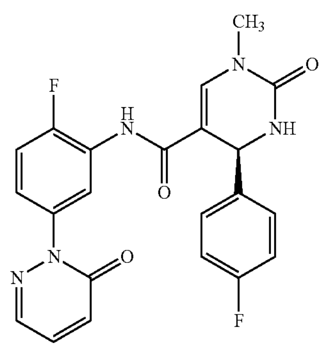 [SMILES: CN1C=C(C(=O)Nc2cc(-n3ncccc3=O)ccc2F)[C@H](c2ccc(F)cc2)NC1=O] | (S)-4-(4-Fluoro-phenyl)-1-methyl-2-oxo-1,2,3,4-tetrahydro-pyrimidine-5-carboxylic acid [2-fluoro-5-(6-oxo-6H-pyridazin-1-yl)-phenyl]-amide | 437 | 6.995 |
| 75 | 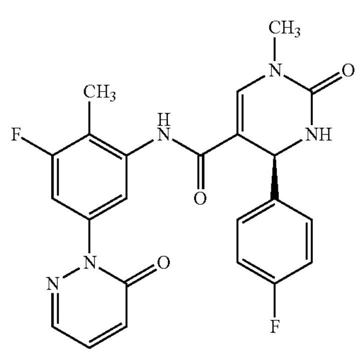 [SMILES: Cc1c(F)cc(-n2ncccc2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [3-fluoro-2-methyl-5-(6-oxo-6H-pyridazin-1-yl)-phenyl]-amide | 452 | |

TABLE 1-continued

| # | Structure | Name (Autonom) | M + H | pIC$_{50}$ |
|---|---|---|---|---|
| 76 | 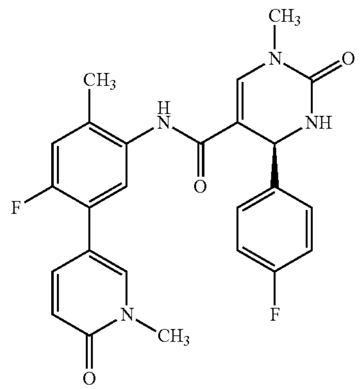 [SMILES: Cc1cc(F)c(-c2ccc(=O)n(C)c2)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-fluoro-2-methyl-5-(1-methyl-6-oxo-1,6-dihydro-pyridin-3-yl)-phenyl]-amide | 465 | |
| 77 | 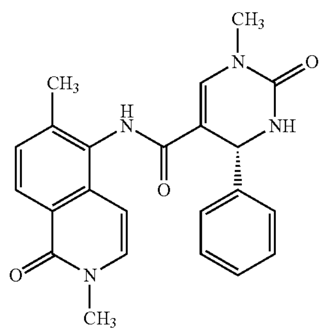 [SMILES: Cc1ccc2c(=O)n(C)ccc2c1NC(=O)C1=CN(C)C(=O)N[C@@H]1c1ccccc1] | (R)-1-Methyl-2-oxo-4-phenyl-1,2,3,4-tetrahydro-pyrimidine-5-carboxylic acid (2,6-dimethyl-1-oxo-1,2-dihydro-isoquinolin-5-yl)-amide | 403 | |
| 78 | 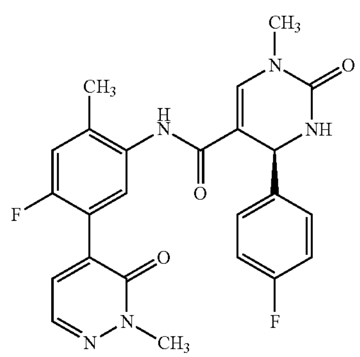 [SMILES: Cc1cc(F)c(-c2ccnn(C)c2=O)cc1NC(=O)C1=CN(C)C(=O)N[C@H]1c1ccc(F)cc1] | (S)-4-(4-Fluoro-phenyl)-1-methyl-2-oxo-1,2,3,4-tetrahydro-pyrimidine-5-carboxylic acid [4-fluoro-2-methyl-5-(2-methyl-3-oxo-2,3-dihydro-pyridazin-4-yl)-phenyl]-amide | 466 | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein R is lower alkyl and may be the same or different upon each occurrence, and p, $R^6$, $R^7$, $R^8$, $R^9$, $R^{10}$ and $R^{11}$ are as defined herein.

SCHEME A

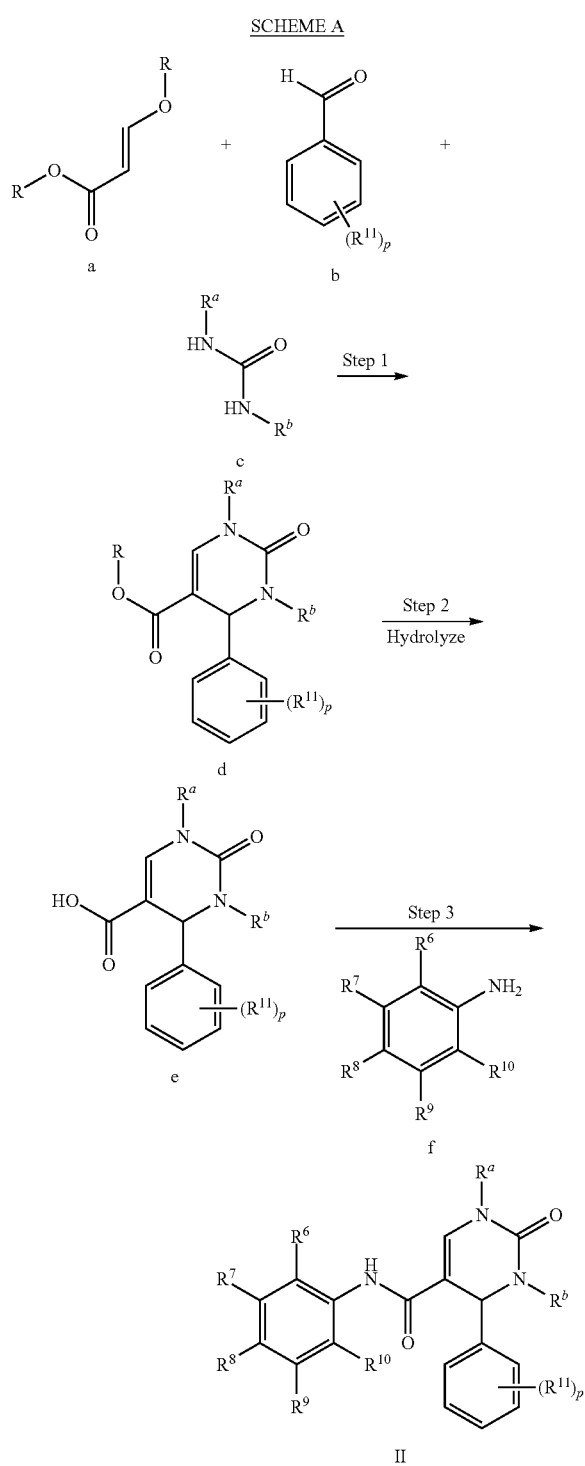

In step 1 of Scheme A, a Bignelli-type reaction is carried out by reaction of alkoxy acrylate a, benzaldehyde b and urea c, to afford pyrimidone ester compound d. The reaction of step 1 may be under polar aprotic solvent conditions and in the presence of a catalyst such as $SiO_2$—$NaHSO_4$.

In step 2, ester compound d is hydrolized to the corresponding pyrimidone acid compound e. The reaction of step 2 may occur, for example, in the presence of base under polar protic solvent conditions.

An amide coupling reaction in step 3 between pyrimidone acid e and aniline compound f yields pyrimidone amide compound II, which is a compound of formula I in accordance with the invention. The reaction of step 3 may be facilitated by formation of the acid chloride (not shown) of compound e prior to reaction with aniline f. In other embodiments the amide coupling of step 3 may be achieved in the presence of a EDCI, HATU, BOP, PyBOP or other amide coupling reagent.

Many variations on the procedure of Scheme A are possible and will suggest themselves to those skilled in the art. For example, in certain embodiments alkylation of amide compound II may be carried out to introduce groups $R^a$ and $R^b$ other than hydrogen. Selective deuteration and/or tritiation of portions of the compounds disclosed herein may be carried out to modify metabolic and pharmacokinetic properties of the compounds, as will be readily apparent to those skilled in the art. Specific details for producing compounds of the invention are described in the Examples section below.

Utility

The compounds of the invention are usable for the treatment of a wide range of inflammatory diseases and conditions such as arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. The subject compounds would be useful for the treatment of pulmonary disorders or lung inflammation, including adult respiratory distress syndrome, pulmonary sarcoidosis, asthma, silicosis, and chronic pulmonary inflammatory disease.

The compounds of the invention are also expected to find utility as analgesics in the treatment of diseases and conditions associated with pain from a wide variety of causes, including, but not limited to, inflammatory pain such as pain associated with arthritis (including rheumatoid arthritis and osteoarthritis), surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

The compounds of the invention are also useful for the treatment of muscular sclerosis and diabetes.

The compounds of the invention further are useful in the treatment of memory disorders such as Alzheimer's disease, and the enhancement of cognitive memory.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

| ABBREVIATIONS | |
|---|---|
| BETBDMS | 2-bromoethoxy tertbutyldimethylsilane |
| DBU | 1,8-diazabicyclo[5.4.0]undec-7-ene |
| DCM | dichloromethane/methylene chloride |
| DIPEA | diisopropyl ethylamine (Hunig's base) |
| DME | 1,2-dimethoxyethane (glyme) |
| DMF | N,N-dimethylformamide |
| DMFDMA | N,N-dimethylformamide dimethyl acetal |
| DMSO | dimethyl sulfoxide |
| DMAP | 4-dimethylaminopyridine |
| dppf | 1,1'-Bis(diphenylphosphino)ferrocene |
| EDCI | 1-ethyl-3-(3'-dimethylaminopropyl)carbodiimide |
| EtOAc | ethyl acetate |
| EtOH | ethanol |
| gc | gas chromatography |
| HATU | O-(7-Azabenzotriazol-1-yl)-N,N,N',N'-tetramethyluronium hexafluorophosphate |
| HMPA | hexamethylphosphoramide |
| HOAc | acetic acid |
| HOBt | N-Hydroxybenzotriazole |
| hplc | high performance liquid chromatography |
| IPA | isopropanol |
| IPBAPE | isopropenylboronic acid pinacol ester |
| mCPBA | m-chloroperbenzoic acid |
| MeCN | acetonitrile |
| NMM | N-methyl morpholine |
| NMP | N-methyl pyrrolidinone |
| Pd$_2$(dba)$_3$ | Tris(dibenzylideneacetone)dipalladium(0) |
| TBAF | tetra-n-butyl ammonium fluoride |
| tBDMSICl | tert-butyl-dimethylsilyl chloride |
| TEA | triethylamine |
| THF | tetrahydrofuran |
| LDA | lithium diisopropylamine |
| TBDMS | tert-butyl dimethylsilyl chloride |
| TLC | thin layer chromatography |
| Xantphos | 4,5-bis(diphenylphosphino)-9,9-dimethyl-xanthene |

Preparation 1

(R) and (S) 4-(4-Fluoro-phenyl)-2-oxo-1,2,3,4-tetrahydro-pyrimidine-5-carboxylic acid The synthetic procedure used in this preparation is outlined in Scheme B.

SCHEME B

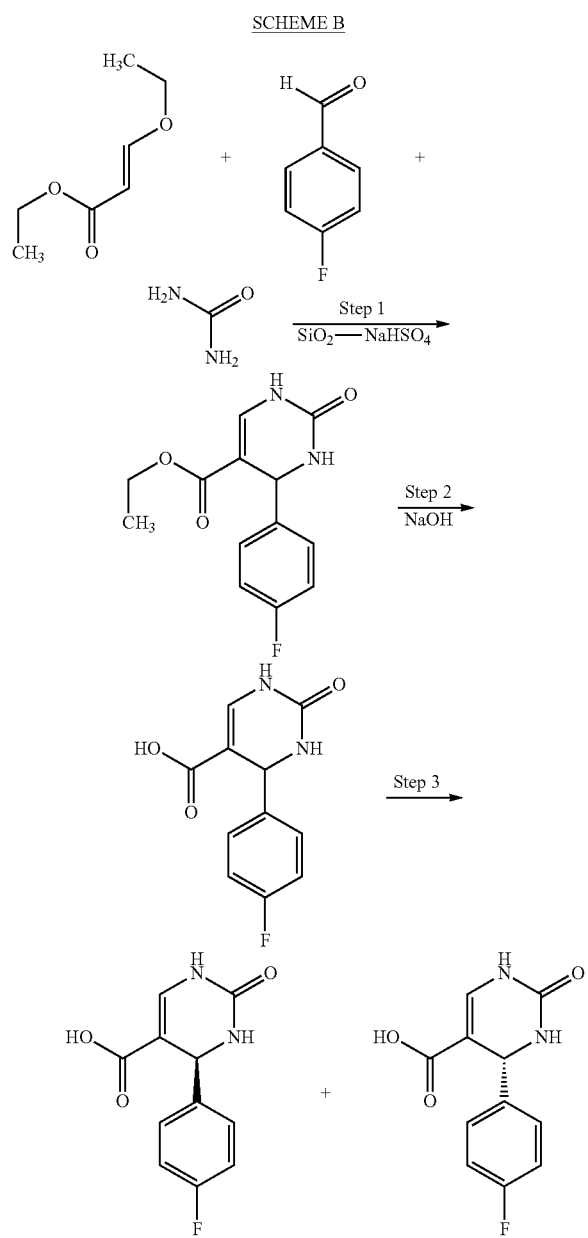

Step 1 4-(4-Fluoro-phenyl)-2-oxo-1,2,3,4-tetrahydro-pyrimidine-5-carboxylic acid ethyl ester 4-(4-Fluoro-phenyl)-2-oxo-1,2,3,4-tetrahydro-pyrimidine-5-carboxylic acid ethyl ester was prepared using the Biginelli reaction following the procedure reported in WO 2007/101213). Briefly, to a solution of p-fluorobenzaldehyde (7.5 mL) in 200 mL acetonitrile was added ethyl 3-ethoxyacrylate (10.7 mL), urea (5.0 g) and freshly dried $SiO_2$—$NaHSO_4$ (3.7 g). The solution was heated at reflux for 18 hours, then cooled and poured into ice water. The precipitate was recovered by filtration and air-dried to yield 4-(4-fluoro-phenyl)-2-oxo-1,2,3,4-tetrahydro-pyrimidine-5-carboxylic acid ethyl ester (18.8 g).

Similarly prepared, using methyl urea instead of urea, was 4-(4-fluoro-phenyl)-1-methyl-2-oxo-1,2,3,4-tetrahydro-pyrimidine-5-carboxylic acid ethyl ester.

Step 2 4-(4-Fluoro-phenyl)-2-oxo-1,2,3,4-tetrahydro-pyrimidine-5-carboxylic acid 4-(4-Fluoro-phenyl)-2-oxo-1,2,3,4-tetrahydro-pyrimidine-5-carboxylic acid ethyl ester (3.6 g) was suspended in 67 mL MeOH and 2.5 M NaOH (23 mL) was added. The mixture was heated at 65° for 6 hours, then cooled, diluted with water and acidified with conc. HCl. The resulting precipitate was recovered by filtration and air dried to yield 4-(4-fluoro-phenyl)-2-oxo-1,2,3,4-tetrahydro-pyrimidine-5-carboxylic acid (2.3 g).

Similarly prepared, from 4-(4-fluoro-phenyl)-1-methyl-2-oxo-1,2,3,4-tetrahydro-pyrimidine-5-carboxylic acid ethyl ester, was 4-(4-fluoro-phenyl)-1-methyl-2-oxo-1,2,3,4-tetrahydro-pyrimidine-5-carboxylic acid.

Step 3 Chiral Separation of (R) and (S) 4-(4-Fluoro-phenyl)-2-oxo-1,2,3,4-tetrahydro-pyrimidine-5-carboxylic acid Racemic 4-(4-fluoro-phenyl)-2-oxo-1,2,3,4-tetrahydro-pyrimidine-5-carboxylic acid was chromatographed on an R.R. Whelk-0 (Regis Technologies) chiral 30 mm supercritical fluid chromatography column, 20% MeOH in liquid $CO_2$, at 70 mL/minute. The (S) isomer ($alpha_{[D]}$=+139) was obtained from a first fraction and the (R) isomer ($alpha_{[D]}$=−143.3) from a second fraction.

Preparation 2

4-(4-Fluoro-phenyl)-1-methyl-2-oxo-1,2,3,4-tetrahydro-pyrimidine-5-carboxylic acid and 4-(4-Fluoro-phenyl)-1,3-dimethyl-2-oxo-1,2,3,4-tetrahydro-pyrimidine-5-carboxylic acid The synthetic procedure used in this preparation is outlined in Scheme C.

SCHEME C

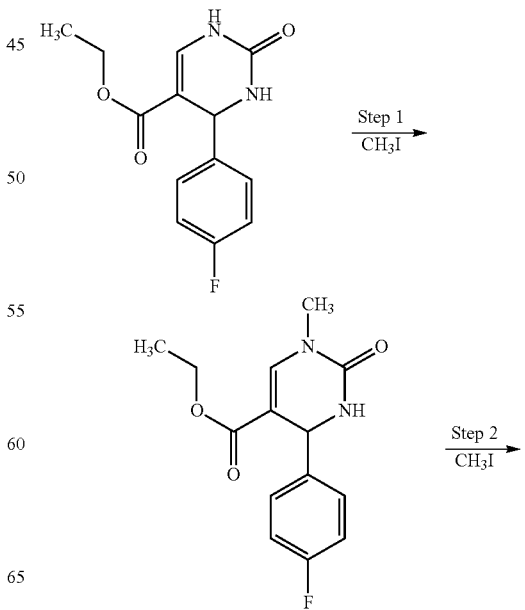

81

-continued

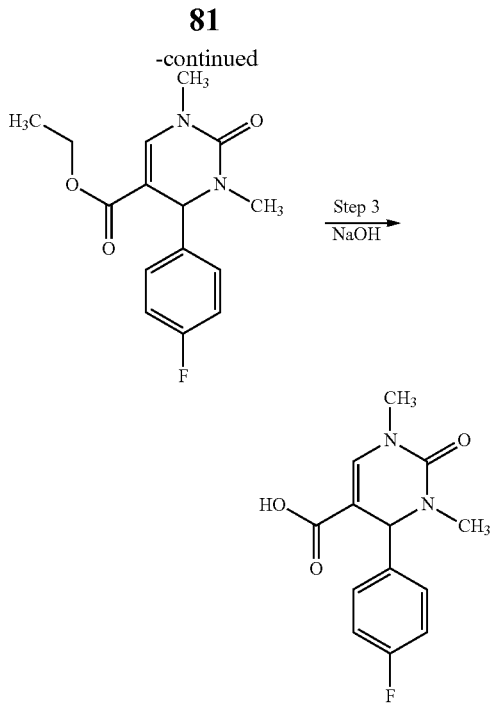

Step 1 4-(4-Fluoro-phenyl)-1-methyl-2-oxo-1,2,3,4-tetrahydro-pyrimidine-5-carboxylic acid ethyl ester 4-(4-Fluoro-phenyl)-2-oxo-1,2,3,4-tetrahydro-pyrimidine-5-carboxylic acid ethyl ester (6 g, from Preparation 1), $CsCO_3$ (7.5 g) was added to 50 mL of DMF, followed by $CH_3I$ (1.5 mL). The mixture was heated at 60° for 18 hours, then cooled to room temperature and poured into ice water. The resulting precipitate was recovered by filtration and air-dried to give 5.6 g of 4-(4-fluoro-phenyl)-1-methyl-2-oxo-1,2,3,4-tetrahydro-pyrimidine-5-carboxylic acid ethyl ester.

Similarly, but replacing $CH_3I$ with 2-bromoethoxy dimethyl-t-butyl silane, 1-[2-(tert-butyl-dimethyl-silanyloxy)-ethyl]-4-(4-fluoro-phenyl)-2-oxo-1,2,3,4-tetrahydro-pyrimidine-5-carboxylic acid ethyl ester was prepared.

Step 2 4-(4-Fluoro-phenyl)-1,3-dimethyl-2-oxo-1,2,3,4-tetrahydro-pyrimidine-5-carboxylic acid ethyl ester 4-(4-Fluoro-phenyl)-1-methyl-2-oxo-1,2,3,4-tetrahydro-pyrimidine-5-carboxylic acid ethyl ester (1.0 g, 3.6 mmol) was dissolved in 10 mL DMF and cooled to 0°. Potassium hexamethyldisilazane (8 mL, 4 mmol of 0.5M toluene solution) was added and the reaction mixture was stirred at 0° for 5 minutes. $CH_3I$ (0.3 mL, 4.8 mmol) was added and the mixture was allowed to warm to room temperature and stir for 2 hours. The solution was poured into cold aqueous pH 2 buffer and extracted with ethyl acetate. The organic layer was dried over $Na_2SO_4$, filtered and the solvent removed in vacuo. The residue was chromatographed in 0-30% ethyl acetate/hexane to yield 700 mg of 4-(4-fluoro-phenyl)-1,3-dimethyl-2-oxo-1,2,3,4-tetrahydro-pyrimidine-5-carboxylic acid ethyl ester.

82

Step 3 4-(4-Fluoro-phenyl)-1-methyl-2-oxo-1,2,3,4-tetrahydro-pyrimidine-5-carboxylic acid 4-(4-Fluoro-phenyl)-1,3-dimethyl-2-oxo-1,2,3,4-tetrahydro-pyrimidine-5-carboxylic acid ethyl ester (700 mg) was dissolved in a mixture of 20 mL methanol and 6 mL 10% aqueous NaOH and heated at 45° for 3 hours. The reaction mixture was cooled to room temperature and acidified with conc. HCl. The resulting precipitate and collected by filtration and air-dried to give 4-(4-Fluoro-phenyl)-1-methyl-2-oxo-1,2,3,4-tetrahydro-pyrimidine-5-carboxylic acid.

4-(4-Fluoro-phenyl)-1-methyl-2-oxo-1,2,3,4-tetrahydro-pyrimidine-5-carboxylic acid ethyl ester from step 1 was similarly hydrolized to give 4-(4-fluoro-phenyl)-1-methyl-2-oxo-1,2,3,4-tetrahydro-pyrimidine-5-carboxylic acid. The 4-(4-fluoro-phenyl)-1-methyl-2-oxo-1,2,3,4-tetrahydro-pyrimidine-5-carboxylic acid was separated into (S) enantiomer (first fraction, $alph_{[D]}$=+142.1 and (R) enantiomer were separated using the procedure of Step 3 of Example 1.

Similarly, hydrolysis of 1-[2-(tert-butyl-dimethyl-silanyloxy)-ethyl]-4-(4-fluoro-phenyl)-2-oxo-1,2,3,4-tetrahydro-pyrimidine-5-carboxylic acid ethyl ester afforded 4-(4-fluoro-phenyl)-1-(2-hydroxy-ethyl)-2-oxo-1,2,3,4-tetrahydro-pyrimidine-5-carboxylic acid.

Preparation 3

4-(4-Fluoro-phenyl)-3-methyl-2-oxo-1,2,3,4-tetrahydro-pyrimidine-5-carboxylic acid The synthetic procedure used in this preparation is outlined in Scheme D.

SCHEME D

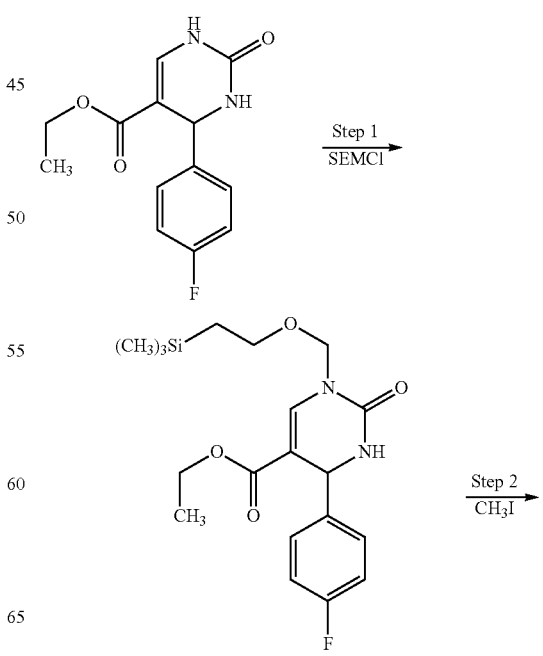

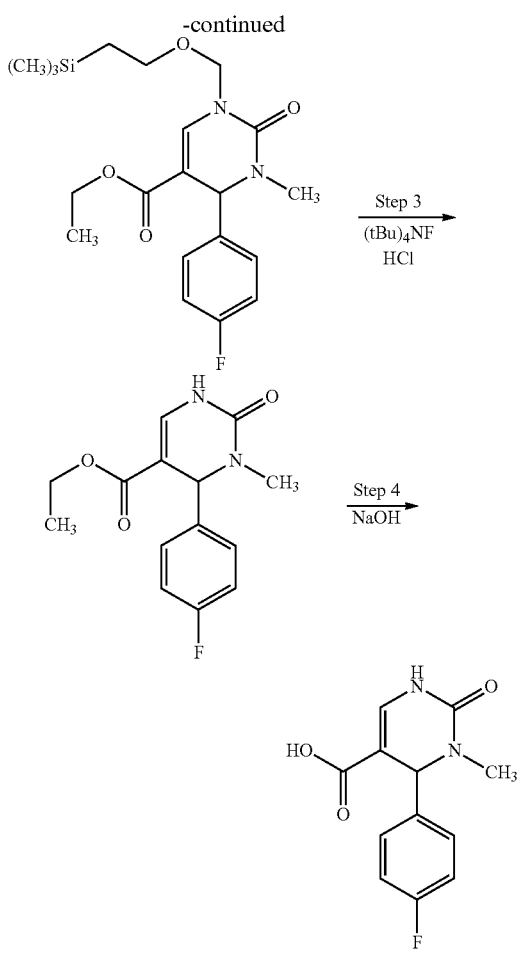

Step 1 4-(4-Fluoro-phenyl)-2-oxo-1-propoxymethyl-1,2,3,4-tetrahydro-pyrimidine-5-carboxylic acid ethyl ester To a solution of 4-(4-fluoro-phenyl)-2-oxo-1,2,3,4-tetrahydro-pyrimidine-5-carboxylic acid ethyl ester (205 mg, 0.78 mmol) in THF (3 mL) was added lithium hexamethyldisilazide (LiHMDS, 0.78 mL of 1M THF solution, 0.78 mmol) at 0° C. under argon atmosphere. The reaction mixture was stirred for 10 minutes, and then 2-trimethylsilylethyoxymethyl chloride (SEMCl, 0.137 mL, 0.78 mmol) was added dropwise at 0° C. The mixture was allowed to reach rt and was stirred overnight. Saturated aqueous $NH_4Cl$ was added and the mixture was extracted with ethyl acetate. The combined organic extracts were washed with brine, dried under $Na_2SO_4$, filtered and concentrated to dryness under reduced pressure. Purification of the residue by flash column (hexane/ethyl acetate gradient) gave 4-(4-fluoro-phenyl)-2-oxo-1-propoxymethyl-1,2,3,4-tetrahydro-pyrimidine-5-carboxylic acid ethyl ester (155 mg, 51%).

Step 2 4-(4-Fluoro-phenyl)-3-methyl-2-oxo-1-propoxymethyl-1,2,3,4-tetrahydro-pyrimidine-5-carboxylic acid ethyl ester To a solution of 4-(4-Fluoro-phenyl)-2-oxo-1-propoxymethyl-1,2,3,4-tetrahydro-pyrimidine-5-carboxylic acid ethyl ester (152 mg, 0.39 mmol) in THF (3 mL) was added potassium hexamethyldisilazane (0.92 mL of 1M toluene solution, 0.46 mmol) at 0° C. under Ar. The mixture was stirred for 1 h at 0° C. Methyl iodide (0.23 mL of 2M solution in tert-butyl methyl ether) was added at 0° C., and the mixture was stirred at 0° C. overnight. Saturated aqueous $NH_4Cl$ was added, and the mixture was extracted with ethyl acetate. The combined organic layers were washed with brine, dried under $Na_2SO_4$, filtered and concentrated to dryness under reduced pressure. Purification of the residue by flash column (hexane/ethyl acetate gradient) gave 4-(4-fluoro-phenyl)-3-methyl-2-oxo-1-propoxymethyl-1,2,3,4-tetrahydro-pyrimidine-5-carboxylic acid ethyl ester (143 mg, 91%).

Step 3 4-(4-Fluoro-phenyl)-3-methyl-2-oxo-1,2,3,4-tetrahydro-pyrimidine-5-carboxylic acid ethyl ester Tetrabutylammonium fluoride (2.1 mL of 1M solution in THF, 2.1 mmol) was added to 4-(4-fluoro-phenyl)-3-methyl-2-oxo-1-propoxymethyl-1,2,3,4-tetrahydro-pyrimidine-5-carboxylic acid ethyl ester (140 mg, 0.34 mmol) under Ar. The mixture was heated at 65° C. overnight, then cooled. HCl (2N aqueous solution) was added and the mixture was extracted with diethyl ether. The combined extracts were washed with water and brine, dried on $Na_2SO_4$, filtered, and concentrated to dryness under reduced pressure. Purification by flash column (hexane/ethyl acetate gradient) gave 4-(4-fluoro-phenyl)-3-methyl-2-oxo-1,2,3,4-tetrahydro-pyrimidine-5-carboxylic acid ethyl ester (92 mg, 97%).

Step 4 4-(4-Fluoro-phenyl)-3-methyl-2-oxo-1,2,3,4-tetrahydro-pyrimidine-5-carboxylic acid 4-(4-Fluoro-phenyl)-3-methyl-2-oxo-1,2,3,4-tetrahydro-pyrimidine-5-carboxylic acid ethyl ester was hydrolyzed following the procedure of step 3 of Preparation 2 to give –(4-fluoro-phenyl)-3-methyl-2-oxo-1,2,3,4-tetrahydro-pyrimidine-5-carboxylic acid.

Preparation 4

5-[2-(tert-Butyl-dimethyl-silanyloxy)-ethoxy]-4-chloro-2-methyl-phenylamine

The synthetic procedure used in this preparation is outlined in Scheme D.

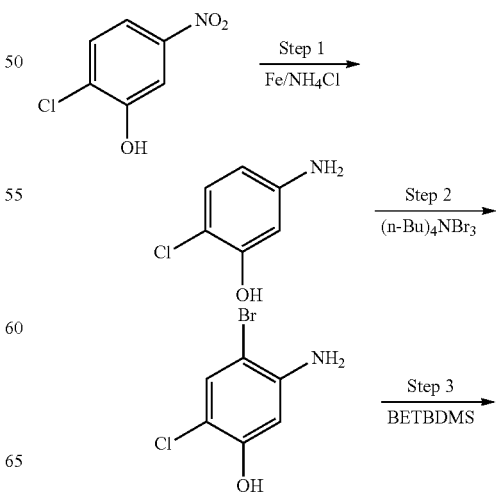

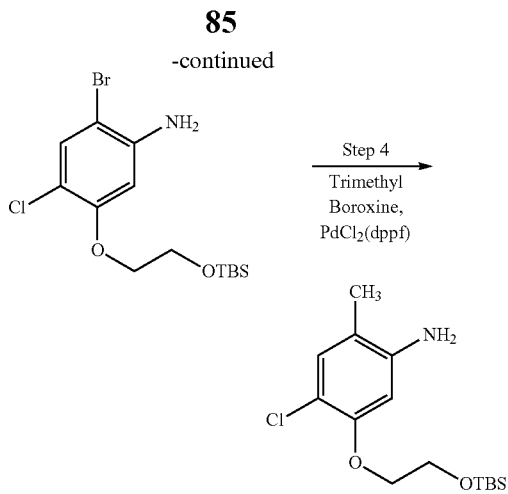

Step 1 5-Amino-2-chloro-phenol

To a solution of 2-chloro-5-nitrophenol (20.0 g, 115.2 mmol) in ethanol (150 ml) and water (150 ml) was added iron powder (32.2 g, 576.2 mmol) and ammonium chloride (32.1 g, 599.3 mmol). The mixture was heated at reflux for two hours, then cooled to room temperature and filtered. The filtrate was concentrated to dryness under reduced pressure. Purification of the residue by flash chromatography (hex:EtOAc/9:1) gave 5-amino-2-chloro-phenol (15.85 g, 96%) as a white solid.

Step 2 5-Amino-4-bromo-2-chloro-phenol

To a solution of 5-amino-2-chloro-phenol (15.85 g, 110.4 mmol) in dichloromethane (300 ml) and MeOH (150 ml) was added tetrabutylammonium tribromide (58.6 g, 121.4 mmol). The mixture was stirred at room temperature for 20 minutes, and then was partitioned between saturated aqueous $Na_2SO_3$ and $Et_2O$. The organic layer was separated, washed with water and brine, dried over $MgSO_4$, filtered and concentrated to dryness under reduced pressure. Purification of the residue by flash chromatography (hex:EtOAc/7:3) gave 5-amino-4-bromo-2-chloro-phenol (4.38 g, 18%) as a white solid.

Step 3 2-Bromo-5-[2-(tert-butyl-dimethyl-silanyloxy)-ethoxy]-4-chloro-phenylamine To a solution of 5-amino-4-bromo-2-chloro-phenol (0.338 g, 1.52 mmol) in NMP (5 ml) was added cesium carbonate (0.644 g, 1.97 mmol), sodium iodide (0.228 g, 1.52 mmol) and 2-bromoethoxy tertbutyldimethylsilane (0.424 g, 1.97 mmol). The mixture was heated to 100° C. for two hours, then cooled to room temperature. Water was added and the mixture was extracted with EtOAc. The combined organic extracts were washed with water and brine, dried over $MgSO_4$, filtered and concentrated to dryness under reduced pressure. Purification of the residue by flash chromatography (hex:EtOAc/8:2) gave 2-bromo-5-[2-(tert-butyl-dimethyl-silanyloxy)-ethoxy]-4-chloro-phenylamine (0.505 g, 78%) as a white solid.

Step 4 5-[2-(tert-Butyl-dimethyl-silanyloxy)-ethoxy]-4-chloro-2-methyl-phenylamine To a solution of 2-bromo-4-chloro-5 (2-dimethyl-tert-butylsiloxyethyl)-oxy aniline (6.5 g, 17.07 mmol) in Dioxane (120 ml)-Water (12 ml) under Ar atmosphare was added potassium carbonate (7.08 g, 51.2 mmol), trimethylboroxine (2.408 ml, 17.07 mmol) and $PdCl_2(dppf)$-$CH_2Cl_2$ (1.394 g, 1.707 mmol). The mixture was heated to 110° C. for 20 hours, then cooled to room temperature and filtered through Celite. Water and EtOAc were added, and the organic layer was separated, washed with water and brine, dried ($Na_2SO_4$), filtered and concentrated under reduced pressure. The crude product was purified by flash chromatography (0 to 20% EtOAc in hexanes to give 3.66 g of 5-[2-(tert-butyl-dimethyl-silanyloxy)-ethoxy]-4-chloro-2-methyl-phenylamine as a white solid. Recrystallization from EtOAc gave 2.35 g of 5-[2-(tert-butyl-dimethyl-silanyloxy)-ethoxy]-4-chloro-2-methyl-phenylamine as white crystals.

Similarly prepared was 5-[2-(tert-butyl-dimethyl-silanyloxy)-ethoxy]-4-fluoro-2-methyl-phenylamine

Preparation 5

3-(5-Amino-2-fluoro-4-methyl-phenyl)-5-methyl-pyrazole-1-carboxylic acid benzyl ester The synthetic procedure used in this preparation is outlined in Scheme E.

SCHEME E

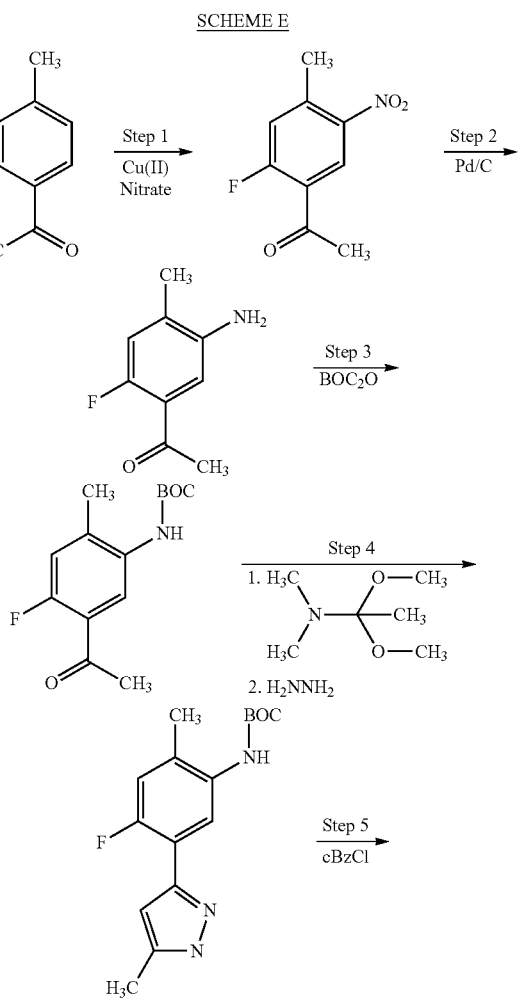

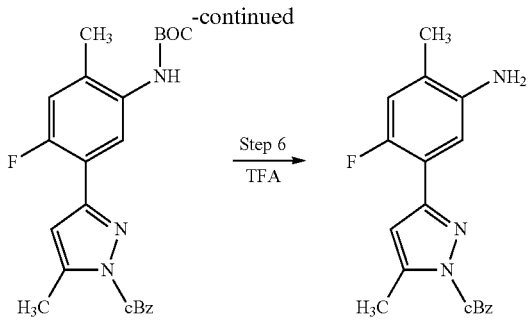

Step 1
1-(2-Fluoro-4-methyl-5-nitro-phenyl)-ethanone

Copper (II) nitrate (3.175 g) was added portion wise to a room temperature solution of 1-(2-fluoro-4-methyl-phenyl)-ethanone (2.74 g) in chloroform (30 ml) and Trifluoroacetic anhydride. The mixture was heated at 60° C. for 30 minutes then cooled to room temperature and added to ice. The mixture was extracted with methylene chloride, and the organic layer was washed with water and brine, dried ($Na_2SO_4$), filtered and concentrated under reduced pressure to give 3.17 g of 1-(2-Fluoro-4-methyl-5-nitro-phenyl)-ethanone as a reddish oil, which was used directly without further purification.

Step 2
1-(5-Amino-2-fluoro-4-methyl-phenyl)-ethanone 1-(2-Fluoro-4-methyl-5-nitro-phenyl)-ethanone (3.17 g) in ethanol (10 ml) was hydrogenated over Pd/C (200 mg) under balloon pressure over night. The mixture was filtered and the filtrate was concentrated under reduced pressure to a grey solid that was recrystallized (EtOAc Hexane) to give 1.625 g of 1-(5-amino-2-fluoro-4-methyl-phenyl)-ethanone as an off-white powder.

Step 3
(5-Acetyl-4-fluoro-2-methyl-phenyl)-carbamic acid tert-butyl ester "BOC" anhydride (2.451 g) was added in one portion to a 0° C. solution of 1-(5-amino-2-fluoro-4-methyl-phenyl)-ethanone (1.625 g) and DMAP (20 mg) in THF (10 ml). The reaction mixture was stirred at room temperature for 20 hours, then concentrated under reduced pressure. "Flash chromatography" 0 to 30% EtOAc in hexanes gave (5-Acetyl-4-fluoro-2-methyl-phenyl)-carbamic acid tert-butyl ester (2.45 g) as a white solid.

Step 4 [4-Fluoro-2-methyl-5-(5-methyl-1H-pyrazol-3-yl)-phenyl]-carbamic acid tert-butyl ester A solution of (5-Acetyl-4-fluoro-2-methyl-phenyl)-carbamic acid tert-butyl ester (425 mg) and (1,1-dimethoxy-ethyl)-dimethyl-amine (653 mg) in DMF (2 ml) was heated at 90° C. for 3 hours, then cooled to room temperature. Solvent was removed under reduced pressure, and the residue was dissolved in a mixture of EtOH (25 ml) and THF (5 ml). The mixture was cooled to 0° C., and hydrazine hydrate (5 ml) at 0° C. was added. The mixture was stirred for 16 hours at room temperature, then concentrated under reduced pressure. The residue was purified by "flash chromatography" (0 to 30% EtOAc in hexanes) to give 370 mg of [4-fluoro-2-methyl-5-(5-methyl-1H-pyrazol-3-yl)-phenyl]-carbamic acid tert-butyl ester.

Step 5 3-(5-tert-Butoxycarbonylamino-2-fluoro-4-methyl-phenyl)-5-methyl-2H-pyrazole-1-carboxylic acid benzyl ester Benzylchloroformate (104 mg) was added dropwise to a room temperature solution of [4-fluoro-2-methyl-5-(5-methyl-1H-pyrazol-3-yl)-phenyl]-carbamic acid tert-butyl ester and DIPEA in $CH_2Cl_2$ (2 ml). The mixture was stirred at room temperature for one hour, and then 10% aqueous citric acid solution was added. The organic layer was separated dried ($Na_2SO_4$), filtered and concentrated under reduced pressure. "Flash chromatography" of the residue (0 to 20% EtOAc in hexanes) gave 210 mg of 3-(5-tert-Butoxycarbonylamino-2-fluoro-4-methyl-phenyl)-5-methyl-2H-pyrazole-1-carboxylic acid benzyl ester as a white solid.

Step 6 3-(5-Amino-2-fluoro-4-methyl-phenyl)-5-methyl-pyrazole-1-carboxylic acid benzyl ester 3-(5-tert-Butoxycarbonylamino-2-fluoro-4-methyl-phenyl)-5-methyl-2H-pyrazole-1-carboxylic acid benzyl ester (320 mg) was hydrogenated using 10% Pd/C (40 mg) following the procedure of step 2 to give 3-(5-amino-2-fluoro-4-methyl-phenyl)-5-methyl-pyrazole-1-carboxylic acid benzyl ester (205 mg) as a white solid.

Preparation 6

2-Methyl-5-(5-methyl-2H-pyrazol-3-yl)-phenylamine

The synthetic procedure used in this preparation is outlined in Scheme F.

SCHEME F

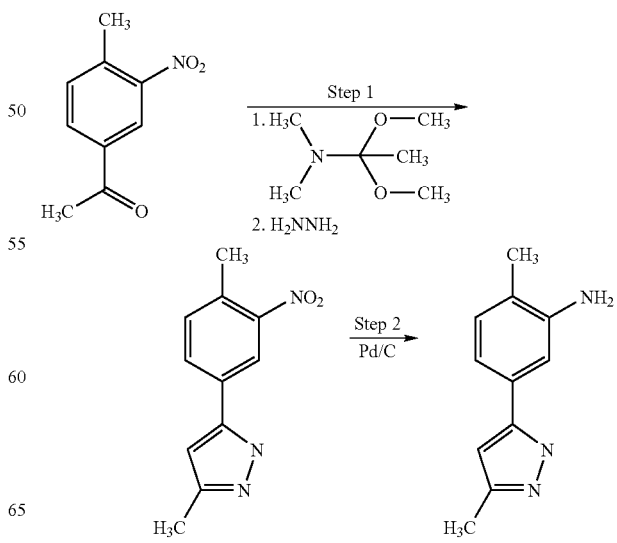

Step 1 5-Methyl-3-(4-methyl-3-nitro-phenyl)-1H-pyrazole

A solution of 1-(4-methyl-3-nitro-phenyl)-ethanone and (1,1-dimethoxy-ethyl)-dimethyl-amine in DMF was heated at 90° C. for 3 hours, then cooled to room temperature. Solvent was removed under reduced pressure, and the residue was dissolved in a mixture of EtOH (25 ml) and THF (5 ml). The mixture was cooled to 0° C., and hydrazine hydrate (5 ml) at 0° C. was added. The mixture was stirred for 16 hours at room temperature, then concentrated under reduced pressure. The residue was purified by "flash chromatography" (0 to 30% EtOAc in hexanes) to give 8.5 g of 5-methyl-3-(4-methyl-3-nitro-phenyl)-1H-pyrazole as a yellowish solid, which was recrystallized from EtOAc to give 8.2 g of yellow powder.

Step 2 2-Methyl-5-(5-methyl-2H-pyrazol-3-yl)-phenylamine

5-Methyl-3-(4-methyl-3-nitro-phenyl)-1H-pyrazole (8.2 g) was dissolved in ethanol and Palladium (10%) on activated carbon was added. The mixture was subject to barometric hydrogenation under balloon pressure for five hours at room temperature. The mixture was filtered and the filtrate was concentrated under reduced pressure to give 414 mg of crude 2-methyl-5-(5-methyl-2H-pyrazol-3-yl)-phenylamine as a white solid, which was used directly without further purification.

Preparation 7

5-{1-[2-(tert-Butyl-dimethyl-silanyloxy)-ethyl]-5-methyl-1H-pyrazol-3-yl}-2-methyl-phenylamine The synthetic procedure used in this preparation is outlined in Scheme G.

SCHEME G

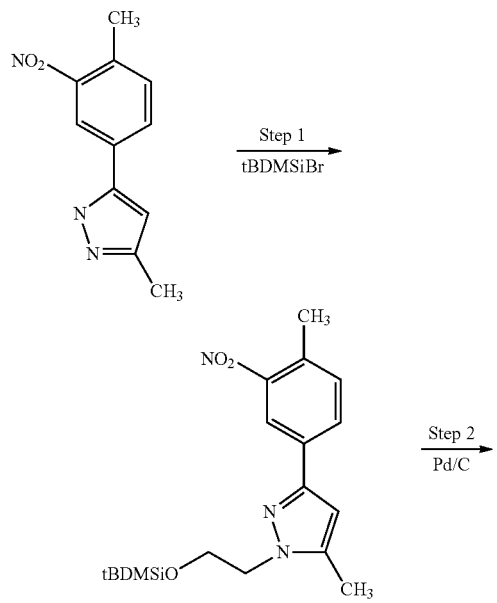

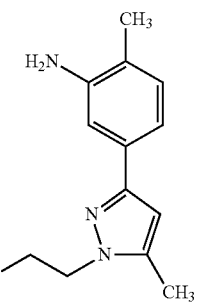

Step 1 1-[2-(tert-Butyl-dimethyl-silanyloxy)-ethyl]-5-methyl-3-(4-methyl-3-nitro-phenyl)-1H-pyrazole A solution of 5-Methyl-3-(4-methyl-3-nitro-phenyl)-1H-pyrazole, tert-butyl-dimethylsilyl bromide, $Cs_2CO_3$ and NaI in NMP was heated in a microwave oven at 100° C. for 1 hour, and then cooled to room temperature. The reaction mixture was diluted with EtOAc, washed with water and brine, dried over $Na_2SO_4$, filtered, and concentrated under reduced pressure. The residue was purified by "flash chromatography" (0 to 30% EtOAc in hexanes to give 867 mg of 1-[2-(tert-butyl-dimethyl-silanyloxy)-ethyl]-5-methyl-3-(4-methyl-3-nitro-phenyl)-1H-pyrazole as an oil that also contained 1-[2-(tert-butyl-dimethyl-silanyloxy)-ethyl]-3-methyl-5-(4-methyl-3-nitro-phenyl)-1H-pyrazole as a minor product.

Step 2 5-{1-[2-(tert-Butyl-dimethyl-silanyloxy)-ethyl]-5-methyl-1H-pyrazol-3-yl}-2-methyl-phenylamine 1-[2-(tert-Butyl-dimethyl-silanyloxy)-ethyl]-5-methyl-3-(4-methyl-3-nitro-phenyl)-1H-pyrazole (867 mg) was dissolved in ethanol and Palladium (10%) on activated carbon was added. The mixture was subject to barometric hydrogenation under balloon pressure for five hours at room temperature. The mixture was filtered and the filtrate was concentrated under reduced pressure to give crude 5-{1-[2-(tert-Butyl-dimethyl-silanyloxy)-ethyl]-5-methyl-1H-pyrazol-3-yl}-2-methyl-phenylamine as a white solid, which was used directly without further purification.

Preparation 8

2-Methyl-5-(4-methyl-pyrazol-1-yl)-phenylamine

The synthetic procedure used in this preparation is outlined in Scheme H.

SCHEME H

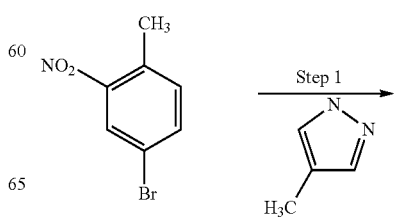

Step 1 4-Methyl-1-(4-Methyl-3-nitro-phenyl)-1H-pyrazole

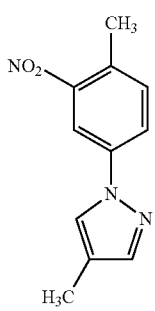 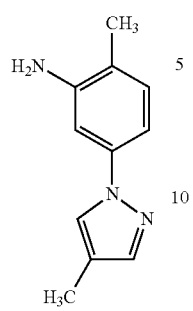

A dried flask under nitrogen was charged with 4-bromo-1-methyl-2-nitro-benzene (40 mmol), 4-methylpyrazole (20 mmol), Cs$_2$CO$_3$ (13 g), Cu$_2$O (290 mg, 2 mmol), salicylaldoxime (1.1 g, 8 mmol) and 12 mL of acetonitrile. The mixture was heated at 80° C. for 24 h. The reaction mixture was cooled to room temperature, diluted with dichloromethane and filtered through celite. The filtrate was washed with water, dried and concentrated under reduced pressure. Column chromatography on silica gel (DCM/Hexane 30-100%) gave 4-methyl-1-(4-Methyl-3-nitro-phenyl)-1H-pyrazole as a yellow solid (60% yield).

Step 2
2-Methyl-5-(4-methyl-pyrazol-1-yl)-phenylamine

4-Methyl-1-(4-methyl-3-nitro-phenyl)-1H-pyrazole from step 1 was dissolved in EtOH and hydrogenated at room temperature using a hydrogen balloon in the presence of 5% palladium on charcoal. After 20 hours, TLC (EtOAC/Hexanes 1:2) indicated complete reaction. The reaction mixture was filtered through celite and the filtrate was evaporated under reduced pressure to give 2-methyl-5-(4-methyl-pyrazol-1-yl)-phenylamine, MS (M+H)=188.

Preparation 9

4-(3-Amino-4-methyl-phenyl)-2-methyl-2H-pyridazin-3-one

The synthetic procedure used in this preparation is outlined in Scheme I.

SCHEME I

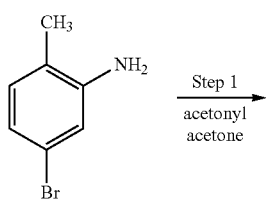

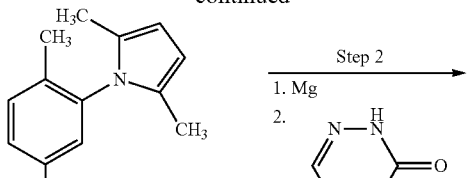

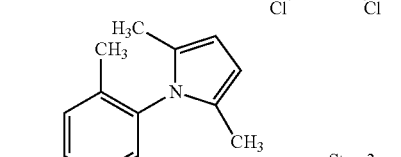

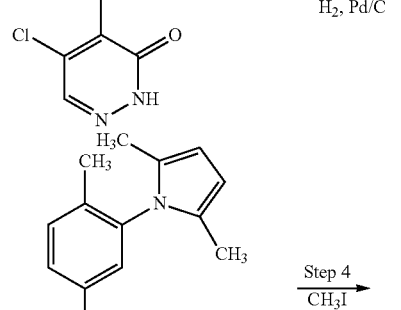

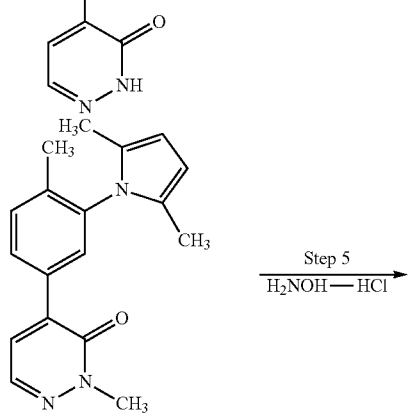

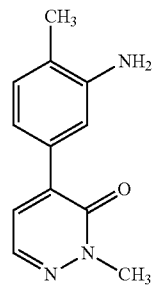

Step 1 1-(5-Bromo-2-methyl-phenyl)-2,5-dimethyl-1H-pyrrole

To a solution 5-bromo-2-methyl aniline (6.38 g, 36.74 mmol) in EtOH (30 ml) was added acetonyl acetone (5.0 ml, 42.62 mmol) and one drop of conc. aqueous HCl. The mixture was heated at reflux for 18 h and then cooled. Solvent was evaporated to dryness under reduced pressure and the residue was partitioned between water and EtOAc. The organic layer was separated and washed with water and brine dried over MgSO₄, filtered and concentrated to dryness under reduced pressure. Purification of the residue by flash chromatography (hex:EtOAc/8:2) gave 5.8 g of 1-(5-bromo-2-methyl-phenyl)-2,5-dimethyl-1H-pyrrole (60%) as a clear oil.

Step 2 5-Chloro-4-[3-(2,5-dimethyl-pyrrol-1-yl)-4-methyl-phenyl]-2H-pyridazin-3-one To a solution of 1-(5-bromo-2-methyl-phenyl)-2,5-dimethyl-1H-pyrrole (2.825 g, 10.69 mmol) in THF (13 ml) was added magnesium (0.265 g, 10.96 mmol). The mixture was heated at reflux for 1 hour, then cooled to 20° C. and added to a solution of 4,5-dichloro-2H-pyridazino-3-one (0.706 g, 4.28 mmol) in THF (10 ml) and diethyl ether (20 ml). The mixture was heated at reflux for 18 hours. The reaction mixture was cooled and saturated aqueous ammonium chloride was added, and the product was extracted with EtOAc. The combined extracts were washed with water and brine, dried over MgSO₄, filtered and concentrated to dryness under reduced pressure. Purification of the residue by flash chromatography (hex:EtOAc/6:4) gave 1.28 g (95%) of 5-chloro-4-[3-(2,5-dimethyl-pyrrol-1-yl)-4-methyl-phenyl]-2H-pyridazin-3-one as a yellow solid.

Step 3 4-[3-(2,5-Dimethyl-pyrrol-1-yl)-4-methyl-phenyl]-2H-pyridazin-3-one

To a solution of 5-chloro-4-[3-(2,5-dimethyl-pyrrol-1-yl)-4-methyl-phenyl]-2H-pyridazin-3-one (0.90 g, 2.87 mmol) and KOH (0.40 g, 7.17 mmol) in DMF (1.2 ml) and water (11 ml) was added 10% Pd/C (0.05 g). The mixture was hydrogenated in a Parr vessel at 4.14 BAR for 18 hours. Aqueous 10% KOH (15 ml) was added and the mixture was filtered. The filtrate was take to pH 1 with conc. HCl and extracted with DCM. The combined extracts were washed with water and brine, dried over MgSO₄, filtered and concentrated to dryness under reduced pressure. Purification of the residue by flash chromatography (hex:EtOAc/1:1) gave 0.429 g (54%) of 4-[3-(2,5-dimethyl-pyrrol-1-yl)-4-methyl-phenyl]-2H-pyridazin-3-one as a yellow solid.

Step 4 4-[3-(2,5-Dimethyl-pyrrol-1-yl)-4-methyl-phenyl]-2-methyl-2H-pyridazin-3-one To a solution of 4-[3-(2,5-dimethyl-pyrrol-1-yl)-4-methyl-phenyl]-2H-pyridazin-3-one (1.0 g, 3.58 mmol) in DMF (10 ml) was added potassium hexamethyldisilazane (7.88 ml of 0.5M toluene solution, 3.94 mmol) at 0° C. The mixture was stirred at 0° C. for 10 minutes, and methyl iodide (0.267 ml, 4.30 mmol) was added. The mixture was aloud to reach room temperature and was stirred for 24 hours. Water was added and the product was extracted with EtOAc. The combined organic extracts were washed with water and brine, dried over MgSO₄, filtered and concentrated to dryness under reduced pressure. Purification of the residue by flash chromatography (hex:EtOAc/6:4) gave 1.05 g (100%) of 4-[3-(2,5-dimethyl-pyrrol-1-yl)-4-methyl-phenyl]-2-methyl-2H-pyridazin-3-one as a yellow solid.

Step 5 4-(3-Amino-4-methyl-phenyl)-2-methyl-2H-pyridazin-3-one

To a solution of 4-[3-(2,5-dimethyl-pyrrol-1-yl)-4-methyl-phenyl]-2-methyl-2H-pyridazin-3-one (1.05 g, 3.57 mmol) in EtOH (20 ml) and water (10 ml) was added hydroxyl amine hydrochloride (2.49 g, 35.79 mmol) and triethyl amine (1.0 ml, 7.16 mmol). The mixture was heated at reflux for 24 hours. The solvent was evaporated to dryness under reduced pressure and the rsidue was partitioned between water and EtOAc. The organic layer was separated and washed with water and brine, dried over MgSO₄, filtered and concentrated to dryness under reduced pressure. Purification of the residue by flash chromatography (hex:EtOAc/1:1) gave 0.396 g (51%) of 4-(3-amino-4-methyl-phenyl)-2-methyl-2H-pyridazin-3-one as a yellow solid.

Preparation 10

2,6-Dimethyl-quinolin-5-ylamine

The synthetic procedure used in this preparation is outlined in Scheme J.

SCHEME J

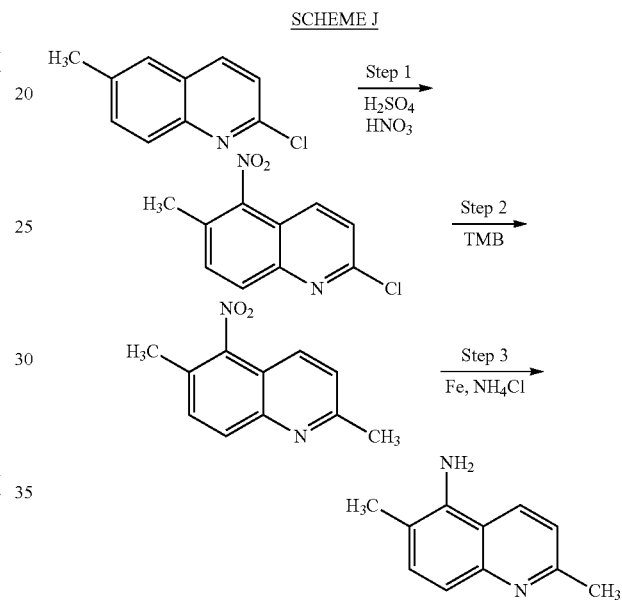

Step 1 2-Chloro-6-methyl-5-nitro-quinoline

Sulfuric acid(7.2 mL) was added to 2-chloro-6-methyl-quinoline (1.15 g, 6.5 mmol). To the resulting solution was added nitric acid(3.1 mL), and the mixture was heated at 100° C. for 20 minutes. After cooling, the mixture was poured into ice-water. The resulting yellow solid was collected by filtration and dried under vacuum to give 2-chloro-6-methyl-5-nitro-quinoline (1.42 g, 98%).

Step 2 2,6-Dimethyl-5-nitro-quinoline

To a solution of 2-chloro-6-methyl-5-nitro-quinoline (350 mg, 1.57 mmol) in dioxane (6.7 mL) and water (0.7 mL) were added K₂CO₃ (652 mg, 4.72 mmol), trimethylboroxine (0.22 mL, 1.57 mmol) and PdCl₂(dppf) (129 mg, 0.157 mmol) under Ar. The mixture was heated at 105° C. overnight, then cooled and the resulting solid was collected by filtration, washed with ethyl acetate, and dried. Purification by flash column (hexane/ethyl acetate gradient) gave 2,6-dimethyl-5-nitro-quinoline (195 mg, 61%).

Step 3 2,6-Dimethyl-quinolin-5-ylamine

To a solution of 2,6-dimethyl-5-nitro-quinoline (192 mg, 0.95 mmol) in ethanol (9.3 mL) and water (4.7 mL) were added iron powder (280 mg, 5.0 mmol) and NH₄Cl 280 mg, 5.2 mmol). The mixture was heated at reflux for 2 h, then cooled filtered. The filtrate was concentrated under reduced pressure, and the aqueous residue was extracted with ethyl acetate. The combined extracts were washed with water and brine, dried over Na₂SO₄, filtered and concentrated to dryness under reduced pressure. Purification of the residue by flash column (hexane/ethyl acetate gradient) gave 2,6-dimethyl-quinolin-5-ylamine (120 mg, 73%).

Example 1

(S)-4-(4-Fluoro-phenyl)-1-methyl-2-oxo-1,2,3,4-tetrahydro-pyrimidine-5-carboxylic acid[4-chloro-5-(2-hydroxy-ethoxy)-2-methyl-phenyl]-amide The synthetic procedure used in this preparation is outlined in Scheme K.

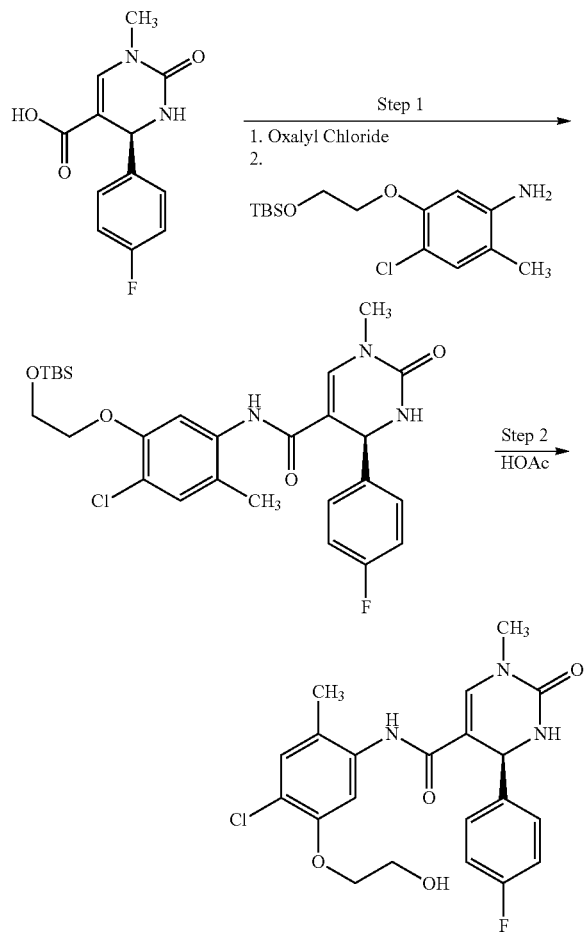

Step 1 (S)-4-(4-Fluoro-phenyl)-1-methyl-2-oxo-1,2,3,4-tetrahydro-pyrimidine-5-carboxylic acid{5-[2-(tert-butyl-dimethyl-silanyloxy)-ethoxy]-4-chloro-2-methyl-phenyl}-amide To a solution of 10 mL dichloromethane and 1 drop of DMF was added 150 mg of (S)-4-(4-fluoro-phenyl)-1-methyl-2-oxo-1,2,3,4-tetrahydro-pyrimidine-5-carboxylic acid. To this mixture was added 70 µl oxalyl chloride. When the bubbling stopped another drop of oxalyl chloride was added but as no bubbling was observed the solution was stirred at room temperature for 30 minutes after which the solvent was removed in vacuo to afford crude (S)-4-(4-fluoro-phenyl)-1-methyl-2-oxo-1,2,3,4-tetrahydro-pyrimidine-5-carboxylic acid chloride (not shown in Scheme H). This acid chloride was taken up in propionitrile and added to a solution of 125 mg 5-[2-(tert-butyl-dimethyl-silanyloxy)-ethoxy]-4-chloro-2-methyl-phenylamine, 3 ml propionitrile, and 0.1 ml di-isopropylethylamine. The solution was stirred at room temperature for 18 hours, then diluted with ethyl acetate and aqueous pH 2 buffer. The layers were separated and the organic layer dried over Na₂SO₄, filtered and the solvent removed in vacuo to give (S)-4-(4-fluoro-phenyl)-1-methyl-2-oxo-1,2,3,4-tetrahydro-pyrimidine-5-carboxylic acid{5-[2-(tert-butyl-dimethyl-silanyloxy)-ethoxy]-4-chloro-2-methyl-phenyl}-amide, which was used directly in the next step without further purification.

Step 2 (S)-4-(4-Fluoro-phenyl)-1-methyl-2-oxo-1,2,3,4-tetrahydro-pyrimidine-5-carboxylic acid[4-chloro-5-(2-hydroxy-ethoxy)-2-methyl-phenyl]-amide The (S)-4-(4-Fluoro-phenyl)-1-methyl-2-oxo-1,2,3,4-tetrahydro-pyrimidine-5-carboxylic acid{5-[2-(tert-butyl-dimethyl-silanyloxy)-ethoxy]-4-chloro-2-methyl-phenyl}-amide from step 1 was dissolved in a mixture of 1 ml THF, 1 mL water, and 3 ml HOAc. This solution was stirred at room temperature for 18 hours, then diluted with water and extracted with ethyl acetate. The combined ethyl acetate layers were dried over Na₂SO₄, filtered and the solvent removed in vacuo. The residue was chromatographed in 3% MeOH/CH₂Cl₂ to give 50 mg of (S)-4-(4-Fluoro-phenyl)-1-methyl-2-oxo-1,2,3,4-tetrahydro-pyrimidine-5-carboxylic acid[4-chloro-5-(2-hydroxy-ethoxy)-2-methyl-phenyl]-amide, MS (M+H)=434.

Additional compounds using the above procedure, using the appropriate aniline compound in place of 5-[2-(tert-butyl-dimethyl-silanyloxy)-ethoxy]-4-chloro-2-methyl-phenylamine, are shown in Table 1.

Example 2

(S)-4-(4-Fluoro-phenyl)-1-methyl-2-oxo-1,2,3,4-tetrahydro-pyrimidine-5-carboxylic acid[2-methyl-5-(4-methyl-pyrazol-1-yl)-phenyl]-amide The synthetic procedure used in this preparation is outlined in Scheme L.

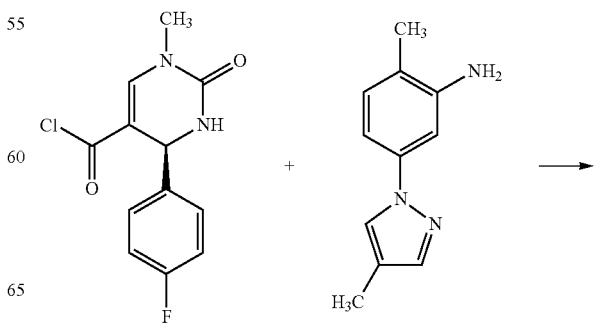

-continued

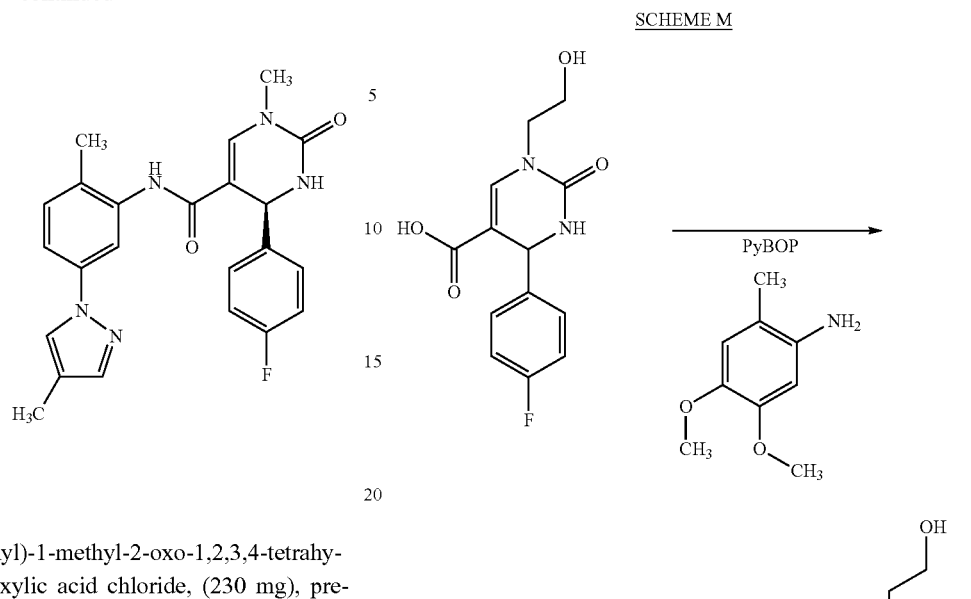

(S)-4-(4-Fluoro-phenyl)-1-methyl-2-oxo-1,2,3,4-tetrahydro-pyrimidine-5-carboxylic acid chloride, (230 mg), prepared as in Example 1, was added to a solution of 163 mg of 2-methyl-5-(4-methyl-pyrazol-1-yl)-phenylamine, 10 mL propionitrile, and 0.1 mL pyridine. The resulting solution was heated at 100° for 30 minutes, then cooled to 50° and diluted with 5 mL water and 10 mL toluene. The mixture was vigorously stirred at 50° and the layers were separated. The warm toluene layer was washed with saturated sodium bicarbonate, and then concentrated under reduced pressure to a brown residue, which was triturated with 2 mL toluene and filtered. The resulting solid was recrystallized from ethanol/water to yield 175 mg of (S)-4-(4-fluoro-phenyl)-1-methyl-2-oxo-1,2,3,4-tetrahydro-pyrimidine-5-carboxylic acid[2-methyl-5-(4-methyl-pyrazol-1-yl)-phenyl]-amide, MS (M+H)=420.

Similarly prepared, but replacing 2-methyl-5-(4-methyl-pyrazol-1-yl)-phenylamine with 4,5-dimethoxy-2-methyl-phenylamine, was 4-(4-fluoro-phenyl)-1,3-dimethyl-2-oxo-1,2,3,4-tetrahydro-pyrimidine-5-carb oxylic acid(4,5-dimethoxy-2-methyl-phenyl)-amide, MS (M+H)=414.

Similarly prepared, but replacing 2-methyl-5-(4-methyl-pyrazol-1-yl)-phenylamine with 4-(3-amino-4-methyl-phenyl)-2-methyl-2H-pyridazin-3-one, was (S)-4-(4-Fluoro-phenyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide, MS (M+H)=448.

Additional compounds using the above procedure, using the appropriate aniline compound in place of 2-methyl-5-(4-methyl-pyrazol-1-yl)-phenylamine, are shown in Table 1.

Example 3

4-(4-Fluoro-phenyl)-1-(2-hydroxy-ethyl)-2-oxo-1,2,3,4-tetrahydro-pyrimidine-5-carboxylic acid (4,5-dimethoxy-2-methyl-phenyl)-amide The synthetic procedure used in this preparation is outlined in Scheme M.

SCHEME M

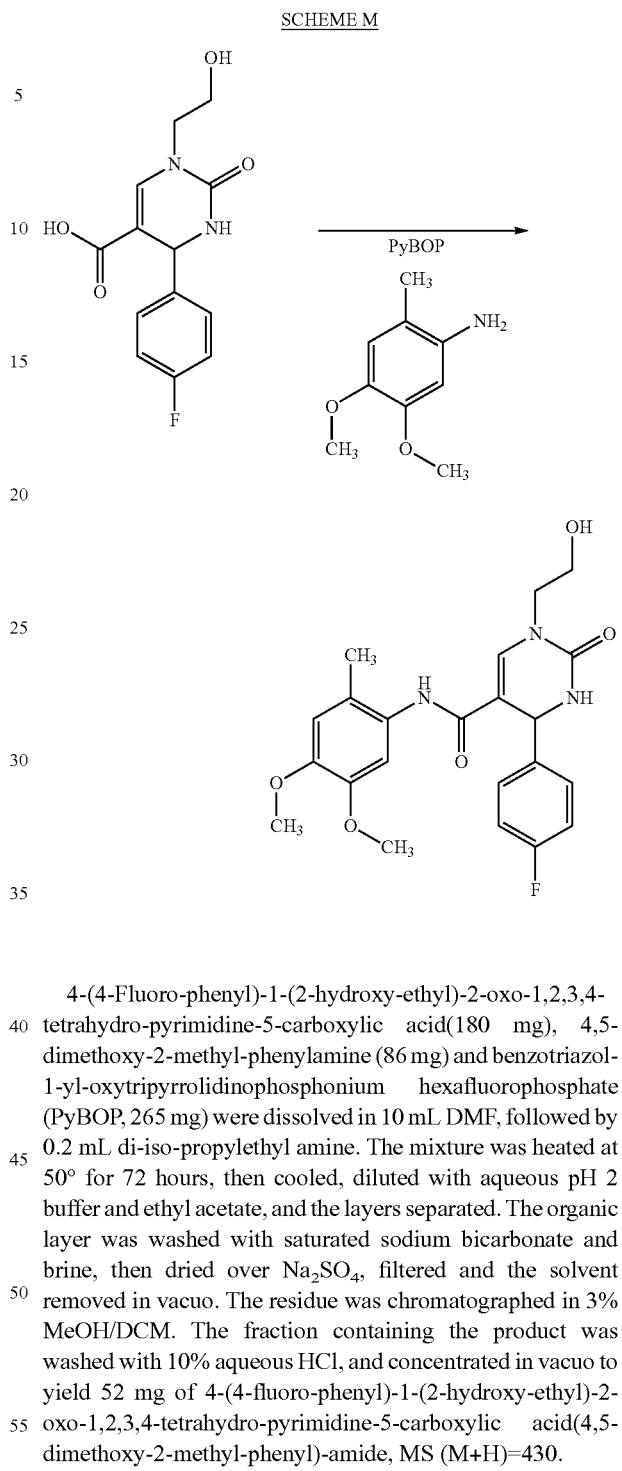

4-(4-Fluoro-phenyl)-1-(2-hydroxy-ethyl)-2-oxo-1,2,3,4-tetrahydro-pyrimidine-5-carboxylic acid(180 mg), 4,5-dimethoxy-2-methyl-phenylamine (86 mg) and benzotriazol-1-yl-oxytripyrrolidinophosphonium hexafluorophosphate (PyBOP, 265 mg) were dissolved in 10 mL DMF, followed by 0.2 mL di-iso-propylethyl amine. The mixture was heated at 50° for 72 hours, then cooled, diluted with aqueous pH 2 buffer and ethyl acetate, and the layers separated. The organic layer was washed with saturated sodium bicarbonate and brine, then dried over $Na_2SO_4$, filtered and the solvent removed in vacuo. The residue was chromatographed in 3% MeOH/DCM. The fraction containing the product was washed with 10% aqueous HCl, and concentrated in vacuo to yield 52 mg of 4-(4-fluoro-phenyl)-1-(2-hydroxy-ethyl)-2-oxo-1,2,3,4-tetrahydro-pyrimidine-5-carboxylic acid(4,5-dimethoxy-2-methyl-phenyl)-amide, MS (M+H)=430.

Example 4

4-(4-Fluoro-phenyl)-3-methyl-2-oxo-1,2,3,4-tetrahydro-pyrimidine-5-carboxylic acid(4,5-dimethoxy-2-methyl-phenyl)-amide The synthetic procedure used in this preparation is outlined in Scheme N.

SCHEME N

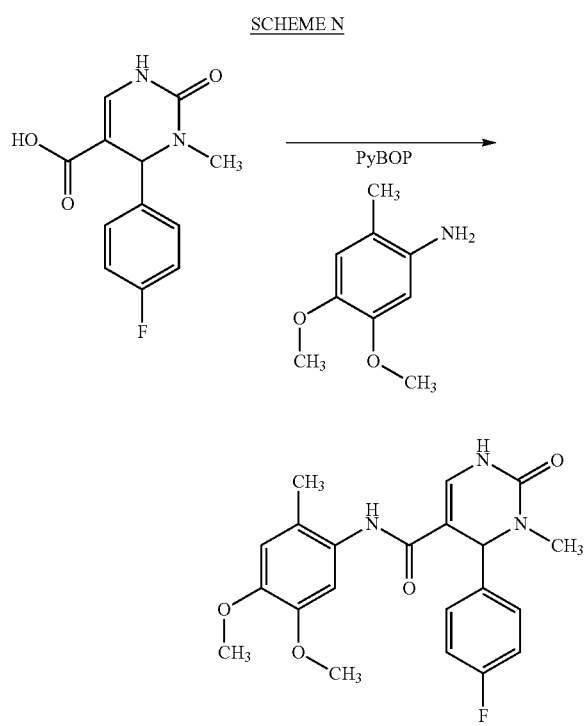

4-(4-Fluoro-phenyl)-3-methyl-2-oxo-1,2,3,4-tetrahydro-pyrimidine-5-carboxylic acid(4,5-dimethoxy-2-methyl-phenyl)-amide was prepared from 4-(4-Fluoro-phenyl)-3-methyl-2-oxo-1,2,3,4-tetrahydro-pyrimidine-5-carboxylic acid and 4,5-dimethoxy-2-methyl-phenylamine using the procedure of Example 3, MS (M+H)=400.

Example 5

(S)-4-(4-Fluoro-phenyl)-1-methyl-2-oxo-1,2,3,4-tetrahydro-pyrimidine-5-carboxylic acid(2,6-dimethyl-quinolin-5-yl)-amide The synthetic procedure used in this preparation is outlined in Scheme O.

SCHEME O

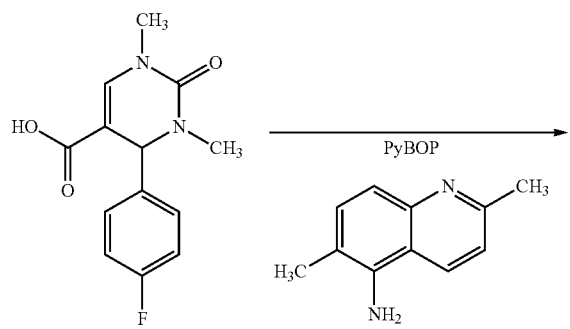

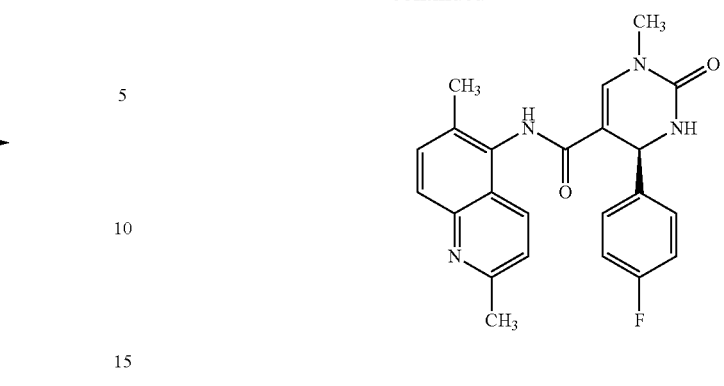

(S)-4-(4-Fluoro-phenyl)-1-methyl-2-oxo-1,2,3,4-tetrahydro-pyrimidine-5-carboxylic acid(2,6-dimethyl-quinolin-5-yl)-amide was prepared from 4-(4-fluoro-phenyl)-3-methyl-2-oxo-1,2,3,4-tetrahydro-pyrimidine-5-carboxylic acid and 2,6-dimethyl-quinolin-5-ylamine using the procedure of Example 3, MS (M+H)=405.

Example 6

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 7

Intracellular Calcium Flux (FLIPR) Assay

Compound and Reagent Preparation

Stock solutions of compounds were prepared from powders as a 10 mM DMSO stock solution. These solutions were stored at RT during the two week period of these experiments to prevent freeze-thaw of the DMSO stocks. The DMSO stocks were added to the appropriate assay buffer at a concentration of 10 µM, and then diluted serially to the final concentrations that were tested. No observable precipitate was formed at any time during this process. The aqueous solutions of compounds as well as ATP (Sigma A7699) and BzATP (Sigma B6396) were prepared fresh for each day of experiment.

Cell Culture: 1321N1-hP2X$_7$ and HEK293-rP2X$_7$

1321N1 cells stably expressing the full length human P2X$_7$ gene (1321N1-hP2X$_7$) and HEK293 cells stably expressing the full length rat P2X$_7$ gene (HEK293-rP2X$_7$) were obtained from the Roche Cell Culture Facility. 1321N1-hP2X$_7$ cells were grown in Dulbecco's Modified Eagle's Medium (DMEM) high glucose supplemented with 10% FBS and 250 µg/mL G418. HEK293-rP2X$_7$ cells were grown in DMEM/F-12 supplemented with 10% FBS, 1 mM CaCl$_2$, 2 mM MgCl$_2$, 2 mM L-Glutamine and 500 µg/ml G418. Cells were split such that they never became >70% confluent.

Intracellular Calcium Flux (FLIPR)

On the day prior to the experiment, 1321N1-hP2X$_7$ or HEK293-rP2X$_7$ cells were released into suspension with calcium-free PBS+Versene and washed by centrifugation with calcium-free PBS to remove the Versene. Cells were resuspended in growth medium at a density of 2.5×10$^5$ cells/mL and seeded into black walled, clear bottom 96 well plates (50,000 cells/well) approximately 18 hr prior to intracellular calcium flux experiments.

On the day of the experiment, plates were washed with FLIPR buffer (calcium- and magnesium-free Hank's Balanced Salt Solution (HBSS) supplemented with 10 mM Hepes, 2.5 mM probenecid and 2 mM calcium chloride) using a BIO-TEK 96 channel plate washer and incubated with 2 mM fluo-3 dye at 37° C. for one hr. The dye was then removed by plate washing and the cells were allowed to equilibrate for 20 min at room temperature with antagonist or vehicle (FLIPR buffer). Agonist (100 µM BzATP final concentration for hP2X$_7$; 5µM BzATP final concentration or rP2X$_7$) was added online with the FLIPR and fluorescence measurements made at 1 sec intervals for 60 sec followed by 3 sec intervals for a further 4 min (5 min total). A final addition of 5 μM ionomycin was made and the maximal BzATP-evoked fluorescence normalized to the maximal ionomycin-evoked fluorescence.

Example 8

Human Whole Blood IL-1β Release Assay

Compound & Reagent Preparation 10 mM stock solutions of compounds in DMSO (Sigma D2650) were prepared and used either fresh or after storage at −20° C. Appropriate (200×) serial dilutions of the compounds were made in DMSO, then freshly diluted 1 to 20 (10×) with Dulbecco's phosphate buffered saline (DPBS; Mediatech Inc., 21-030), such that final DMSO concentration in the blood always equaled 0.5%.

30 mM ATP (Sigma A7699) was prepared immediately before use in 50 mM HEPES (Gibco 15630) and the pH adjusted to 7.2 with 1M sodium hydroxide.

Blood Donors

Human blood donors were medication free and restricted from utilizing alcohol or caffeine for at least the 24 hr preceding collection. The blood was collected into sodium heparin vacutainer tubes and used the same day.

Assay Method

The OptEIA Human IL-1β ELISA Set, OptEIA Coating Buffer, Assay Diluent and TMB Substrate Reagent Set used in the assay were commercially obtained from BD Pharmingen. Blood was diluted 1:1 with Dulbecco's PBS, LPS (Escherichia Coli 0127:B8, Sigma L3129) added to a final concentration of 25 ng/mL and incubated for 2 hr at 37° C. 48 of this LPS primed blood was added to 6 μL of the 10× compound in 5% DMSO/PBS in the appropriate well of a 96-well polypropylene plate. The blood and compound were mixed and allowed to incubate for 30 min at 37° C. 6 ml of 30 mM ATP was added to the LPS-primed blood+compound, mixed thoroughly and incubated for a further 30 min at 37° C. 96 μL of ELISA assay buffer was added to each well and the plate centrifuged at 4° C. 1,200 rpm for 10 min. Supernatant was removed and assayed for IL-1β using the OptEIA kit according to the manufacturer's protocol (Serum may be frozen at −20° C. prior to assay). IC$_{50}$s were calculated using XLfit.

Example 9

In vivo Assay for Asthma and Lung Function

BALb/cJ mice are immunized with a standard immunization protocol. Briefly, mice (N=8/group) are immunized i.p. with ovalbumin (OVA; 10 μg) in alum on days 0 and 14. Mice are then challenged with aerosolized OVA (5%) on day 21 and 22 Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula IIIa or IIIb:

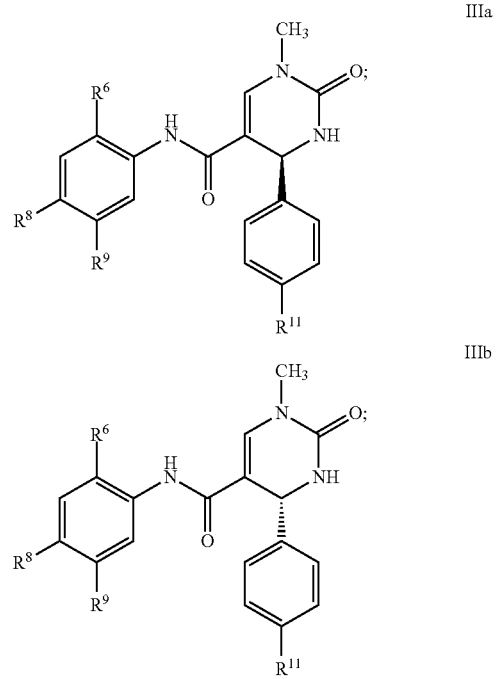

or a pharmaceutically acceptable salt thereof,
wherein:
$R^6$ is: bromo or methyl;
$R^8$ is: hydrogen; methoxy; or halo;
$R^9$ is: methoxy; 2-hydroxy-ethoxy; 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl); 2-methyl-5-(5-methyl- 2-oxo-2H-pyridin-1-yl; 2-methyl-3-oxo-2,3-dihydro-pyridazin-4-yl; or 1-methyl-6-oxo-1,6-dihydro-pyridin-3-yl;
$R^{11}$ is halo.

2. The compound of claim 1, wherein said compound is of formula IIIa.

3. The compound of claim 1, wherein said compound is of formula IIIb.

4. The compound of claim 1, wherein $R^6$ is methyl.

5. The compound of claim 1, wherein $R^8$ is: hydrogen; methoxy; or chloro.

6. The compound of claim 1, wherein $R^8$ is hydrogen.

7. The compound of claim 1, wherein $R^{11}$ is fluoro.

8. The compound of claim 1, wherein $R^9$ is: 5-methyl-1H-pyrazol-3-yl; 4-methyl-pyrazol-1-yl; 4,5-dimethyl-4H-[1,2,4]triazol-3-yl; 2-methyl-3-oxo-2,3-dihydro-pyridazin-4-yl; 2H-pyrazol-3-yl; 1-((R)-2-hydroxy-3-methoxy-propyl)-5-methyl-1H-pyrazol-3-yl; 4-((R)-2-hydroxy-3-methoxy-propyl)-3,5-dioxo-4,5-dihydro-3H-[1,2,4]triazin-2-yl; 6-oxo-6H-pyridazin-1-yl; 3-methyl-6-oxo-6H-pyridazin-1-yl; 6-oxo-1,6-dihydro-pyrazin-2-yl; 2-methyl-3-oxo-2,3-dihydro-pyridazin-4-yl); 4-methyl-3,5-dioxo-4,5-dihydro-3H-[1,2,4]triazin-2-yl; 1-((S)-2-hydroxy-3-methoxy-propyl)-5-methyl-1H-pyrazol-3-yl; 2-ethyl-3-oxo-2,3-dihydro-pyridazin-4-yl); 1-methyl-6-oxo-1,6-dihydro-pyridazin-3-yl; 6-oxo-1,6-dihydro-pyridazin-3-yl; 2-((R)-2-hydroxy-3-methoxy-propyl)-3-oxo-2,3-dihydro-pyridazin-4-yl; 2-oxo-pyrrolidin-1-yl; 2,4-dioxo-3,4-dihydro-2H-pyrimidin-1-y; 3-methyl-2-oxo-2H-pyridin-1-yl; 2-oxo-2H-pyridin-1-yl; 6-methoxy-pyridazin-3-yl; 2,6-dioxo-3,6-dihydro-2H-pyrimidin-1-yl; (2-hydroxy-ethyl)-6-oxo-1,6-dihydro-pyridazin-3-yl; 1-methyl-2-oxo-1,2-dihydro-pyridin-3-yl; (2-hydroxy-3-methoxy-propyl)-6-oxo-1,6-dihydro-pyridazin-3-yl; 6-oxo-6H-pyridazin-1-yl; 4-ethyl-3,5-dioxo-4,5-dihydro-3H-[1,2,4]triazin-2-yl; 3-methyl-2-oxo-2H-pyridin-1-yl; 4-methyl-6-oxo-6H-pyridazin-1-yl; 2-methyl-5-(3-methyl-2,4-dioxo-3,4-dihydro-2H-pyrimidin-1-yl; 2-methyl-5-(5-methyl-2-oxo-2H-pyridin-1-yl; 2-methyl-3-oxo-2,3-dihydro-pyridazin-4-yl; or 1-methyl-6-oxo-1,6-dihydro-pyridin-3-yl.

9. The compound of claim 1, wherein $R^9$ is 2-ethyl-3-oxo-2,3-dihydro-pyridazin-4-yl.

10. The compound of claim 1, wherein $R^9$ is 5-methyl-1H-pyrazol-3-yl.

11. The compound of claim 1, wherein $R^9$ is 2-methyl-3-oxo-2,3-dihydro-pyridazin-4-yl.

12. The compound of claim 1, wherein $R^9$ is 6-methoxy-pyridazin-3-yl.

13. The compound of claim 1, wherein $R^9$ is 1-methyl-2-oxo-1,2-dihydro-pyridin-3-yl.

14. The compound of claim 1, wherein $R^9$ is 6-oxo-6H-pyridazin-1-yl.

15. The compound of claim 1, wherein $R^9$ is 3-methyl-2-oxo-2H-pyridin-1-yl.

16. The compound of claim 1, wherein $R^9$ is 4-ethyl-3,5-dioxo-4,5-dihydro-3H-[1,2,4]triazin-2-yl.

17. The compound of claim 1, wherein $R^9$ is 1-(2-hydroxy-ethyl)-6-oxo-1,6-dihydro-pyridazin-3-yl.

18. A compound selected from:
4-(4-Fluoro-phenyl)-2-oxo-1,2,3,4-tetrahydro-pyrimidine-5-carboxylic acid(4,5-dimethoxy-2-methyl-phenyl)-amide;
4-(4-Fluoro-phenyl)-1-methyl-2-oxo-1,2,3,4-tetrahydro-pyrimidine-5-carboxylic acid(4,5-dimethoxy-2-methyl-phenyl)-amide;
(R)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide;
(S)-4-(4-Fluoro-phenyl)-2-oxo-1,2,3,4-tetrahydro-pyrimidine-5-carboxylic acid (4,5-dimethoxy-2-methyl-phenyl)-amide;
(S)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide;
(S)-4-(4-Fluoro-phenyl)-1-methyl-2-oxo-1,2,3,4-tetrahydro-pyrimidine-5-carboxylic acid(4,5-dimethoxy-2-methyl-phenyl)-amide;
(S)-4-(4-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;
(S)-4-(4-Fluoro-phenyl)-1-methyl-2-oxo-1,2,3,4-tetrahydro-pyrimidine-5-carboxylic acid[4-chloro-5-(2-hydroxy-ethoxy)-2-methyl-phenyl]-amide;
4-(4-Fluoro-phenyl)-1,3-dimethyl-2-oxo-1,2,3,4-tetrahydro-pyrimidine-5-carboxylic acid(4,5-dimethoxy-2-methyl-phenyl)-amide;
(R)-4-(4-Fluoro-phenyl)-2-oxo-1,2,3,4-tetrahydro-pyrimidine-5-carboxylic acid (4,5-dimethoxy-2-methyl-phenyl)-amide;
(S)-4-(4-Fluoro-phenyl)-1-methyl-2-oxo-1,2,3,4-tetrahydro-pyrimidine-5-carboxylic acid(6-methyl-quinolin-5-yl)-amide;
4-(4-Fluoro-phenyl)-1-(2-hydroxy-ethyl)-2-oxo-1,2,3,4-tetrahydro-pyrimidine-5-carboxylic acid(4,5-dimethoxy-2-methyl-phenyl)-amide;
4-(4-Fluoro-phenyl)-3-methyl-2-oxo-1,2,3,4-tetrahydro-pyrimidine-5-carboxylic acid(4,5-dimethoxy-2-methyl-phenyl)-amide;
4-(3-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;
(S)-4-(4-Fluoro-phenyl)-1-methyl-2-oxo-1,2,3,4-tetrahydro-pyrimidine-5-carboxylic acid[2-methyl-5-(4-methyl-pyrazol-1-yl)-phenyl]-amide;
(S)-4-(4-Fluoro-phenyl)-1-methyl-2-;
oxo-1,2,3,4-tetrahydro-pyrimidine-5-carboxylic acid[4-fluoro-5-(2-hydroxy-ethoxy)-2-methyl-phenyl]-amide;
(S)-1-Ethyl-4-(4-fluoro-phenyl)-2-oxo-1,2,3,4-tetrahydro-pyrimidine-5-carboxylic acid[4-chloro-5-(2-hydroxy-ethoxy)-2-methyl-phenyl]-amide;
(S)-4-(4-Fluoro-phenyl)-1-methyl-2-oxo-1,2,3,4-tetrahydro-pyrimidine-5-carboxylic acid[5-(4,5-dimethyl-4H-[1,2,4]triazol-3-yl)-2-methyl-phenyl]-amide;
(S)-4-(4-Fluoro-phenyl)-1-methyl-2-oxo-1,2,3,4-tetrahydropyrimidine-5-carboxylic acid{5-[1-((R)-2,3-dihydroxy-propyl)-5-methyl-1H-pyrazol-3-yl]-2-methyl-phenyl}-amide;
(S)-4-Cyclohexyl-1-methyl-2-oxo-1,2,3,4-tetrahydro-pyrimidine-5-carboxylic acid[4-chloro-5-(2-hydroxy-ethoxy)-2-methyl-phenyl]-amide;
(S)-4-(4-Fluoro-phenyl)-1-methyl-2-oxo-1,2,3,4-tetrahydro-pyrimidine-5-carboxylic acid(2,6-dimethyl-quinolin-5-yl)-amide;
(S)-4-(4-Fluoro-phenyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;
(S)-4-(4-Fluoro-phenyl)-1-methyl-2-oxo-1,2,3,4-tetrahydro-pyrimidine-5-carboxylic acid[2-methyl-3-(2H-pyrazol-3-yl)-phenyl]-amide;

(S)-4-(4-Fluoro-phenyl)-1-methyl-2-oxo-1,2,3,4-tetrahydro-pyrimidine-5-carboxylic acid{5-[1-((R)-2-hydroxy-3-methoxy-propyl)-5-methyl-1H-pyrazol-3-yl]-2-methyl-phenyl}-amide;
(S)-4-(4-Fluoro-phenyl)-1-methyl-2-oxo-1,2,3,4-tetrahydro-pyrimidine-5-carboxylic acid{5-[4-((R)-2-hydroxy-3-methoxy-propyl)-3,5-dioxo-4,5-dihydro-3H-[1,2,4]triazin-2-yl]-2-methyl-phenyl}-amide;
S)-4-(4-Fluoro-phenyl)-1-methyl-2-oxo-1,2,3,4-tetrahydro-pyrimidine-5-carboxylic acid[2-methyl-5-(6-oxo-6H-pyridazin-1-yl)-phenyl]-amide;
(S)-4-(4-Fluoro-phenyl)-1-methyl-2-oxo-1,2,3,4-tetrahydro-pyrimidine-5-carboxylic acid[2-methyl-5-(3-methyl-6-oxo-6H-pyridazin-1-yl)-phenyl]-amide;
(S)-4-(4-Fluoro-phenyl)-1-methyl-2-oxo-1,2,3,4-tetrahydro-pyrimidine-5-carboxylic acid[2-methyl-5-(6-oxo-1,6-dihydro-pyrazin-2-yl)-phenyl]-amide;
(R)-4-Cyclohexyl-1-methyl-2-oxo-1,2,3,4-tetrahydro-pyrimidine-5-carboxylic acid[4-chloro-5-(2-hydroxy-ethoxy)-2-methyl-phenyl]-amide;
(S)-4-(3-Fluoro-phenyl)-1-methyl-2-oxo-1,2,3,4-tetrahydro-pyrimidine-5-carboxylic acid[4-chloro-5-(2-hydroxy-ethoxy)-2-methyl-phenyl]-amide;
(S)-4-(4-Fluoro-phenyl)-1-methyl-2-oxo-1,2,3,4-tetrahydro-pyrimidine-5-carboxylic acid(6-methyl-2-oxo-1,2-dihydro-quinolin-5-yl)-amide;
(S)-4-(4-Fluoro-phenyl)-1-methyl-2-oxo-1,2,3,4-tetrahydro-pyrimidine-5-carboxylic acid[2-methyl-5-(3-oxo-2,3-dihydro-pyridazin-4-yl)-phenyl]-amide;
(S)-4-(3-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;
(S)-4-(4-Fluoro-phenyl)-1-methyl-2-oxo-1,2,3,4-tetrahydro-pyrimidine-5-carboxylic acid(5-ethyl-2-methyl-quinolin-6-yl)-amide;
(S)-4-(4-Fluoro-phenyl)-1-methyl-2-oxo-1,2,3,4-tetrahydro-pyrimidine-5-carboxylic acid[2-methyl-5-(4-methyl-3,5-dioxo-4,5-dihydro-3H-[1,2,4]triazin-2-yl)-phenyl]-amide;
(S)-4-(4-Fluoro-phenyl)-1-methyl-2-oxo-1,2,3,4-tetrahydro-pyrimidine-5-carboxylic acid{5-[1-((S)-2-hydroxy-3-methoxy-propyl)-5-methyl-1H-pyrazol-3-yl]-2-methyl-phenyl}-amide;
(S)-4-(3-Fluoro-phenyl)-1-methyl-2-oxo-1,2,3,4-tetrahydro-pyrimidine-5-carboxylic acid[2-methyl-5-(4-methyl-3,5-dioxo-4,5-dihydro-3H-[1,2,4]triazin-2-yl)-phenyl]-amide;
(S)-4-(4-Fluoro-phenyl)-1-methyl-2-oxo-1,2,3,4-tetrahydro-pyrimidine-5-carboxylic acid[5-(2-ethyl-3-oxo-2,3-dihydro-pyridazin-4-yl)-2-methyl-phenyl]-amide;
(S)-4-(4-Fluoro-phenyl)-1-(2-methoxy-ethyl)-2-oxo-1,2,3,4-tetrahydro-pyrimidine-5-carboxylic acid[4-chloro-5-(2-hydroxy-ethoxy)-2-methyl-phenyl]-amide;
(S)-4-(4-Fluoro-phenyl)-1-methyl-2-oxo-1,2,3,4-tetrahydro-pyrimidine-5-carboxylic acid[2-methyl-5-(1-methyl-6-oxo-1,6-dihydro-pyridazin-3-yl)-phenyl]-amide;
(S)-4-(4-Fluoro-phenyl)-1-methyl-2-oxo-1,2,3,4-tetrahydro-pyrimidine-5-carboxylic acid[2-methyl-5-(6-oxo-1,6-dihydro-pyridazin-3-yl)-phenyl]-amide;
(S)-4-(4-Fluoro-phenyl)-1-methyl-2-oxo-1,2,3,4-tetrahydro-pyrimidine-5-carboxylic acid[1-(2-hydroxy-ethyl)-5-methyl-1H-indazol-6-yl]-amide;
(S)-4-(4-Fluoro-phenyl)-1-methyl-2-oxo-1,2,3,4-tetrahydro-pyrimidine-5-carboxylic acid{5-[2-((R)-2-hydroxy-3-methoxy-propyl)-3-oxo-2,3-dihydro-pyridazin-4-yl]-2-methyl-phenyl}-amide;
(S)-4-(3-Fluoro-phenyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;
(S)-4-(4-Fluoro-phenyl)-1-methyl-2-oxo-1,2,3,4-tetrahydro-pyrimidine-5-carboxylic acid[2-bromo-5-(2-oxo-pyrrolidin-1-yl)-phenyl]-amide;
(S)-4-(4-Fluoro-phenyl)-1-methyl-2-oxo-1,2,3,4-tetrahydro-pyrimidine-5-carboxylic acid(1,5-dimethyl-1H-indazol-6-yl)-amide;
(S)-4-(4-Fluoro-phenyl)-1-methyl-2-oxo-1,2,3,4-tetrahydro-pyrimidine-5-carboxylic acid(5-methyl-1H-indazol-6-yl)-amide;
(S)-4-(4-Fluoro-phenyl)-1-methyl-2-oxo-1,2,3,4-tetrahydro-pyrimidine-5-carboxylic acid[5-(2,4-dioxo-3,4-dihydro-2H-pyrimidin-1-yl)-2-methyl-phenyl]-amide;
(S)-4-(3-Fluoro-phenyl)-1-methyl-2-oxo-1,2,3,4-tetrahydro-pyrimidine-5-carboxylic acid[2-methyl-5-(6-oxo-6H-pyridazin-1-yl)-phenyl]-amide;
(S)-4-(4-Fluoro-phenyl)-1-methyl-2-oxo-1,2,3,4-tetrahydro-pyrimidine-5-carboxylic acid[2-methyl-5-(3-methyl-2-oxo-2H-pyridin-1-yl)-phenyl]-amide;
(S)-4-(4-Fluoro-phenyl)-1-methyl-2-oxo-1,2,3,4-tetrahydro-pyrimidine-5-carboxylic acid(2-methyl-1-oxo-1,2-dihydro-isoquinolin-5-yl)-amide;
4-(4,4-Difluoro-cyclohexyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;
(S)-4-(4-Fluoro-phenyl)-1-methyl-2-oxo-1,2,3,4-tetrahydro-pyrimidine-5-carboxylic acid[2-(2-hydroxy-ethyl)-1-oxo-1,2-dihydro-isoquinolin-5-yl]-amide;
(S)-4-(4-Fluoro-phenyl)-1-methyl-2-oxo-1,2,3,4-tetrahydro-pyrimidine-5-carboxylic acid[2-methyl-5-(2-oxo-2H-pyridin-1-yl)-phenyl]-amide;
(S)-4-(4-Fluoro-phenyl)-1-methyl-2-oxo-1,2,3,4-tetrahydro-pyrimidine-5-carboxylic acid[5-(6-methoxy-pyridazin-3-yl)-2-methyl-phenyl]-amide;
(S)-4-(4-Fluoro-phenyl)-1-methyl-2-oxo-1,2,3,4-tetrahydro-pyrimidine-5-carboxylic acid[5-(2,6-dioxo-3,6-dihydro-2H-pyrimidin-1-yl)-2-methyl-phenyl]-amide;
(S)-1-Methyl-2-oxo-4-phenyl-1,2,3,4-tetrahydro-pyrimidine-5-carboxylic acid [2-methyl-5-(2-methyl-3-oxo-2,3-dihydro-pyridazin-4-yl)-phenyl]-amide;
(S)-4-(4-Fluoro-phenyl)-1-methyl-2-oxo-1,2,3,4-tetrahydro-pyrimidine-5-carboxylic acid(1-dimethylcarbamoylmethyl-5-methyl-1H-indazol-6-yl)-amide;
(S)-4-(4-Fluoro-phenyl)-1-methyl-2-oxo-1,2,3,4-tetrahydro-pyrimidine-5-carboxylic acid{5-[1-(2-hydroxy-ethyl)-6-oxo-1,6-dihydro-pyridazin-3-yl]-2-methyl-phenyl}-amide;
(S)-4-(4-Fluoro-phenyl)-1-methyl-2-oxo-1,2,3,4-tetrahydro-pyrimidine-5-carboxylic acid[2-methyl-5-(1-methyl-2-oxo-1,2-dihydro-pyridin-3-yl)-phenyl]-amide;
(S)-4-(4-Fluoro-phenyl)-1-methyl-2-oxo-1,2,3,4-tetrahydro-pyrimidine-5-carboxylic acid{5-[1-((R)-2-hydroxy-3-methoxy-propyl)-6-oxo-1,6-dihydro-pyridazin-3-yl]-2-methyl-phenyl}-amide;
1-Methyl-2-oxo-4-phenyl-1,2,3,4-tetrahydro-pyrimidine-5-carboxylic acid[4-chloro-5-(2-hydroxy-ethoxy)-2-methyl-phenyl]-amide;
(S)-4-(4-Fluoro-phenyl)-1-methyl-2-oxo-1,2,3,4-tetrahydro-pyrimidine-5-carboxylic acid[4-chloro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[5-(4-ethyl-3,5-dioxo-4,5-dihydro-3H-[1,2,4]triazin-2-yl)-2-methyl-phenyl]-amide;

(S)-4-(4-Fluoro-phenyl)-1-methyl-2-oxo-1,2,3,4-tetrahydro-pyrimidine-5-carboxylic acid(2,5-dimethyl-quinolin-6-yl)-amide;

(S)-4-(4-Fluoro-phenyl)-1-methyl-2-oxo-1,2,3,4-tetrahydro-pyrimidine-5-carboxylic acid[4-chloro-2-methyl-5-(3-methyl-2-oxo-2H-pyridin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(4-methyl-6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(3-methyl-2,4-dioxo-3,4-dihydro-2H-pyrimidin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(1-methyl-2-oxo-1,2-dihydro-pyridin-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(5-methyl-2-oxo-2H-pyridin-1-yl)-phenyl]-amide;

(S)-4-(4-Fluoro-phenyl)-1-methyl-2-oxo-1,2,3,4-tetrahydro-pyrimidine-5-carboxylic acid[2-fluoro-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(4-methyl-6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-fluoro-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[3-fluoro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(1-methyl-6-oxo-1,6-dihydro-pyridin-3-yl)-phenyl]-amide;

(R)-1-Methyl-2-oxo-4-phenyl-1,2,3,4-tetrahydro-pyrimidine-5-carboxylic acid (2,6-dimethyl-1-oxo-1,2-dihydro-isoquinolin-5-yl)-amide; and (S)-4-(4-Fluoro-phenyl)-1-methyl-2-oxo-1,2,3,4-tetrahydro-pyrimidine-5-carboxylic acid[4-fluoro-2-methyl-5-(2-methyl-3-oxo-2,3-dihydro-pyridazin-4-yl)-phenyl]-amide.

19. The compound of claim 18, wherein said compound is selected from:

(R)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide;

(S)-4-(4-Fluoro-phenyl)-2-oxo-1,2,3,4-tetrahydro-pyrimidine-5-carboxylic acid [2-methyl-5-(5-methyl-1H-pyrazol-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;

4-(3-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(4-methyl-pyrazol-1-yl)-phenyl]-amide;

(S)-4-(4-Fluoro-phenyl)-1-methyl-2-oxo-1,2,3,4-tetrahydro-pyrimidine-5-carboxylic acid[5-(4,5-dimethyl-4H-[1,2,4]triazol-3-yl)-2-methyl-phenyl]-amide;

(S)-4-(4-Fluoro-phenyl)-1-methyl-2-oxo-1,2,3,4-tetrahydropyrimidine-5-carboxylic acid{5-[1-((R)-2,3-dihydroxy-propyl)-5-methyl-1H-pyrazol-3-yl]-2-methyl-phenyl}-amide;

(S)-4-(4-Fluoro-phenyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid{5-[1-((R)-2-hydroxy-3-methoxy-propyl)-5-methyl-1H-pyrazol-3-yl]-2-methyl-phenyl}-amide;

(S)-4-(4-Fluoro-phenyl)-1-methyl-2-oxo-1,2,3,4-tetrahydro-pyrimidine-5-carboxylic acid{5-[4-((R)-2-hydroxy-3-methoxy-propyl)-3,5-dioxo-4,5-dihydro-3H-[1,2,4]triazin-2-yl]-2-methyl-phenyl}-amide;

S)-4-(4-Fluoro-phenyl)-1-methyl-2-oxo-1,2,3,4-tetrahydro-pyrimidine-5-carboxylic acid[2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(3-methyl-6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(6-oxo-1,6-dihydro-pyrazin-2-yl)-phenyl]-amide;

(S)-4-(4-Fluoro-phenyl)-1-methyl-2-oxo-1,2,3,4-tetrahydro-pyrimidine-5-carboxylic acid[2-methyl-5-(3-oxo-2,3-dihydro-pyridazin-4-yl)-phenyl]-amide;

(S)-4-(3-Fluoro-phenyl)-1-methyl-2-oxo-1,2,3,4-tetrahydro-pyrimidine-5-carboxylic acid[2-methyl-5-(5-methyl-1H-pyrazol-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(4-methyl-3,5-dioxo-4,5-dihydro-3H-[1,2,4]triazin-2-yl)-phenyl]-amide;

(S)-4-(4-Fluoro-phenyl)-1-methyl-2-oxo-1,2,3,4-tetrahydro-pyrimidine-5-carboxylic acid{5-[1-((S)-2-hydroxy-3-methoxy-propyl)-5-methyl-1H-pyrazol-3-yl]-2-methyl-phenyl}-amide;

(S)-4-(3-Fluoro-phenyl)-1-methyl-2-oxo-1,2,3,4-tetrahydro-pyrimidine-5-carboxylic acid[2-methyl-5-(4-methyl-3,5-dioxo-4,5-dihydro-3H-[1,2,4]triazin-2-yl)-phenyl]-amide;

(S)-4-(4-Fluoro-phenyl)-1-methyl-2-oxo-1,2,3,4-tetrahydro-pyrimidine-5-carboxylic acid[5-(2-ethyl-3-oxo-2,3-dihydro-pyridazin-4-yl)-2-methyl-phenyl]-amide;

(S)-4-(4-Fluoro-phenyl)-1-methyl-2-oxo-1,2,3,4-tetrahydro-pyrimidine-5-carboxylic acid[2-methyl-5-(1-methyl-6-oxo-1,6-dihydro-pyridazin-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(6-oxo-1,6-dihydro-pyridazin-3-yl)-phenyl]-amide;

(S)-4-(4-Fluoro-phenyl)-1-methyl-2-oxo-1,2,3,4-tetrahydro-pyrimidine-5-carboxylic acid{5-[2-((R)-2-hydroxy-3-methoxy-propyl)-3-oxo-2,3-dihydro-pyridazin-4-yl]-2-methyl-phenyl}-amide;

(S)-4-(3-Fluoro-phenyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid[2-bromo-5-(2-oxo-pyrrolidin-1-yl)-phenyl]-amide;

(S)-4-(4-Fluoro-phenyl)-1-methyl-2-oxo-1,2,3,4-tetrahydro-pyrimidine-5-carboxylic acid[5-(2,4-dioxo-3,4-dihydro-2H-pyrimidin-1-yl)-2-methyl-phenyl]-amide;

(S)-4-(3-Fluoro-phenyl)-1-methyl-2-oxo-1,2,3,4-tetrahydro-pyrimidine-5-carboxylic acid[2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(3-methyl-2-oxo-2H-pyridin-1-yl)-phenyl]-amide;

4-(4,4-Difluoro-cyclohexyl)-1-methyl-2-oxo-1,2,3,4-tetrahydro-pyrimidine-5-carboxylic acid[2-methyl-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid[2-methyl-5-(2-oxo-2H-pyridin-1-yl)-phenyl]-amide;

(S)-4-(4-Fluoro-phenyl)-1-methyl-2-oxo-1,2,3,4-tetrahydro-pyrimidine-5-carboxylic acid[5-(6-methoxy-pyridazin-3-yl)-2-methyl-phenyl]-amide;

(S)-4-(4-Fluoro-phenyl)-1-methyl-2-oxo-1,2,3,4-tetrahydro-pyrimidine-5-carboxylic acid[5-(2,6-dioxo-3,6-dihydro-2H-pyrimidin-1-yl)-2-methyl-phenyl]-amide;

(S)-1-Methyl-2-oxo-4-phenyl-1,2,3,4-tetrahydro-pyrimidine-5-carboxylic acid [2-methyl-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid{5-[1-(2-hydroxy-ethyl)-6-oxo-1,6-dihydro-pyridazin-3-yl]-2-methyl-phenyl}-amide;

(S)-4-(4-Fluoro-phenyl)-1-methyl-2-oxo-1,2,3,4-tetrahydro-pyrimidine-5-carboxylic acid[2-methyl-5-(1-methyl-2-oxo-1,2-dihydro-pyridin-3-yl)-phenyl]-amide;

(S)-4-(4-Fluoro-phenyl)-1-methyl-2-oxo-1,2,3,4-tetrahydro-pyrimidine-5-carboxylic acid{5-[1-((R)-2-hydroxy-3-methoxy-propyl)-6-oxo-1,6-dihydro-pyridazin-3-yl]-2-methyl-phenyl}-amide;

(S)-4-(4-Fluoro-phenyl)-1-methyl-2-oxo-1,2,3,4-tetrahydro-pyrimidine-5-carboxylic acid[4-chloro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[5-(4-ethyl-3,5-dioxo-4,5-dihydro-3H-[1,2,4]triazin-2-yl)-2-methyl-phenyl]-amide;

(S)-4-(4-Fluoro-phenyl)-1-methyl-2-oxo-1,2,3,4-tetrahydro-pyrimidine-5-carboxylic acid[4-chloro-2-methyl-5-(3-methyl-2-oxo-2H-pyridin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(4-methyl-6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[2-methyl-5-(3-methyl-2,4-dioxo-3,4-dihydro-2H-pyrimidin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(1-methyl-2-oxo-1,2-dihydro-pyridin-3-yl)-phenyl]-amide;

(S)-4-(4-Fluoro-phenyl)-1-methyl-2-oxo-1,2,3,4-tetrahydro-pyrimidine-5-carboxylic acid[2-methyl-5-(5-methyl-2-oxo-2H-pyridin-1-yl)-phenyl]-amide;

(S)-4-(4-Fluoro-phenyl)-1-methyl-2-oxo-1,2,3,4-tetrahydro-pyrimidine-5-carboxylic acid[2-fluoro-5-(2-methyl-3-oxo-2,3-dihydro-pyridazin-4-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(4-methyl-6-oxo-6H-pyridazin-1-yl)-phenyl]-amide (S)-4-(4-Fluoro-phenyl)-1-methyl-2-oxo-1,2,3,4-tetrahydro-pyrimidine-5-carboxylic acid[2-fluoro-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[3-fluoro-2-methyl-5-(6-oxo-6H-pyridazin-1-yl)-phenyl]-amide;

(S)-4-(4-Fluoro-phenyl)-1-methyl-2-oxo-1,2,3,4-tetrahydro-pyrimidine-5-carboxylic acid[4-fluoro-2-methyl-5-(1-methyl-6-oxo-1,6-dihydro-pyridin-3-yl)-phenyl]-amide; and (S)-4-(4-Fluoro-phenyl)-1-methyl-2-oxo-1,2,3,4-tetrahydro-pyrimidine-5-carboxylic acid[4-fluoro-2-methyl-5-(2-methyl-3-oxo-2,3-dihydro-pyridazin-4-yl)-phenyl]-amide.

20. The compound of claim 18, wherein said compound is selected from:

(S)-4-(4-Fluoro-phenyl)-1-methyl-2-oxo-1,2,3,4-tetrahydro-pyrimidine-5-carboxylic acid(6-methyl-quinolin-5-yl)-amide;

(S)-4-(4-Fluoro-phenyl)-1-methyl-2-oxo-1,2,3,4-tetrahydro-pyrimidine-5-carboxylic acid(2,6-dimethyl-quinolin-5-yl)-amide;

(S)-4-(4-Fluoro-phenyl)-1-methyl-2-oxo-1,2,3,4-tetrahydro-pyrimidine-5-carboxylic acid(6-methyl-2-oxo-1,2-dihydro-quinolin-5-yl)-amide;

(S)-4-(4-Fluoro-phenyl)-1-methyl-2-oxo-1,2,3,4-tetrahydro-pyrimidine-5-carboxylic acid(5-ethyl-2-methyl-quinolin-6-yl)-amide;

(S)-4-(4-Fluoro-phenyl)-1-methyl-2-oxo-1,2,3,4-tetrahydro-pyrimidine-5-carboxylic acid[1-(2-hydroxy-ethyl)-5-methyl-1H-indazol-6-yl]-amide;

(S)-4-(4-Fluoro-phenyl)-1-methyl-2-oxo-1,2,3,4-tetrahydro-pyrimidine-5-carboxylic acid(1,5-dimethyl-1H-indazol-6-yl)-amide;

(S)-4-(4-Fluoro-phenyl)-1-methyl-2-oxo-1,2,3,4-tetrahydro-pyrimidine-5-carboxylic acid(5-methyl-1H-indazol-6-yl)-amide;

(S)-4-(4-Fluoro-phenyl)-1-methyl-2-oxo-1,2,3,4-tetrahydro-pyrimidine-5-carboxylic acid(2-methyl-1-oxo-1,2-dihydro-isoquinolin-5-yl)-amide;

(S)-4-(4-Fluoro-phenyl)-1-methyl-2-oxo-1,2,3,4-tetrahydro-pyrimidine-5-carboxylic acid[2-(2-hydroxy-ethyl)-1-oxo-1,2-dihydro-isoquinolin-5-yl]-amide;

S)-4-(4-Fluoro-phenyl)-1-methyl-2-oxo-1,2,3,4-tetrahydro-pyrimidine-5-carboxylic acid(1-dimethylcarbamoylmethyl-5-methyl-1H-indazol-6-yl)-amide;

(S)-4-(4-Fluoro-phenyl)-1-methyl-2-oxo-1,2,3,4-tetrahydro-pyrimidine-5-carboxylic acid(2,5-dimethyl-quinolin-6-yl)-amide; and (R)-1-Methyl-2-oxo-4-phenyl-1,2,3,4-tetrahydro-pyrimidine-5-carboxylic acid (2,6-dimethyl-1-oxo-1,2-dihydro-isoquinolin-5-yl)-amid.

21. A method for treating arthritis, said method comprising administering to a subject in need thereof an effective amount of a compound of claim 1.

* * * * *